(12) United States Patent
Torigoe et al.

(10) Patent No.: US 11,028,136 B2
(45) Date of Patent: Jun. 8, 2021

(54) TUMOR ANTIGEN PEPTIDE

(71) Applicants: Sapporo Medical University, Sapporo (JP); Medical & Biological Laboratories Co., Ltd., Aichi (JP)

(72) Inventors: Toshihiko Torigoe, Sapporo (JP); Eri Atsuyama, Nagano (JP); Hironori Otaka, Nagano (JP); Kazue Nakano, Nagano (JP); Dongliang Li, Nagano (JP); Shingo Toji, Nagano (JP); Takuya Asano, Sapporo (JP); Ryota Horibe, Sapporo (JP); Yoshihiko Hirohashi, Sapporo (JP); Noriyuki Sato, Sapporo (JP); Tsuyoshi Saito, Sapporo (JP)

(73) Assignees: Sapporo Medical University, Sapporo (JP); Medical & Biological Laboratories Co., Ltd., Aichi (JP)

( * ) Notice: Subject to any disclaimer, the term of this patent is extended or adjusted under 35 U.S.C. 154(b) by 380 days.

(21) Appl. No.: 15/514,169

(22) PCT Filed: Sep. 24, 2015

(86) PCT No.: PCT/JP2015/076994
§ 371 (c)(1),
(2) Date: Mar. 24, 2017

(87) PCT Pub. No.: WO2016/047715
PCT Pub. Date: Mar. 31, 2016

(65) Prior Publication Data
US 2017/0298109 A1    Oct. 19, 2017

(30) Foreign Application Priority Data

Sep. 24, 2014 (JP) .............................. JP2014-194391

(51) Int. Cl.
*A61K 35/17* (2015.01)
*C12N 5/0783* (2010.01)
*C07K 14/47* (2006.01)
*C12N 15/63* (2006.01)
*A61K 48/00* (2006.01)
*C12N 15/09* (2006.01)
*A61K 35/76* (2015.01)
*C12N 15/00* (2006.01)
*C12N 5/10* (2006.01)
*A61K 39/00* (2006.01)
*C07K 7/06* (2006.01)
*C07K 14/74* (2006.01)
*C07K 16/18* (2006.01)
*C07K 16/30* (2006.01)
*C12N 5/078* (2010.01)
*G01N 33/574* (2006.01)
*C07K 14/82* (2006.01)

(52) U.S. Cl.
CPC .......... *C07K 14/4703* (2013.01); *A61K 35/76* (2013.01); *A61K 39/00* (2013.01); *A61K 39/0011* (2013.01); *A61K 48/00* (2013.01); *C07K 7/06* (2013.01); *C07K 14/70539* (2013.01); *C07K 16/18* (2013.01); *C07K 16/30* (2013.01); *C12N 5/0634* (2013.01); *C12N 5/0638* (2013.01); *C12N 5/10* (2013.01); *C12N 15/00* (2013.01); *C12N 15/09* (2013.01); *G01N 33/57496* (2013.01); *A61K 2039/5158* (2013.01); *A61K 2039/572* (2013.01); *C07K 14/82* (2013.01); *C12N 2510/00* (2013.01); *G01N 2333/4704* (2013.01)

(58) Field of Classification Search
None
See application file for complete search history.

(56) References Cited

U.S. PATENT DOCUMENTS

| | | | |
|---|---|---|---|
| 2008/0207497 A1* | 8/2008 | Ramakrishna | A61K 38/19 514/19.3 |
| 2009/0060930 A1* | 3/2009 | Mautino | A61K 39/0011 424/185.1 |
| 2009/0169613 A1 | 7/2009 | Reznik et al. | |
| 2010/0021465 A1* | 1/2010 | Lobanenkov | G01N 33/574 424/139.1 |
| 2012/0003251 A1 | 1/2012 | Mautino et al. | |

FOREIGN PATENT DOCUMENTS

| | | |
|---|---|---|
| JP | 2010-502192 A | 1/2010 |
| WO | WO 2008/028066 A2 | 3/2008 |

OTHER PUBLICATIONS

Loukinov et al, BORIS, a novel male germ-line-specific protein associated with epigenetic reprogramming events, shares the same 11-zinc-finger domain with CTCF, the insulator protein involved in reading imprinting marks in the soma, PNAS, 2002, pp. 6806-6811.*

(Continued)

*Primary Examiner* — Maria Marvich
(74) *Attorney, Agent, or Firm* — Wolf, Greenfield & Sacks, P.C.

(57) ABSTRACT

The object is to provide a tumor antigen peptide that is specifically presented on a cancer and a cancer stem cell, and a pharmaceutical composition, etc. that is useful for the prevention and/or treatment of a cancer and contains the above peptide as an active ingredient.

The above object has been accomplished by providing a BORIS-derived partial peptide belonging to isoform A or C or subfamily 5 or 6, a polynucleotide encoding the peptide, a pharmaceutical composition containing the above as an active ingredient, and an agent for the prevention and/or treatment of a cancer, the agent containing the above as an active ingredient and inducing CTLs.

7 Claims, 57 Drawing Sheets
Specification includes a Sequence Listing.

(56) References Cited

OTHER PUBLICATIONS

Ho et al, Side Population in Human Lung Cancer Cell Lines and Tumors Is Enriched with Stem-like Cancer Cells, Cancer Res 2007; 67: (10). May 15, 2007, 4827-4833.*

Babiak et al, Frequent T cell responses against immunogenic targets in lung cancer patients for targeted immunotherapy, Oncology Reports 31: 384-390, 2014.*

Sultan et al, The route of administration dictates the immunogenicity of peptide based cancer vaccines in mice, Cancer Immunology, Immunotherapy (2019) 68:455-466.*

Stella et al. Lung-Seeking Metastases, Cancers 2019, 11, pp. 1-18.*

[No Author Listed] Expression of cancer testis antigen BORIS in lung cancer stem cell-like cells and immunotherapy targeting BORIS antigen. Abstract 19. Program of the 95$^{th}$ Hokkaido Medical Congress. Sep. 12, 2015.

[No Author Listed] BORIS variant subfamily 6. The 74th Annual Meeting of the Japanese Cancer Association. Abstract. Poster P-1233. Oct. 8, 2015.

[No Author Listed] The 74th Annual Meeting of the Japanese Cancer Association Abstract, Poster P-1255. Oct. 8, 2015.

[No Author Listed] The 74th Annual Meeting of the Japanese Cancer Association Abstract, Poster P-1264. Oct. 8, 2015.

Pugacheva et al., The structural complexity of the human BORIS gene in gametogenesis and cancer. PLoS One. Nov. 8, 2010;5(11):e13872. doi: 10.1371/journal.pone.0013872.

Romagnoli et al., Evaluation of the potential role of the new cancer-testis antigen BORIS for the development of novel strategies of immunotherapy of cancer. Section 1A. New therapeutic strategies. Rapporti ISTISAN 06/50. Jul. 4-6, 2006; pp. 36-40.

Ryota et al., The expression of cancer testis antigen BORIS gene in lung cancer stem cell-like cells and examination of the immunotherapy targeting BORIS antigen. Presentation PowerPoint. Sep. 12, 2015.

Asano et al., Brother of the regulator of the imprinted site (BORIS) variant subfamily 6 is involved in cervical cancer stemness and can be a target of immunotherapy. Oncotarget. Mar. 8, 2016;7(10):11223-37. doi: 10.18632/oncotarget.7165.

* cited by examiner

[Fig. 1]
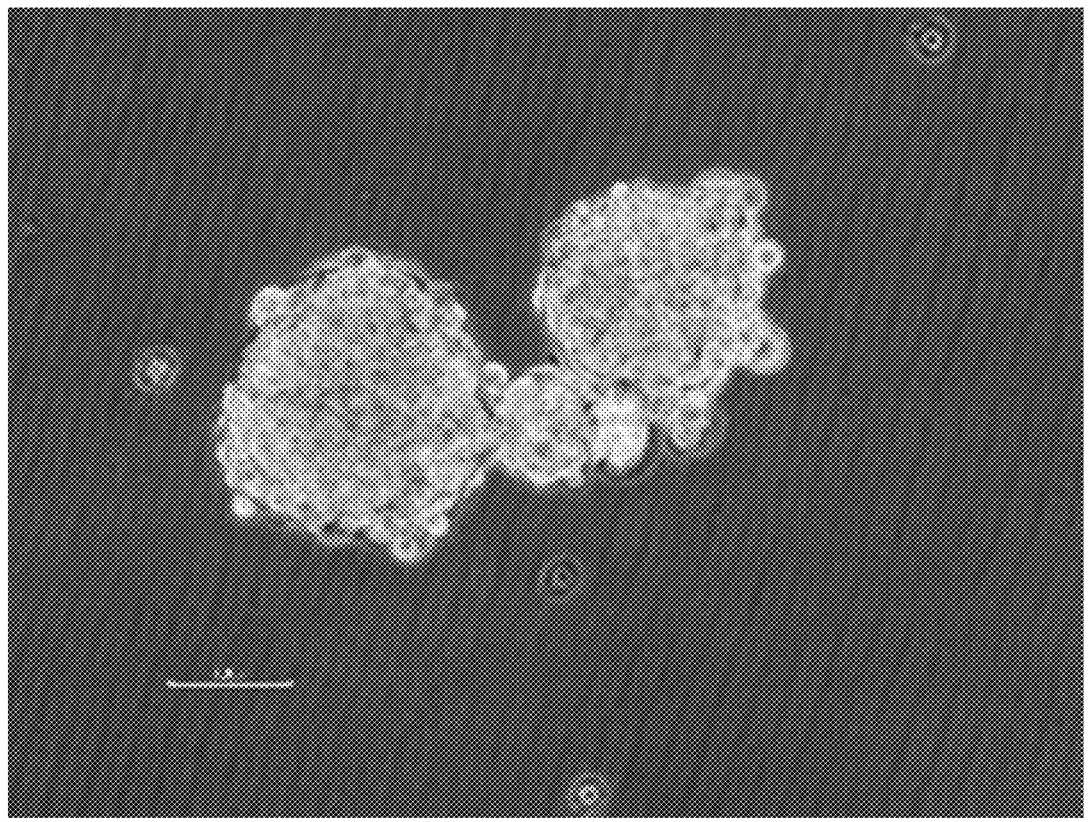
[Fig. 2]
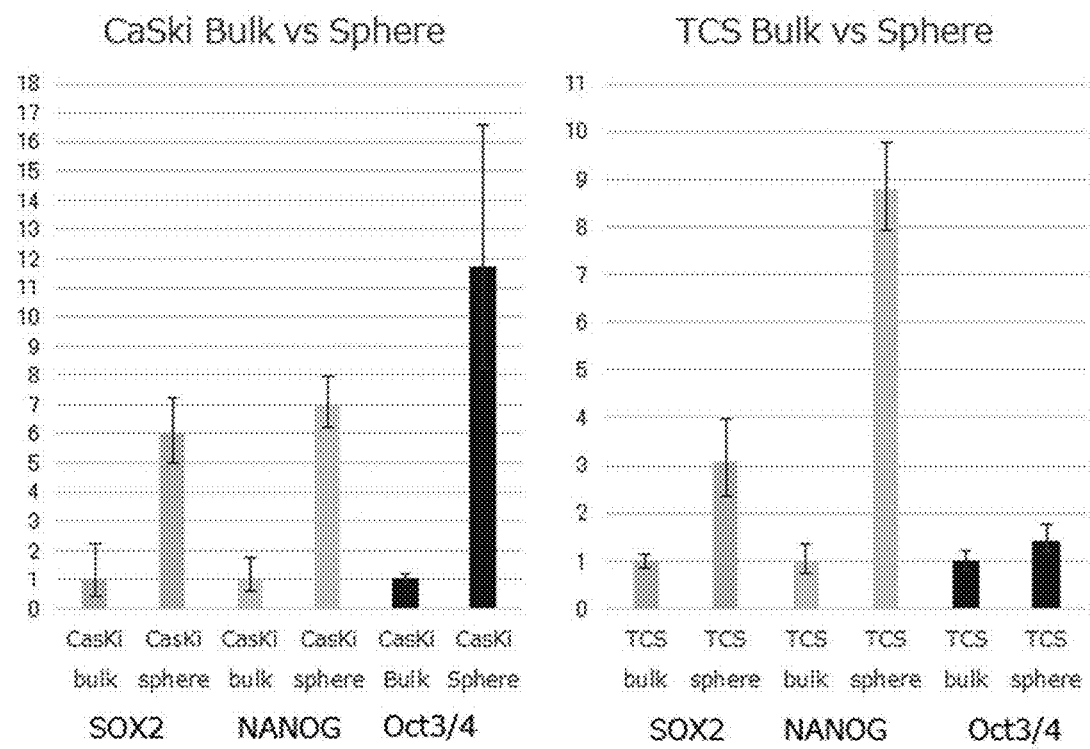

[Fig. 3]
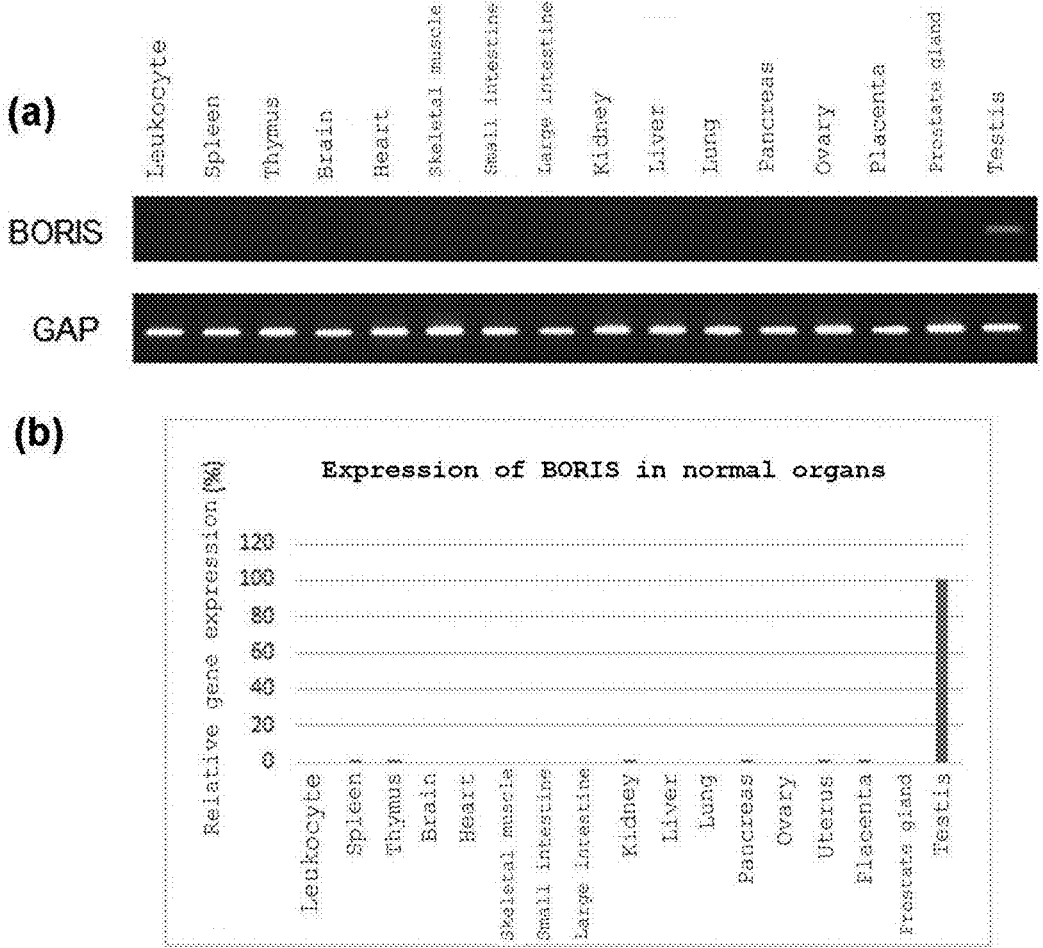

[Fig. 4]
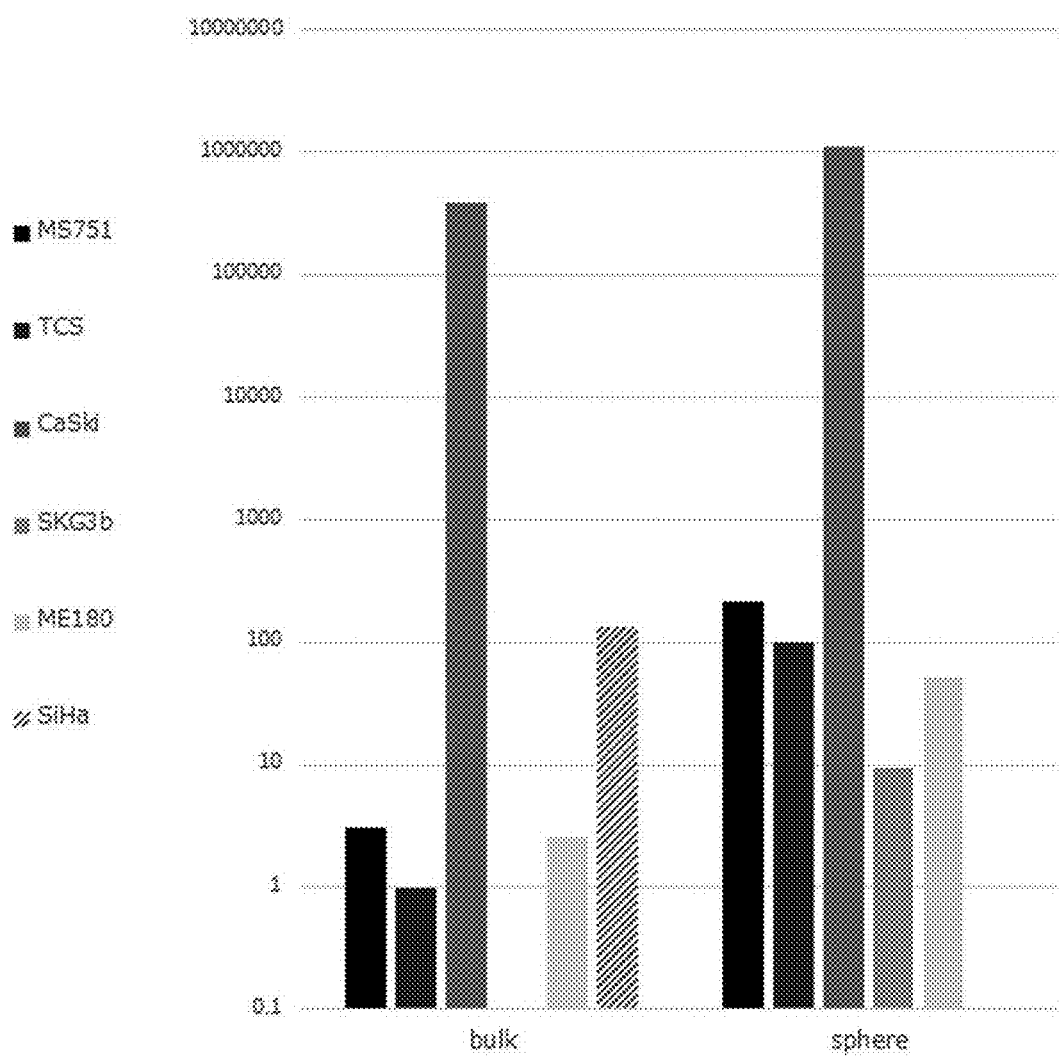

[Fig. 5]
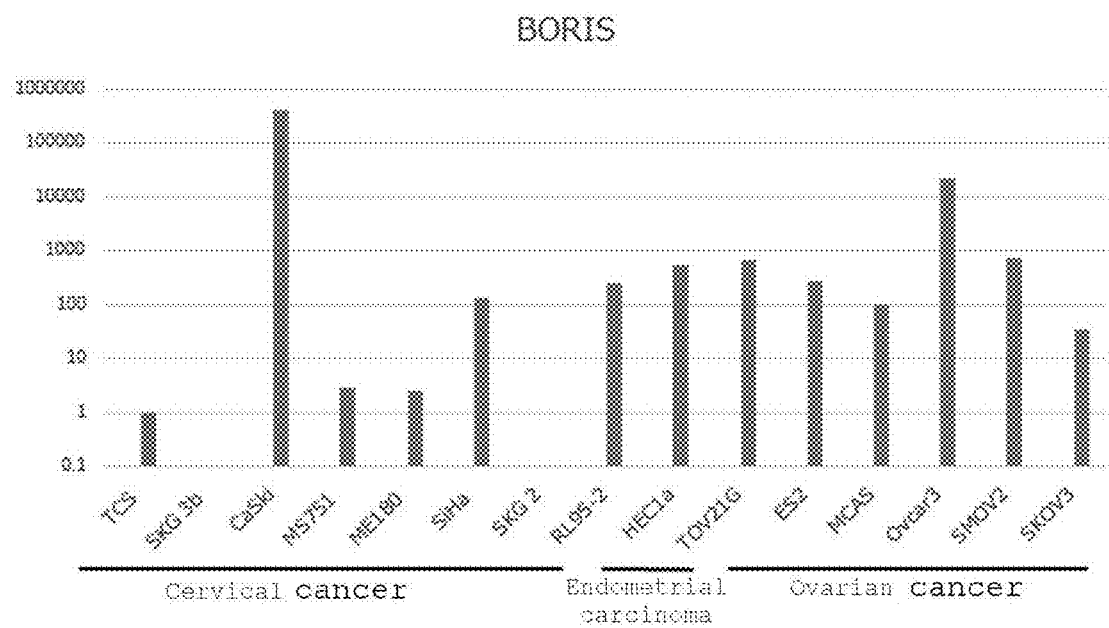

[Fig. 6]
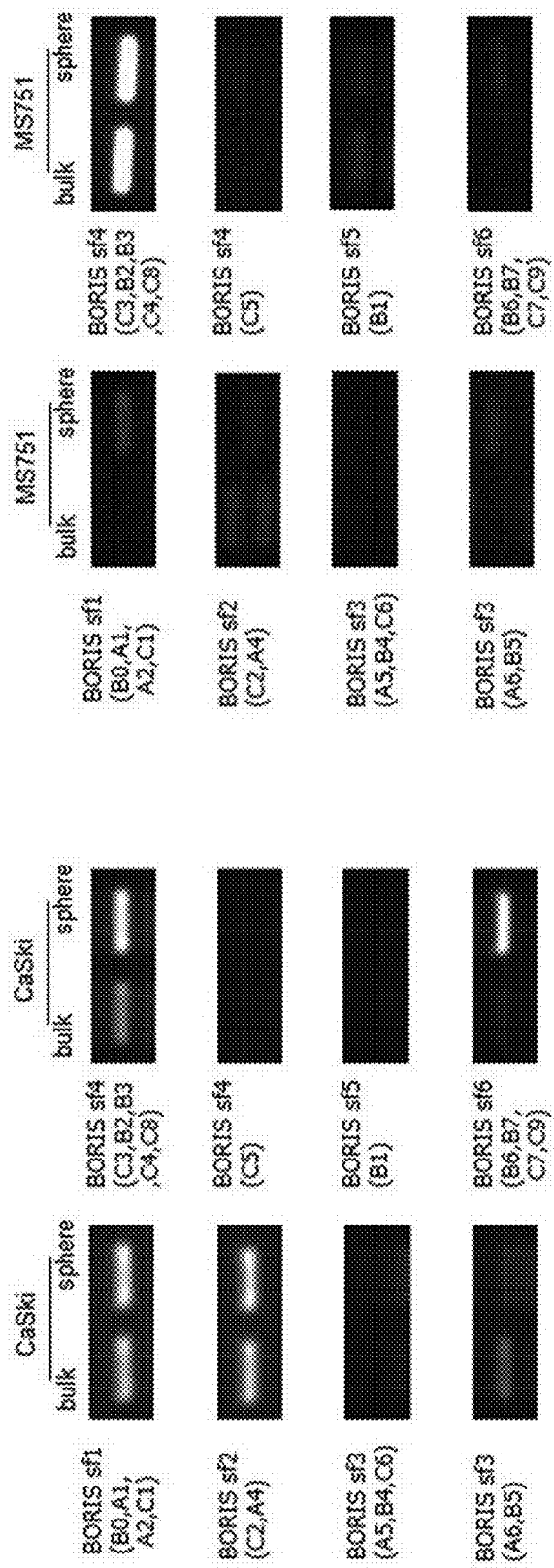

[Fig. 7]
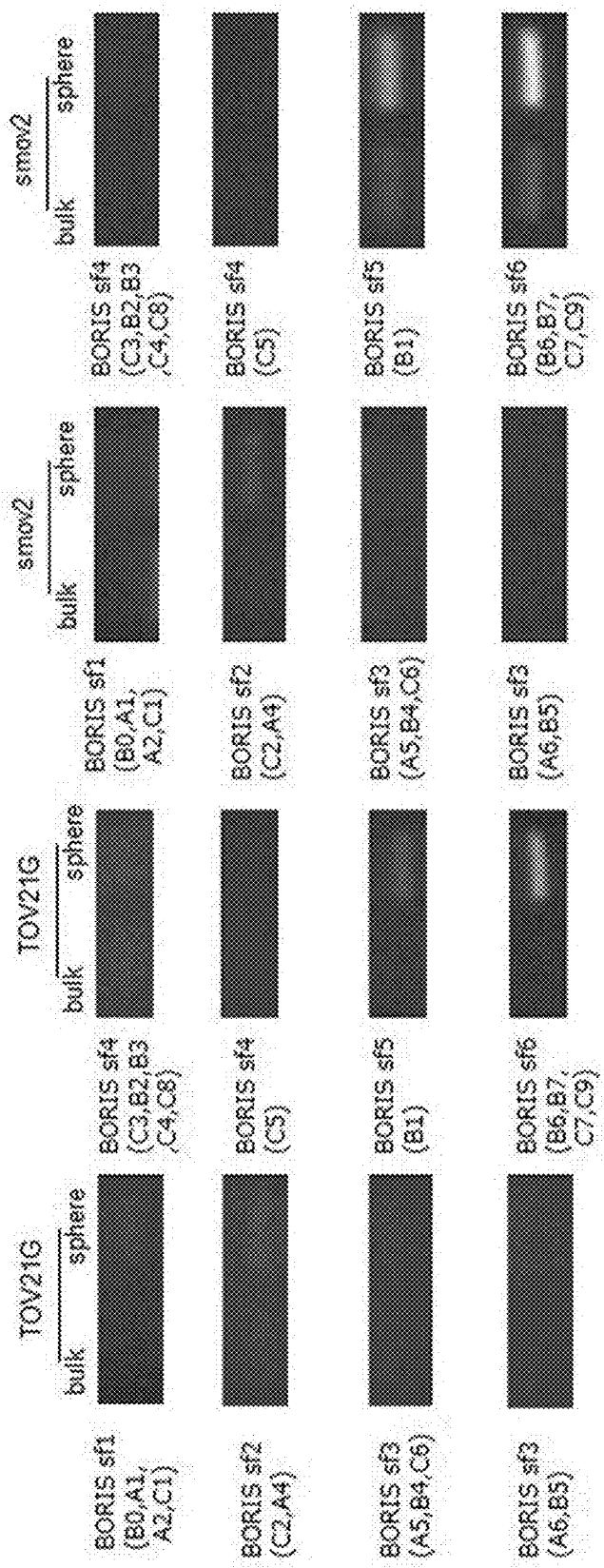

[Fig. 8-1]
Sphere formation assay in BORIS-overexpressing TCS cell line
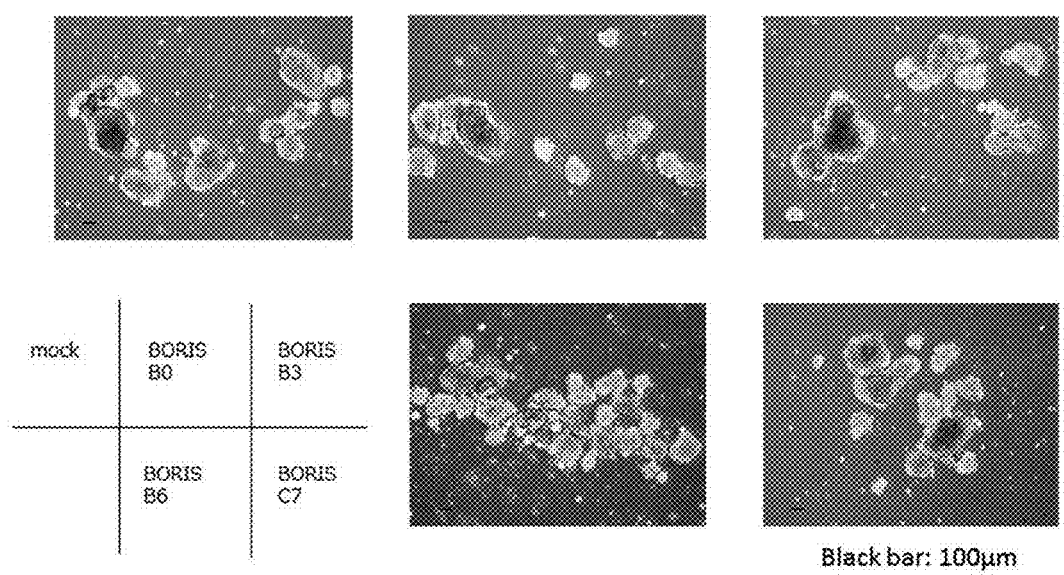
Black bar: 100μm
[Fig. 8-2]
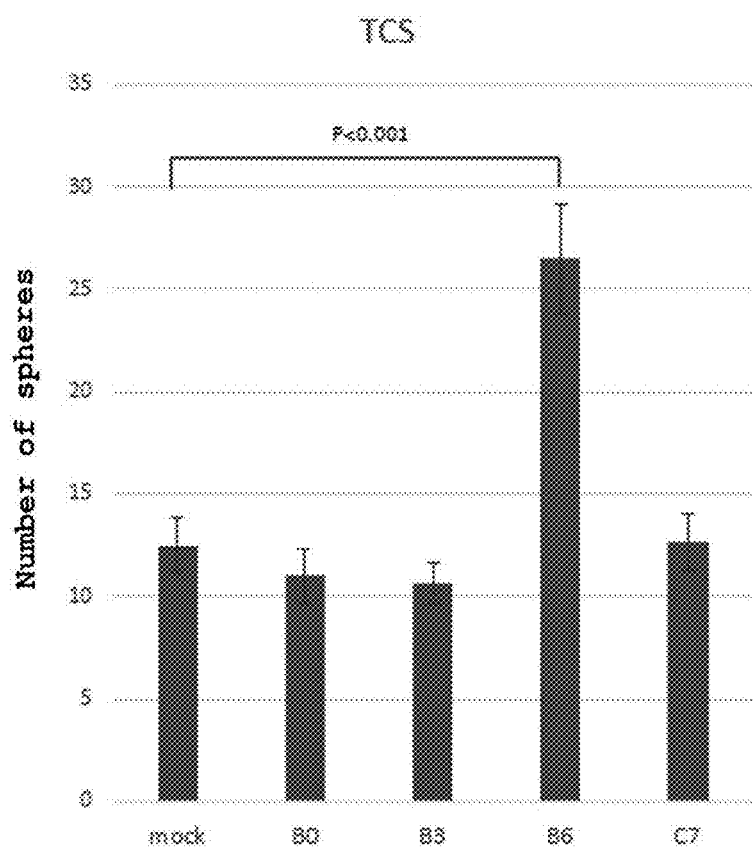

[Fig. 9-1]
Sphere formation assay in BORIS-overexpressing SKG-IIIb cell line
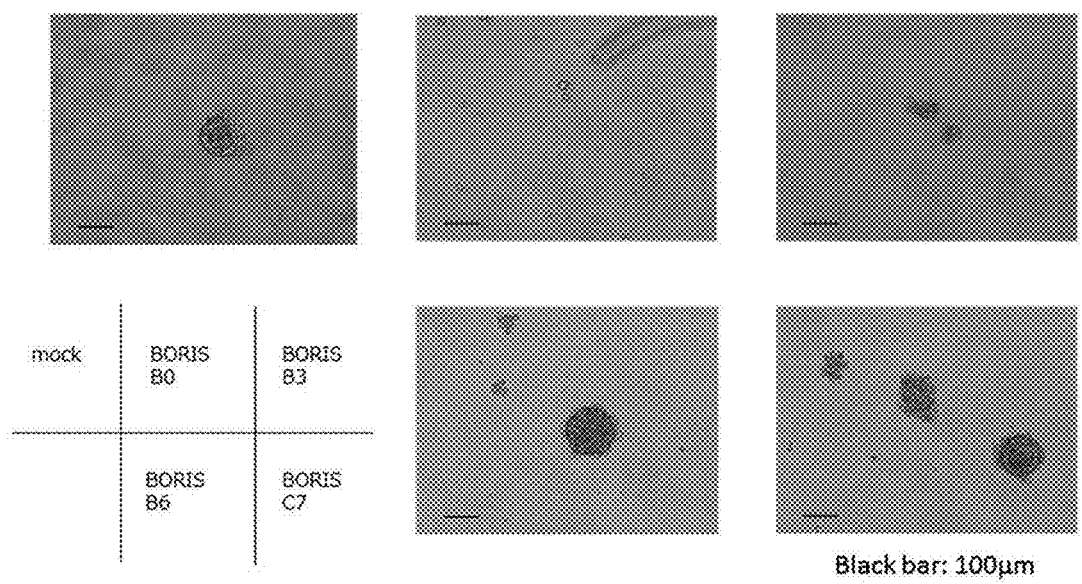
Black bar: 100μm
[Fig. 9-2]
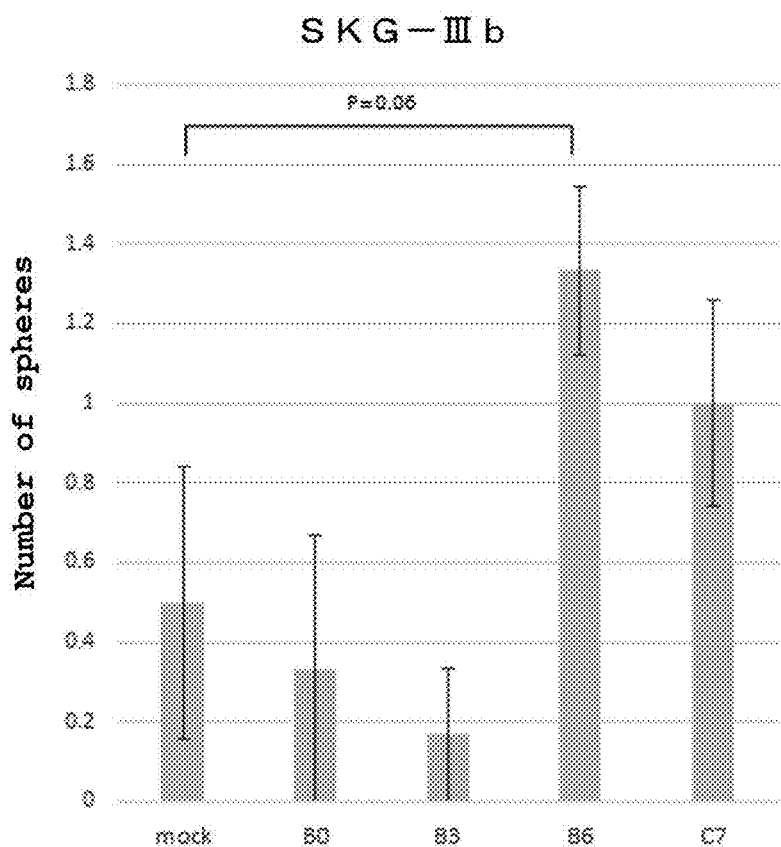

[Fig. 10]
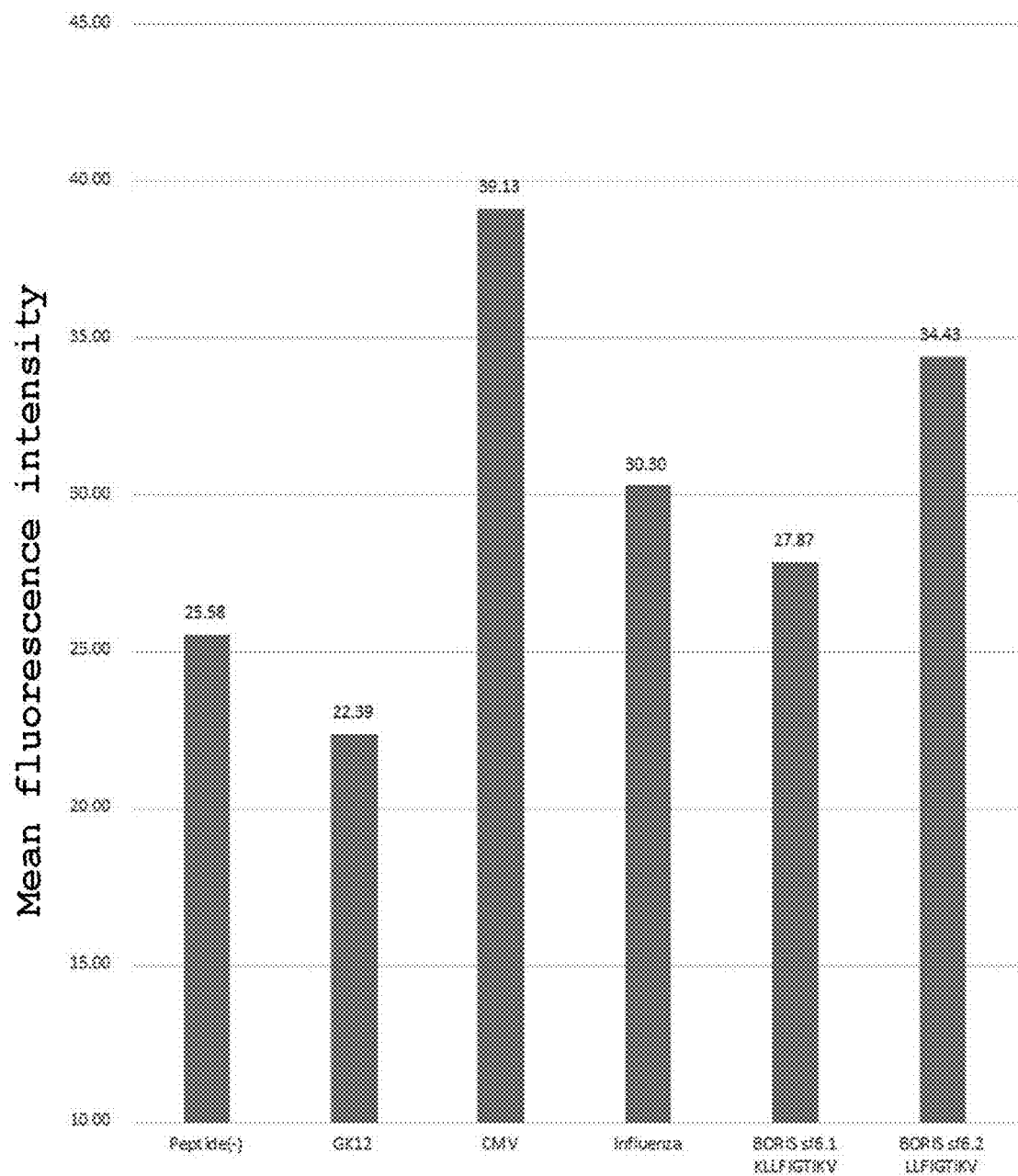

[Fig. 11]
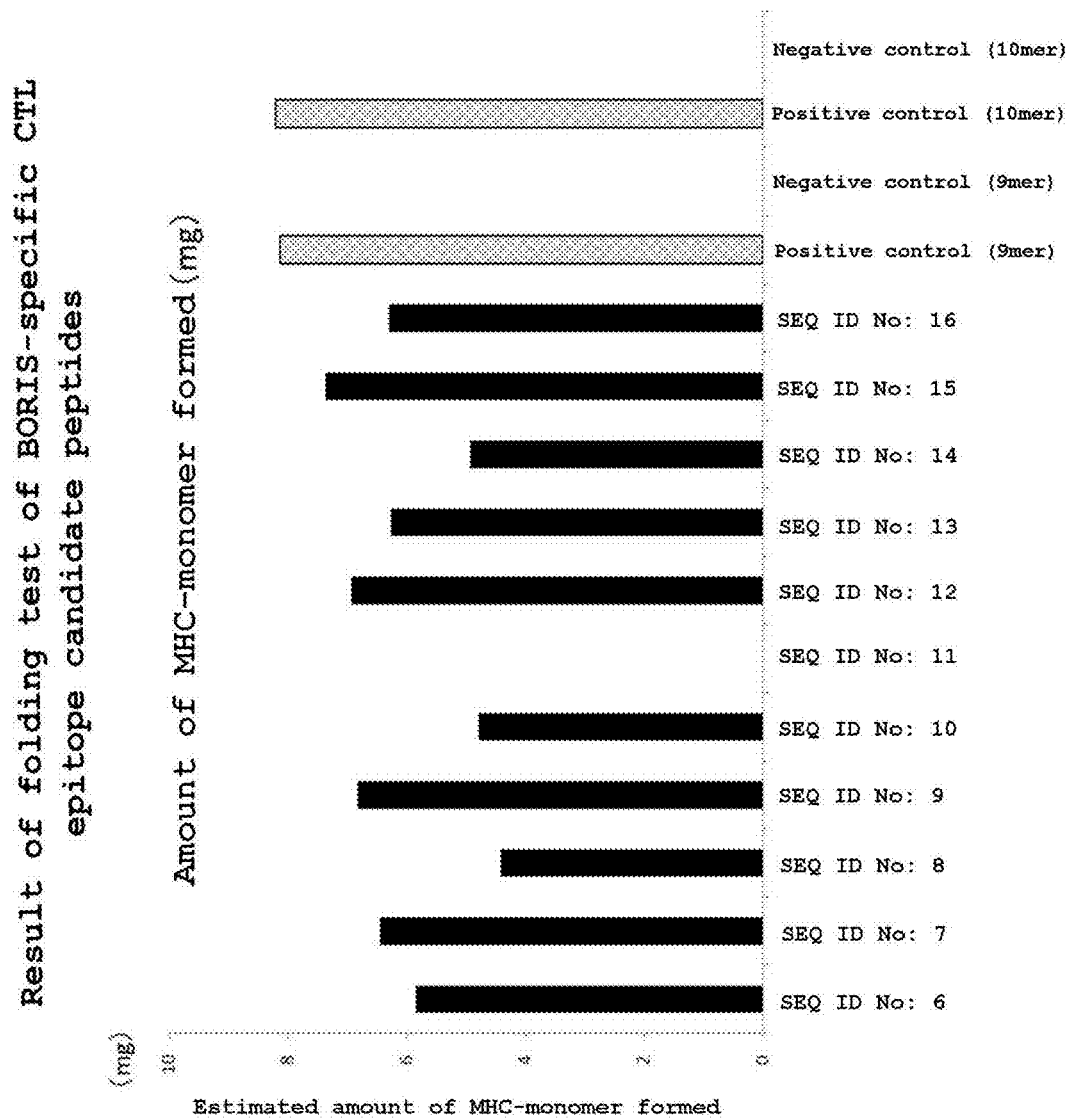

[Fig. 12-1]
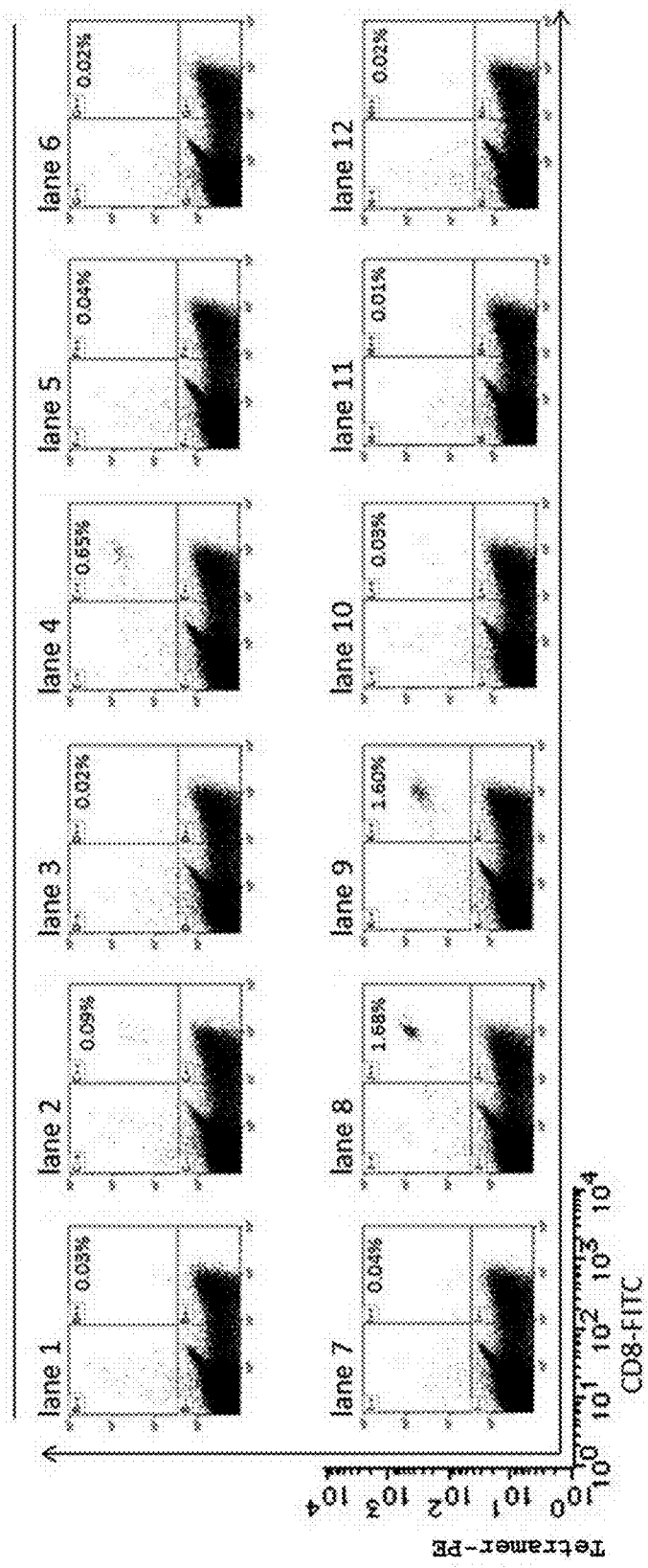

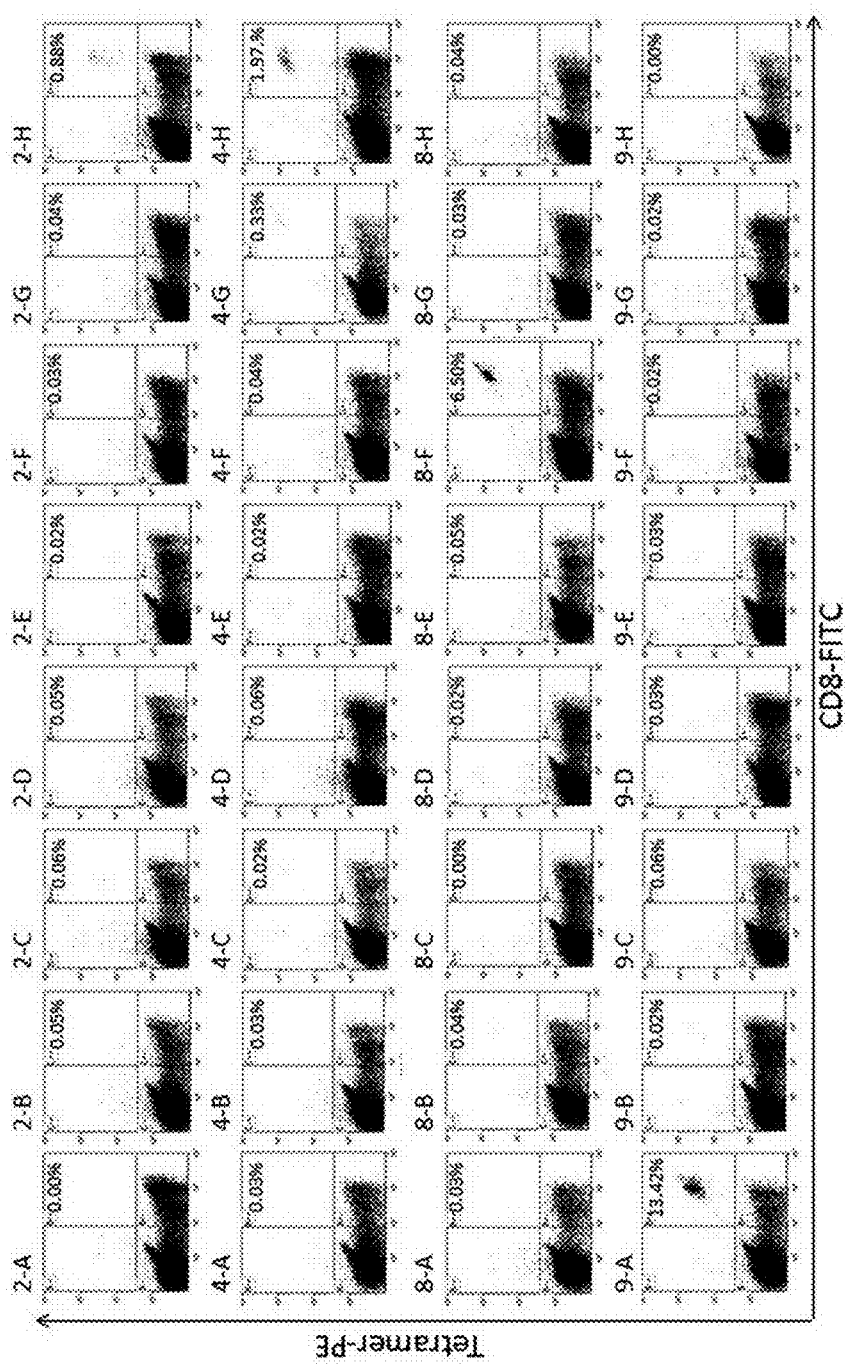
[Fig. 12-2]

[Fig. 13]
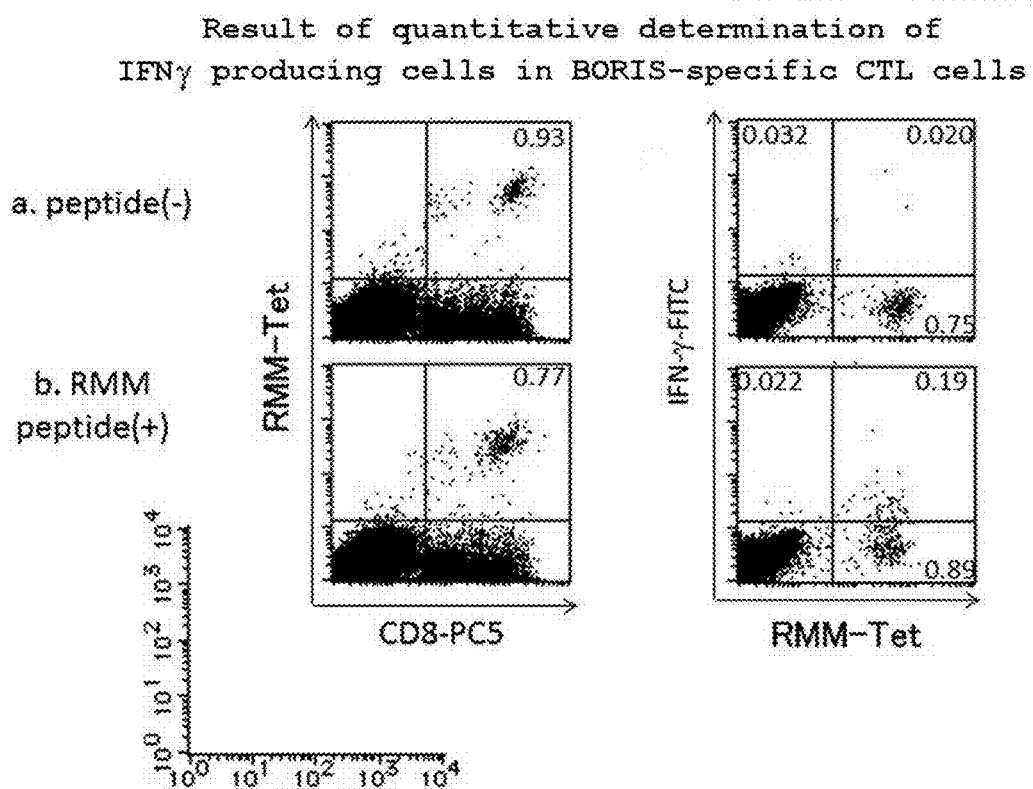
[Fig. 14-1]
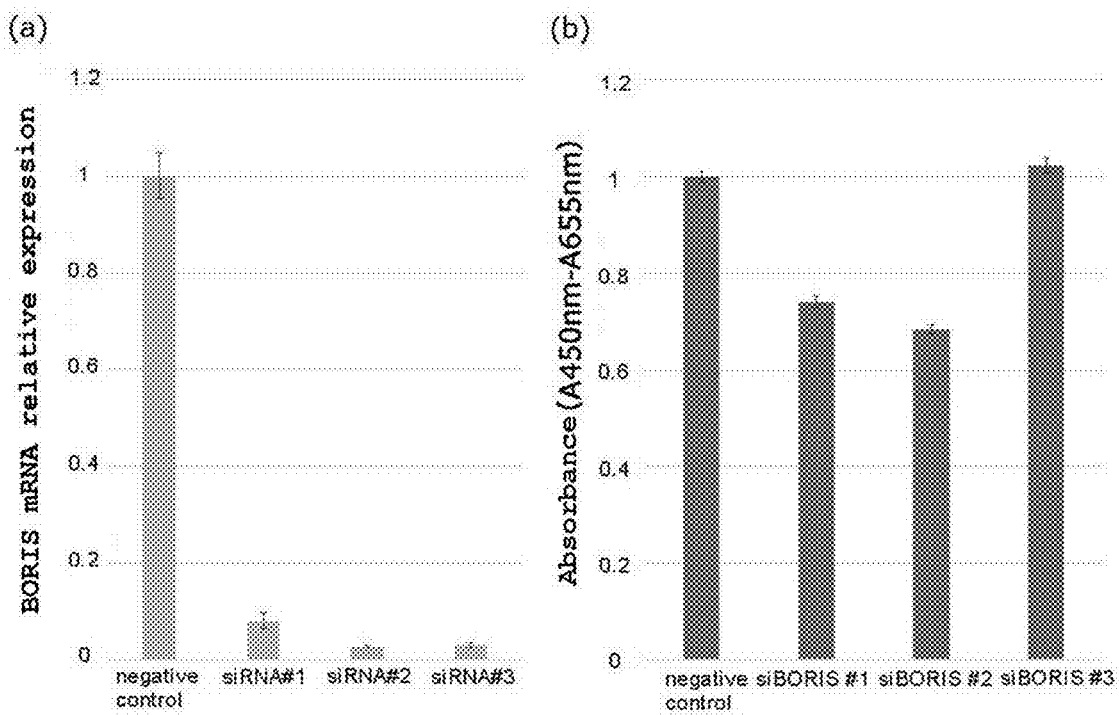

[Fig. 14-2]
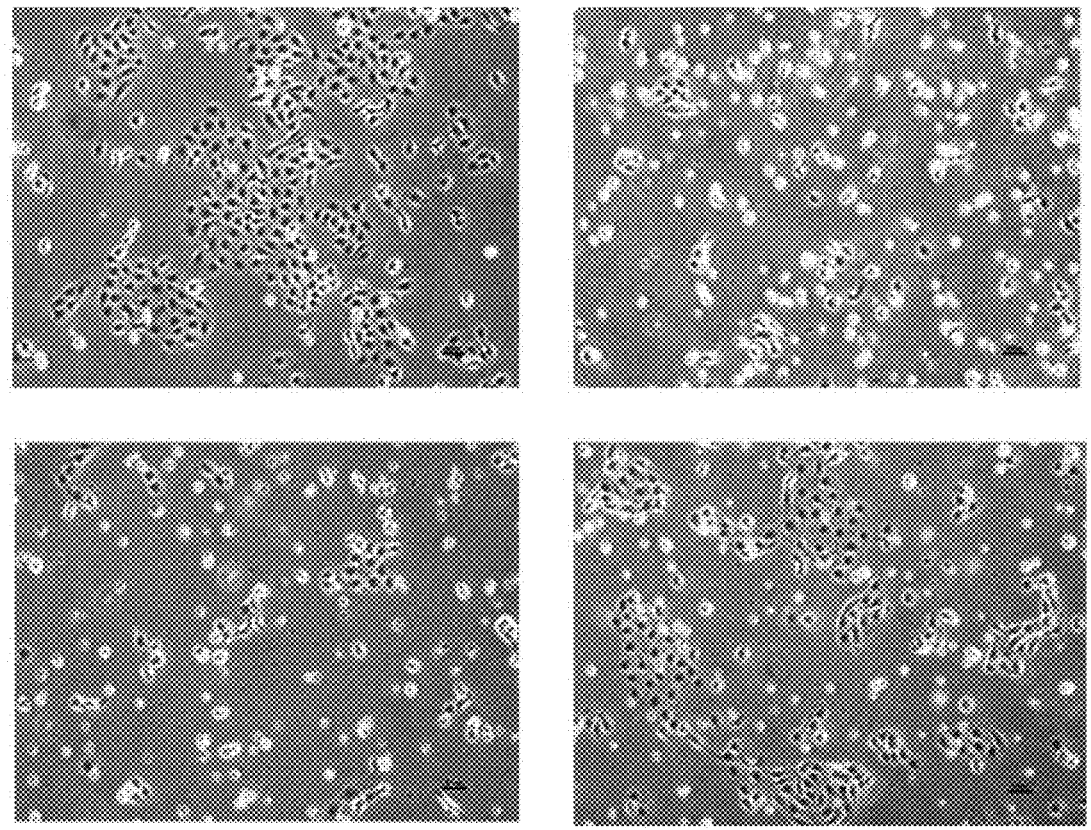
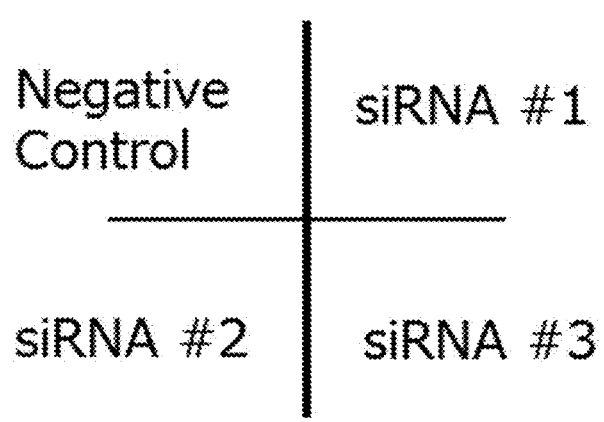

[Fig. 15]
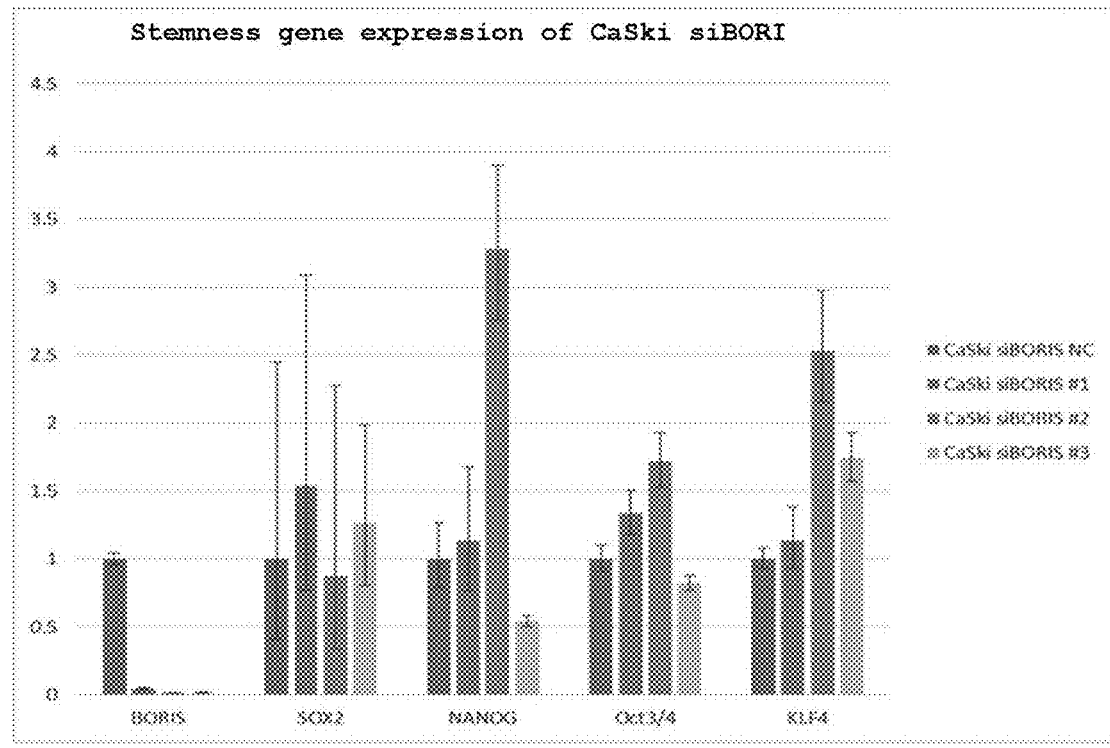
[Fig. 16-1]
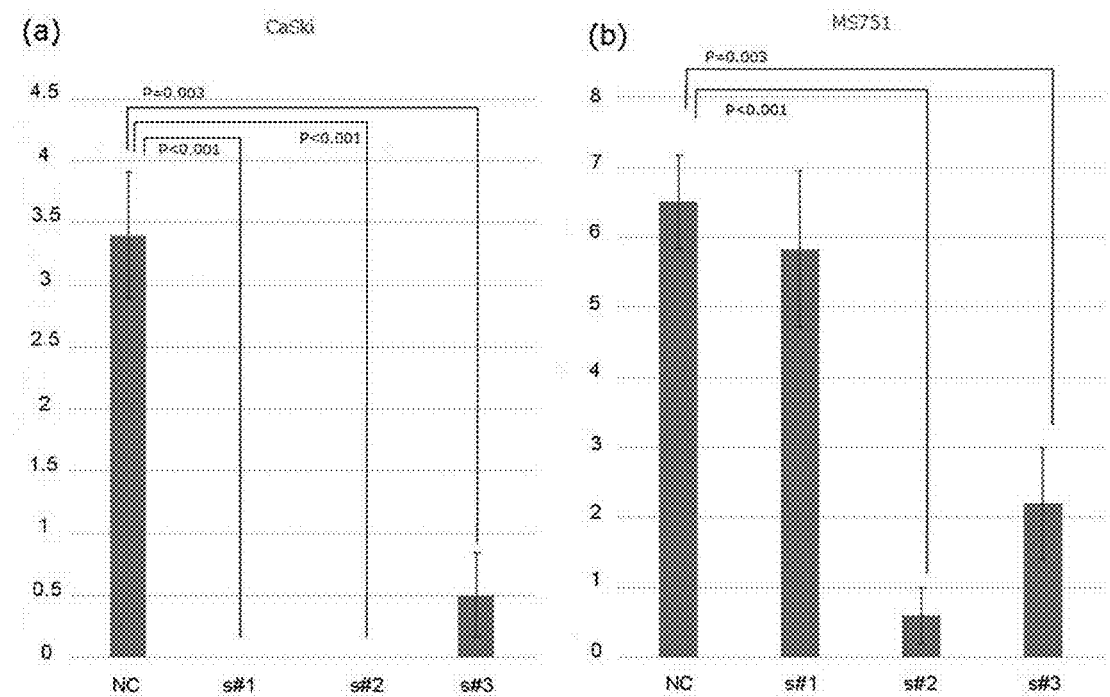

[Fig. 16-2]
CaSki
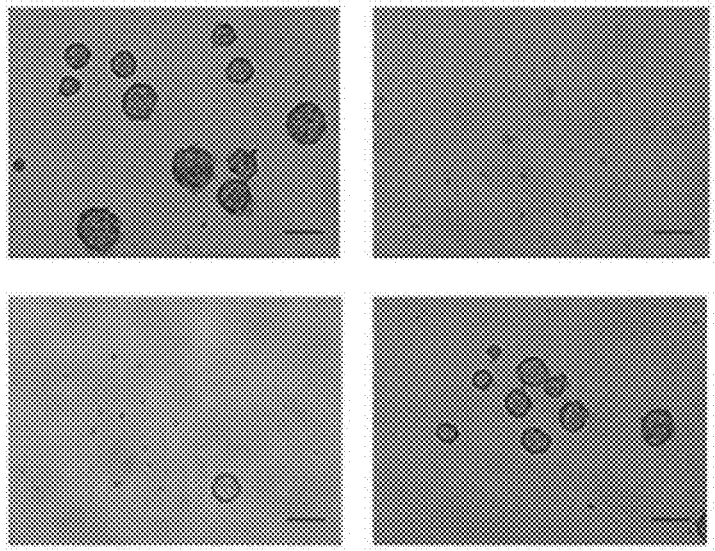
MS751
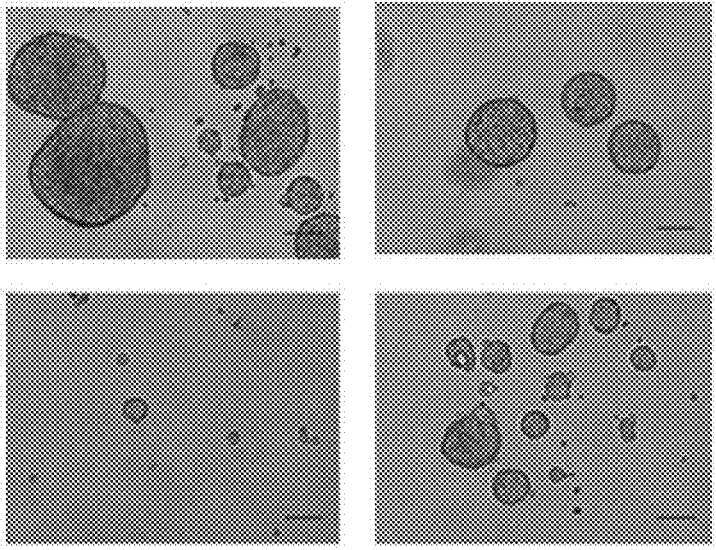
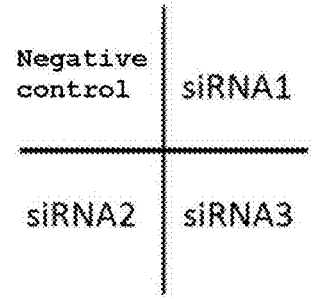
Black bar: 100μm

[Fig. 17]
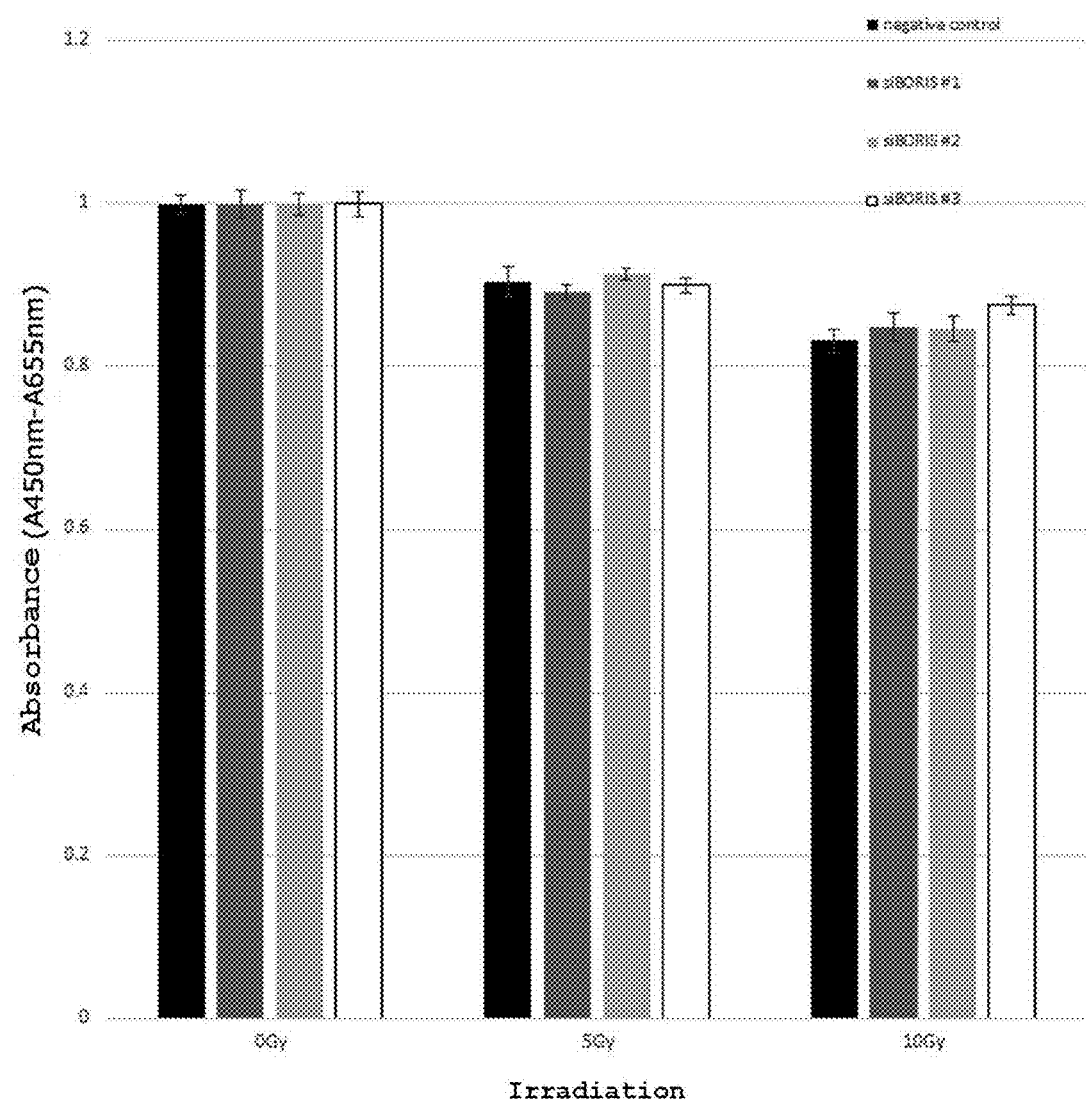

[Fig. 18]
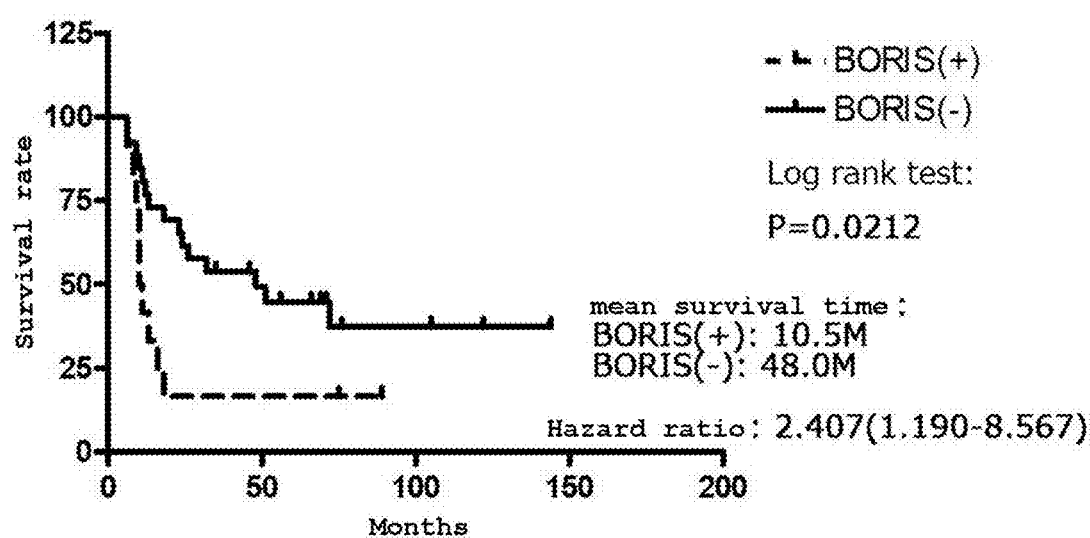

[Fig. 19-1]
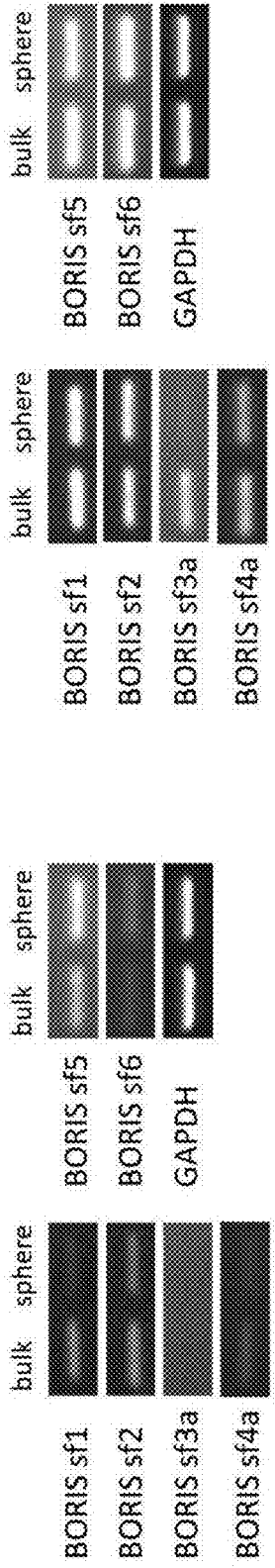
Expression of BORIS subfamilies in bulk cells and sphere cells in small cell lung cancer cell lines
Small cell lung cancer

[Fig. 19-2]
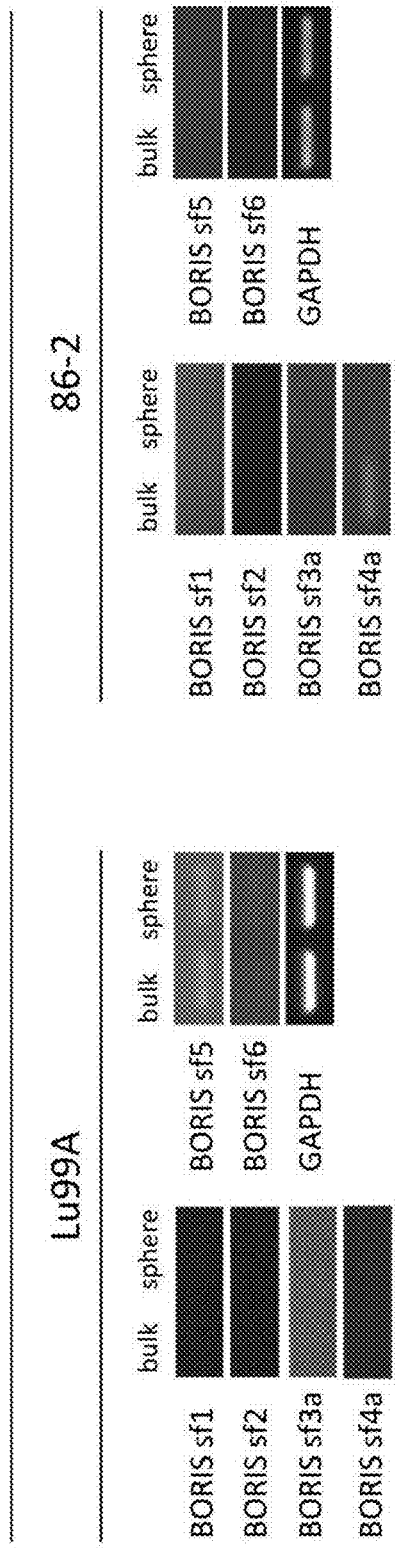

[Fig. 19-3]
Expression of BORIS subfamilies in bulk cells and sphere cells in lung squamous cancer cell lines
Lung squamous cancer
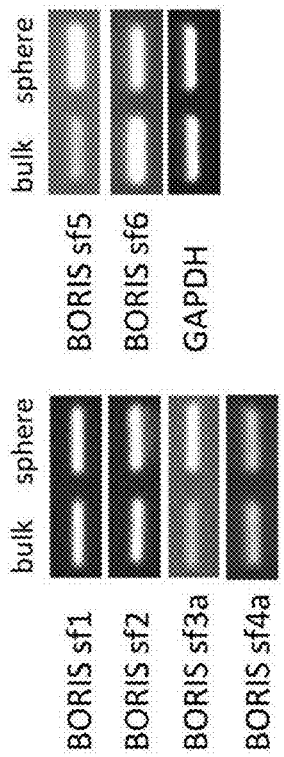
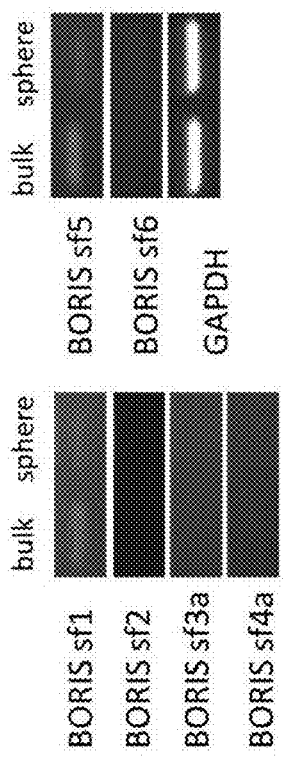
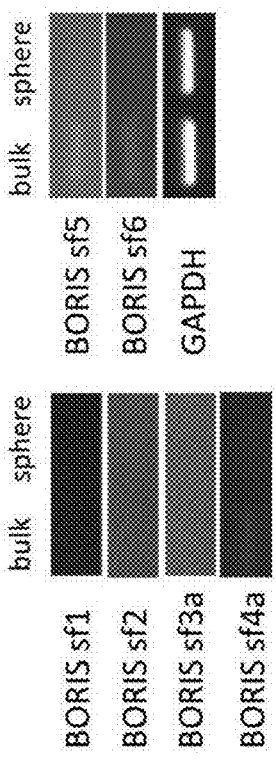

[Fig. 19-4]
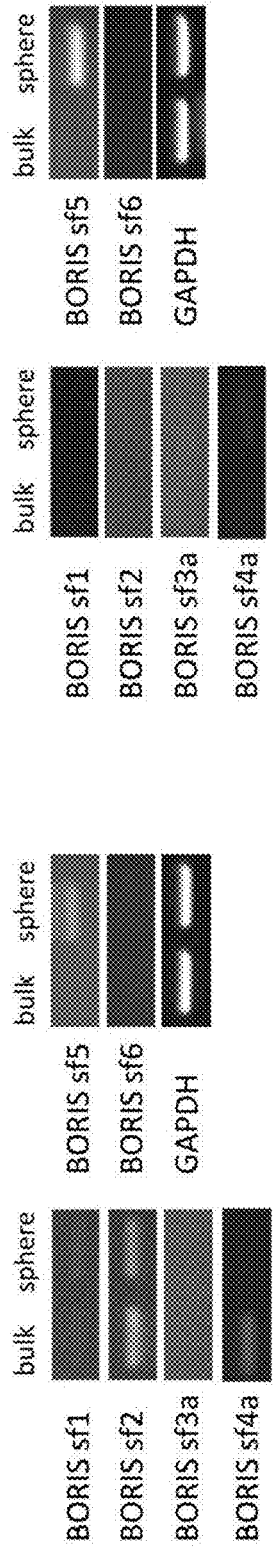

[Fig. 19-5]
Expression of BORIS subfamilies in bulk cells and sphere cells in lung adenocarcinoma primary cultured cells
Lung adenocarcinoma primary cultured cells
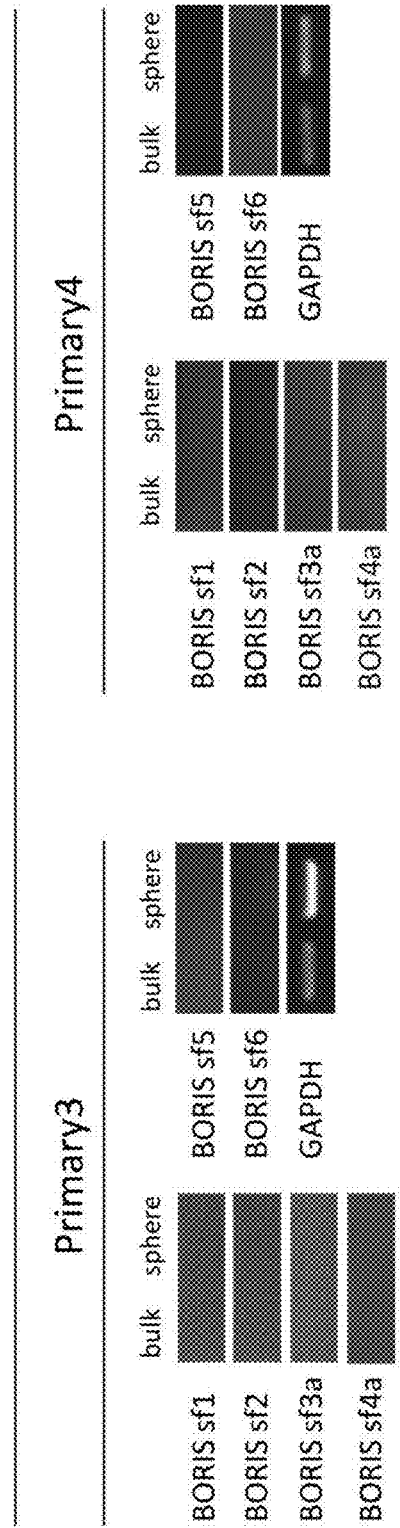
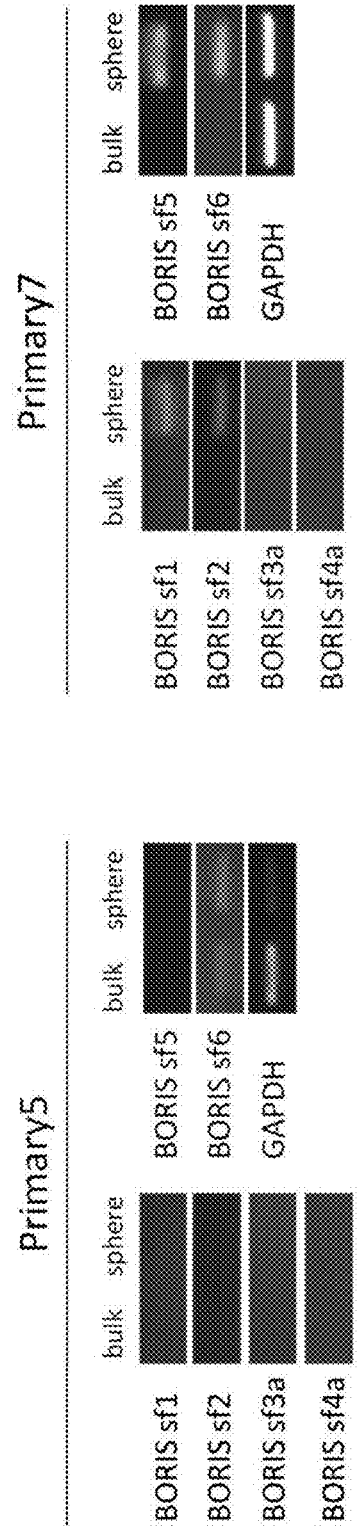

[Fig. 20]
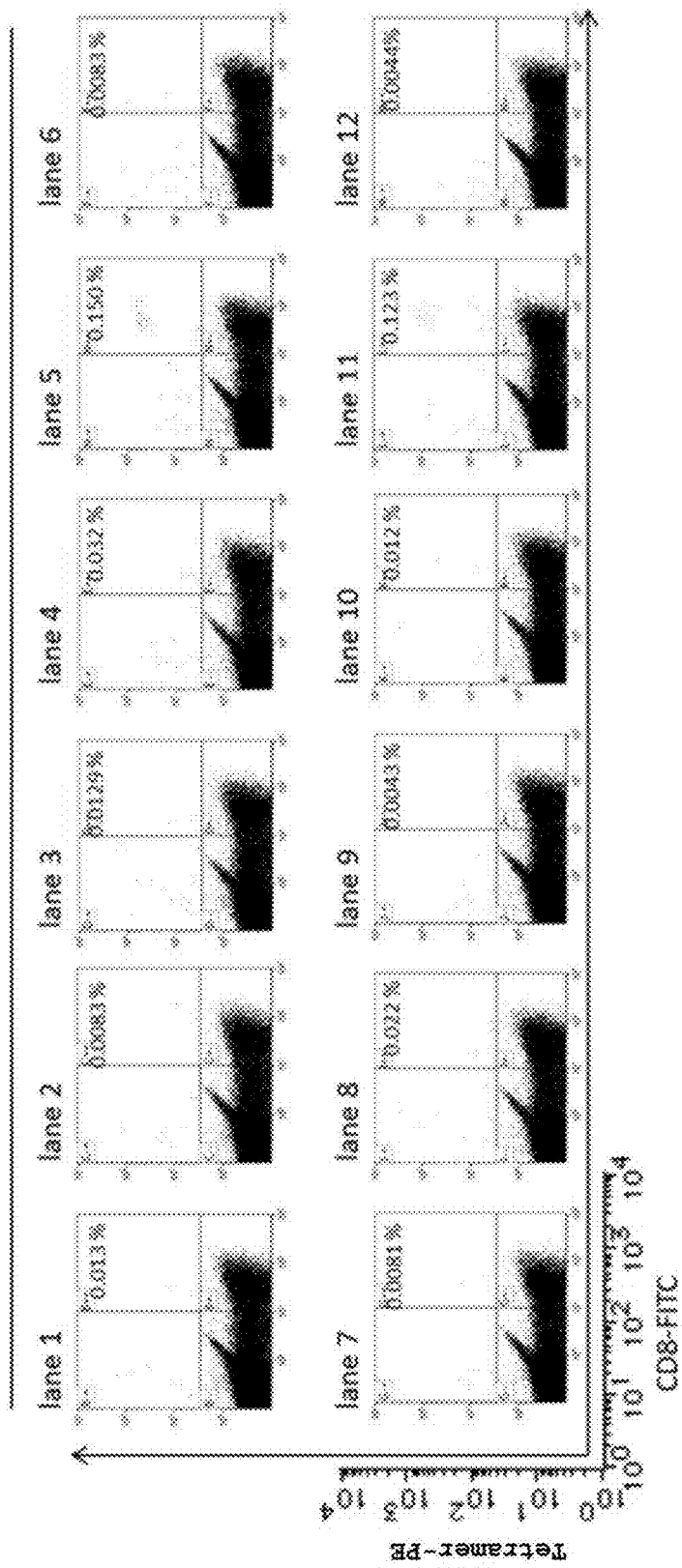

[Fig. 21]
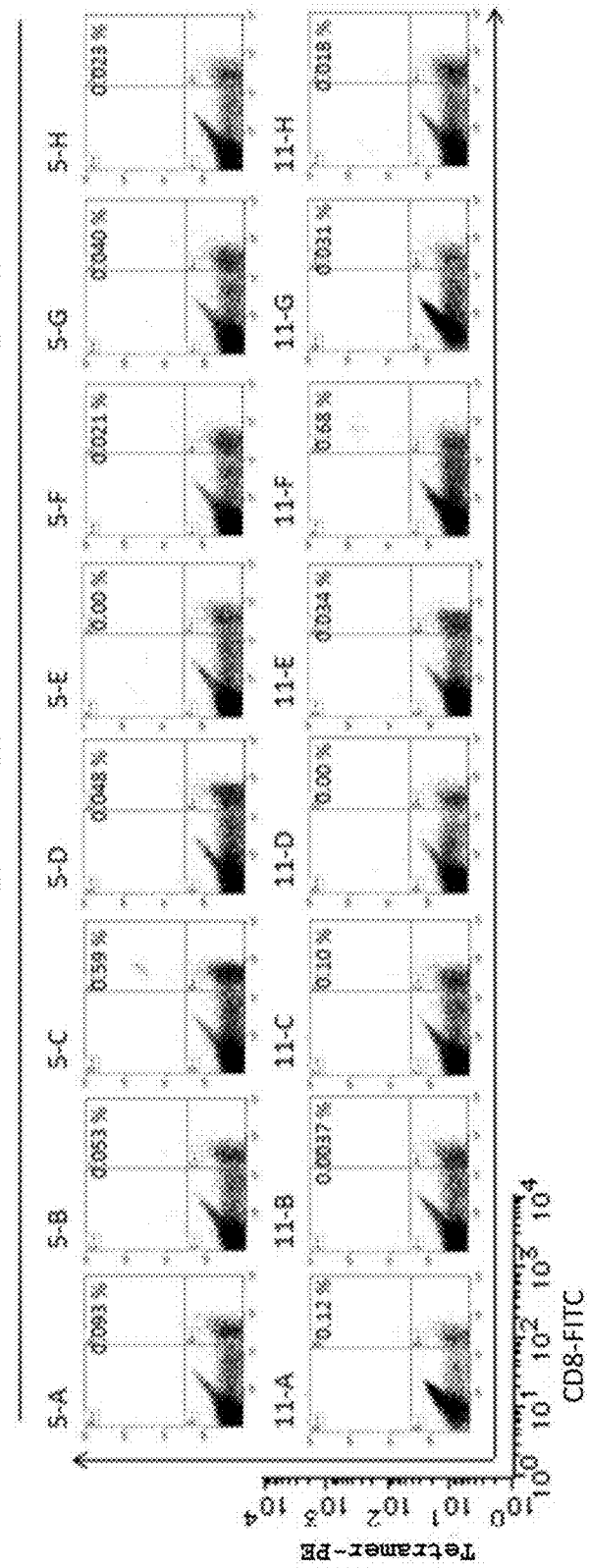

[Fig. 22]
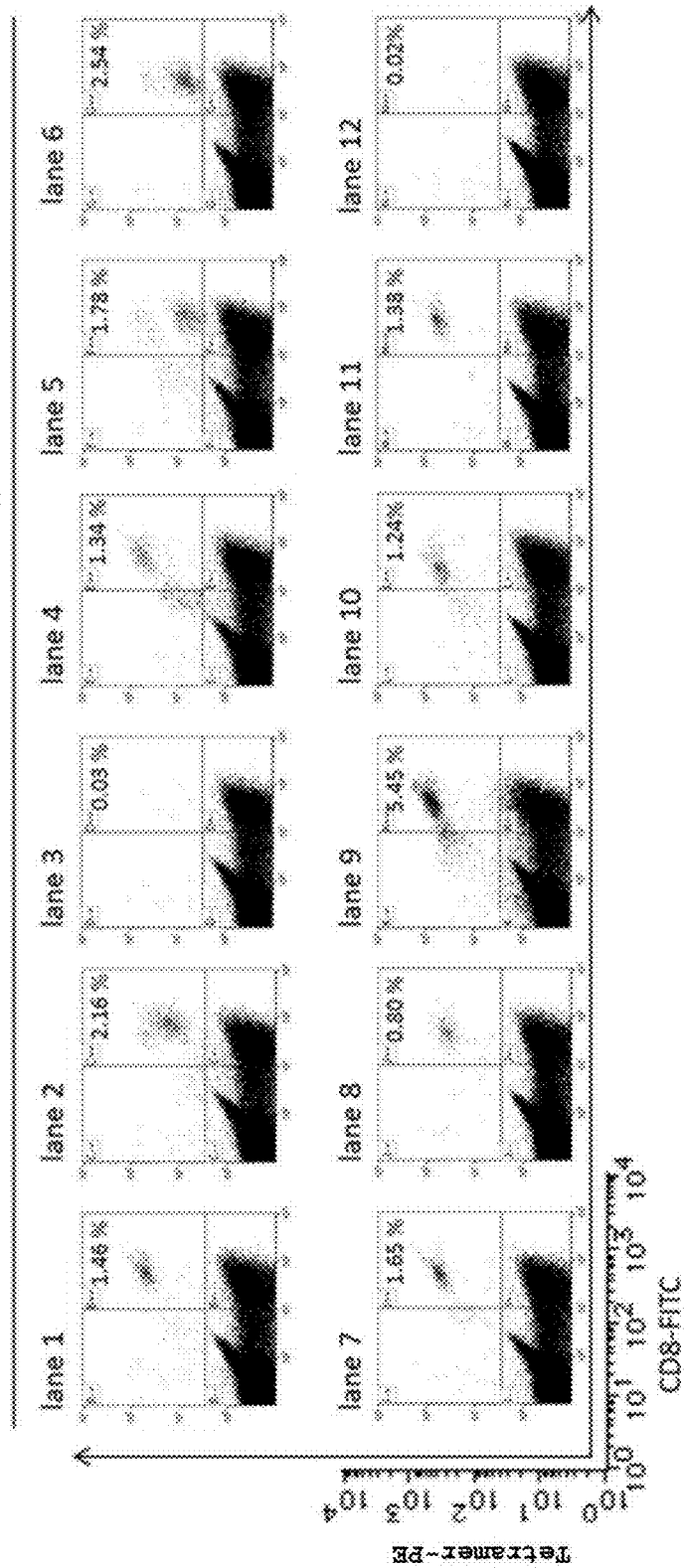

[Fig. 23-1]
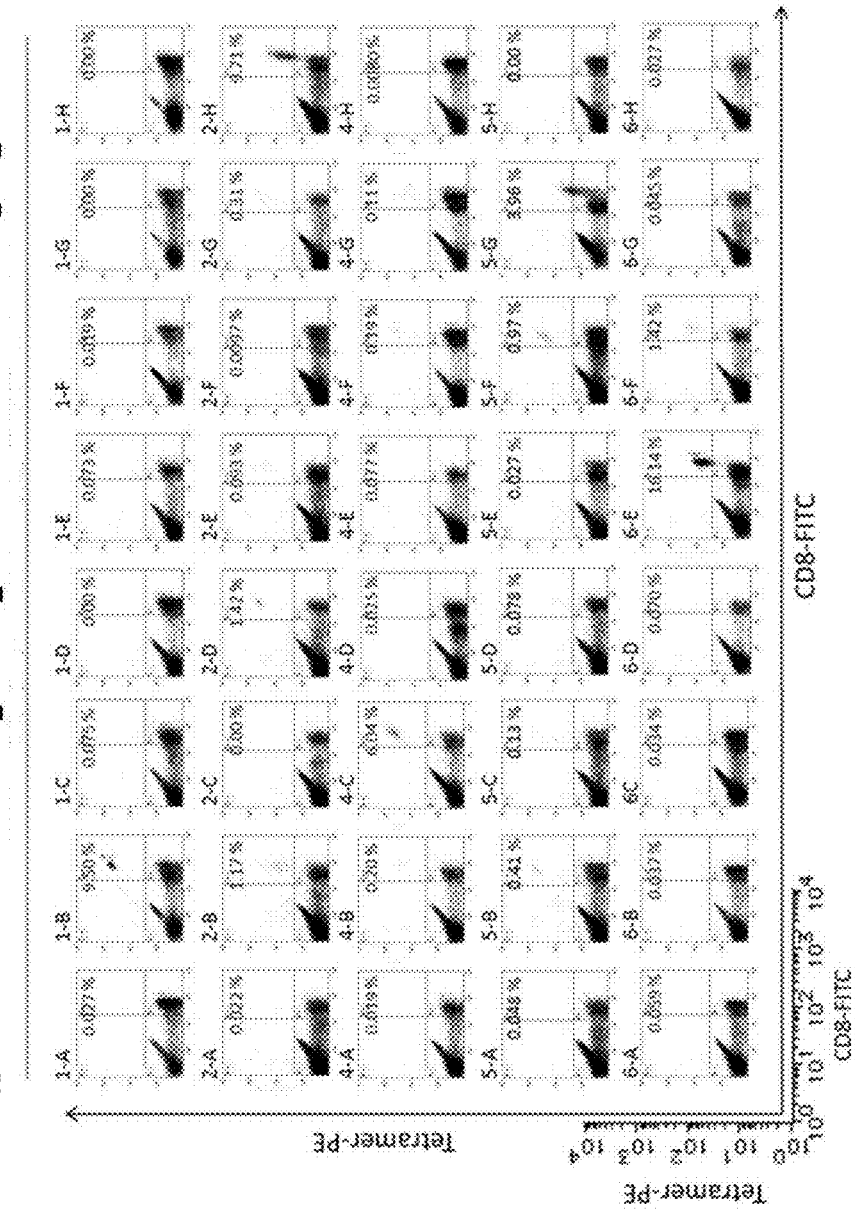

[Fig. 23-2]
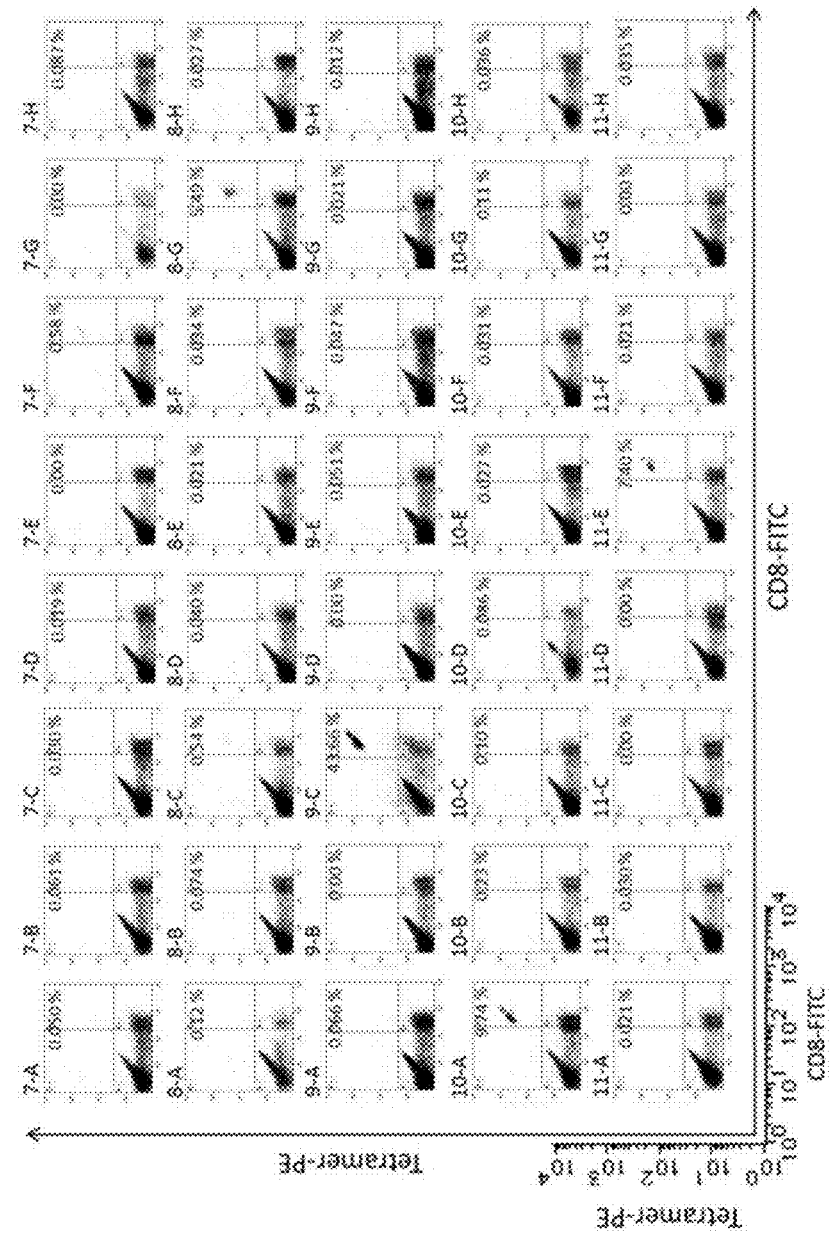

[Fig. 24]
Result of induction of BORIS-specific CTL (sample: A2-S1)
Sample: A2-S1
SEQ ID No: 5 epitope candidate peptide
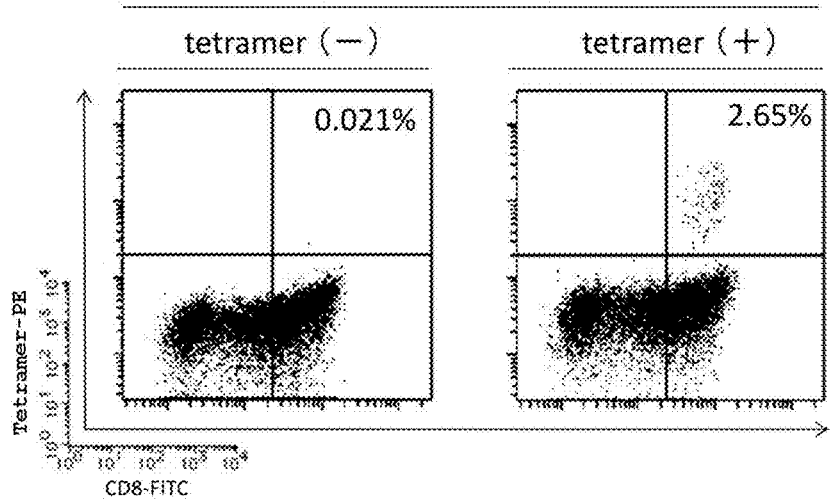
[Fig. 25]
BORIS-specific CTL cell IFNγ ELISPOT assay
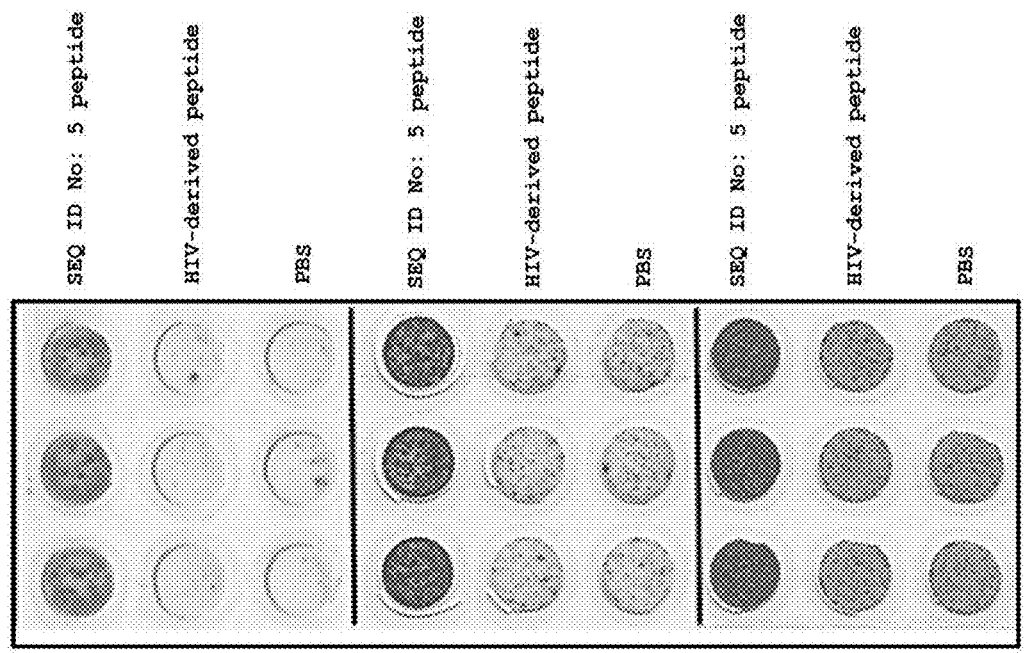

[Fig. 26]
Result of monocloning of BORIS-specific CTL
(sample: A2-S1)
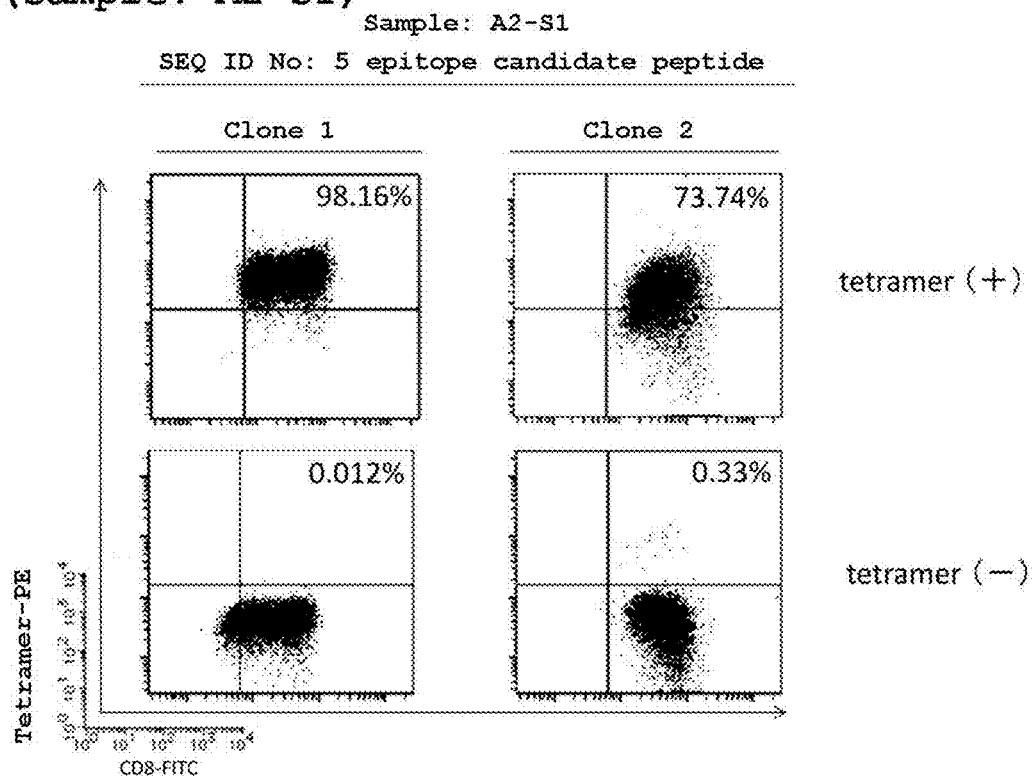
[Fig. 27]
IFNγ ELISPOT assay for BORIS-specific CTL cell
(Sample: A2-S1)
SEQ ID No: 5 peptide
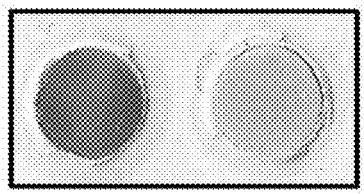
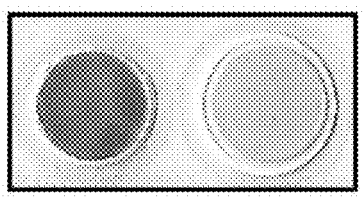

[Fig. 28]
Functional analysis of BORIS-specific CTL (LDH killing assay)
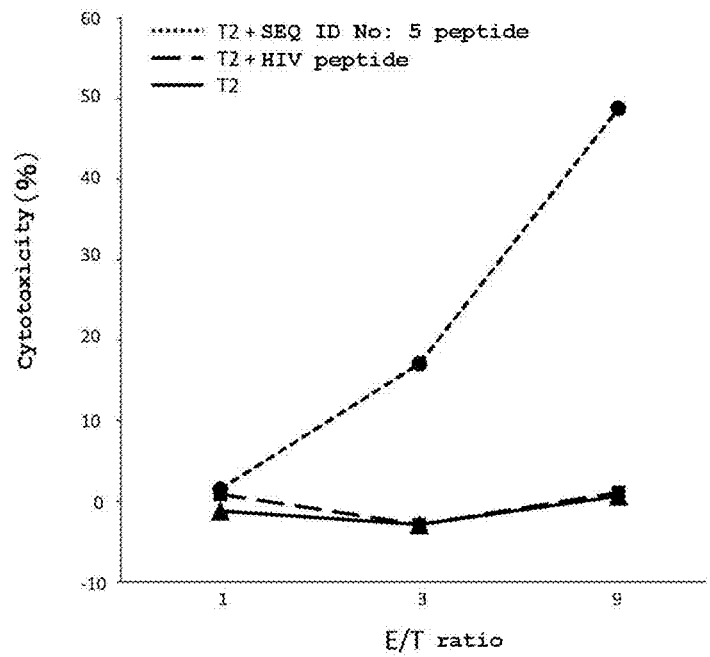
[Fig. 29]
Result of induction of BORIS-specific CTL (sample: A24-S4, A2-S5)
SEQ ID No: 10 epitope candidate peptide
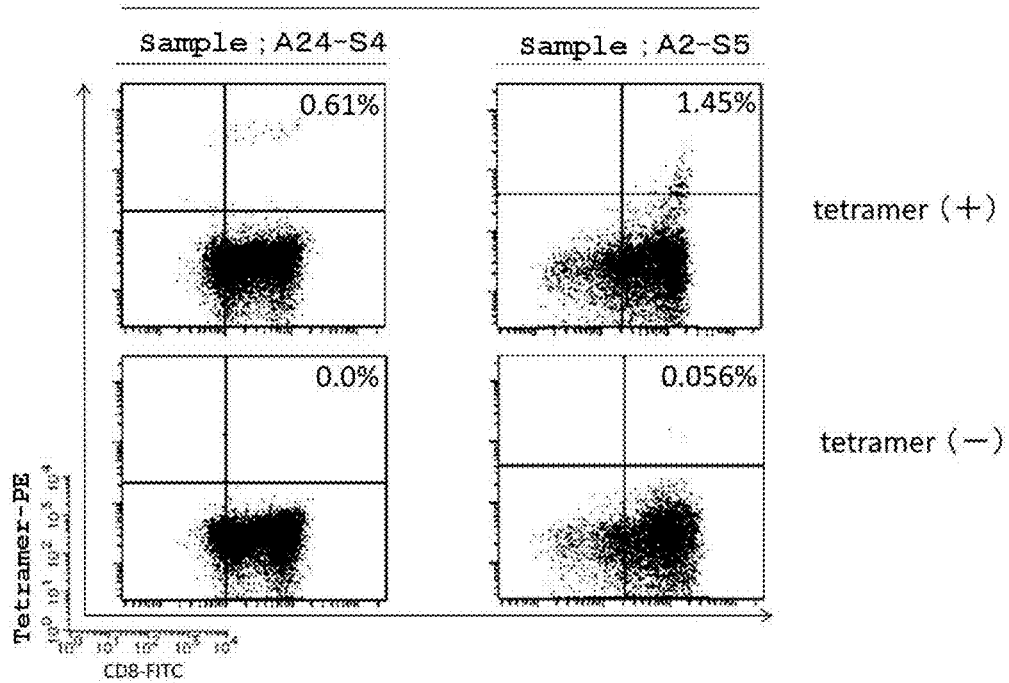

[Fig. 30]
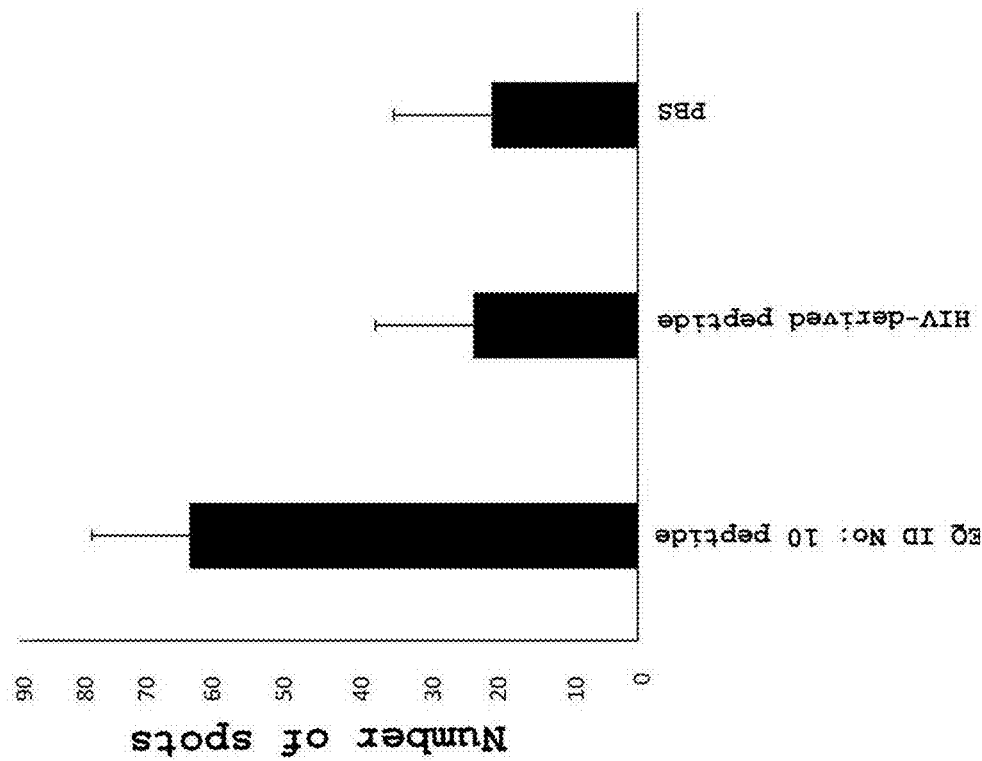
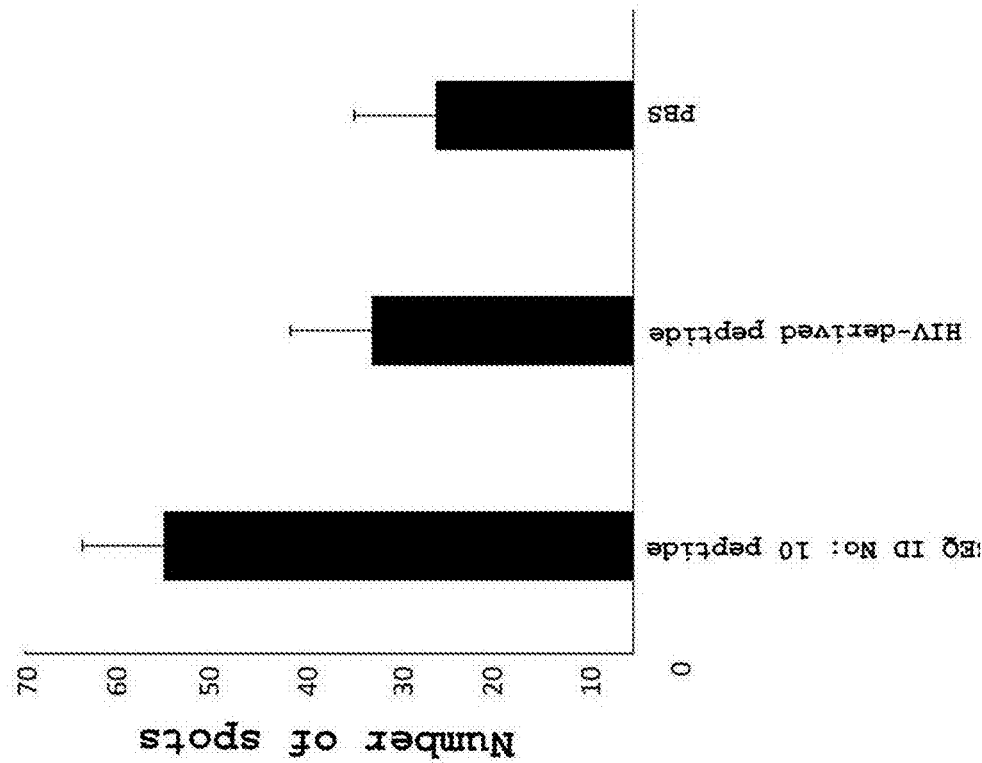

[Fig. 31]
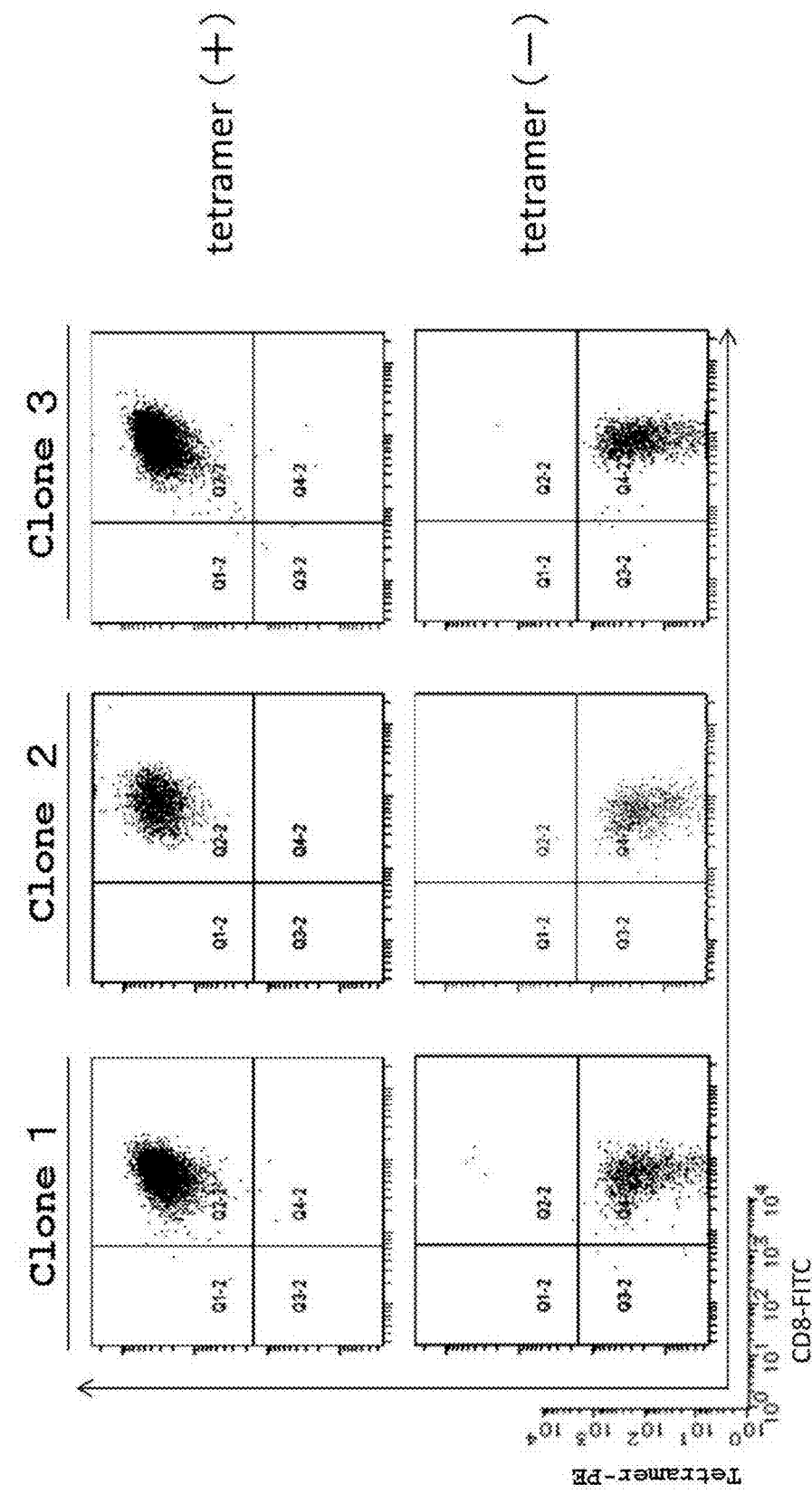

[Fig. 32]
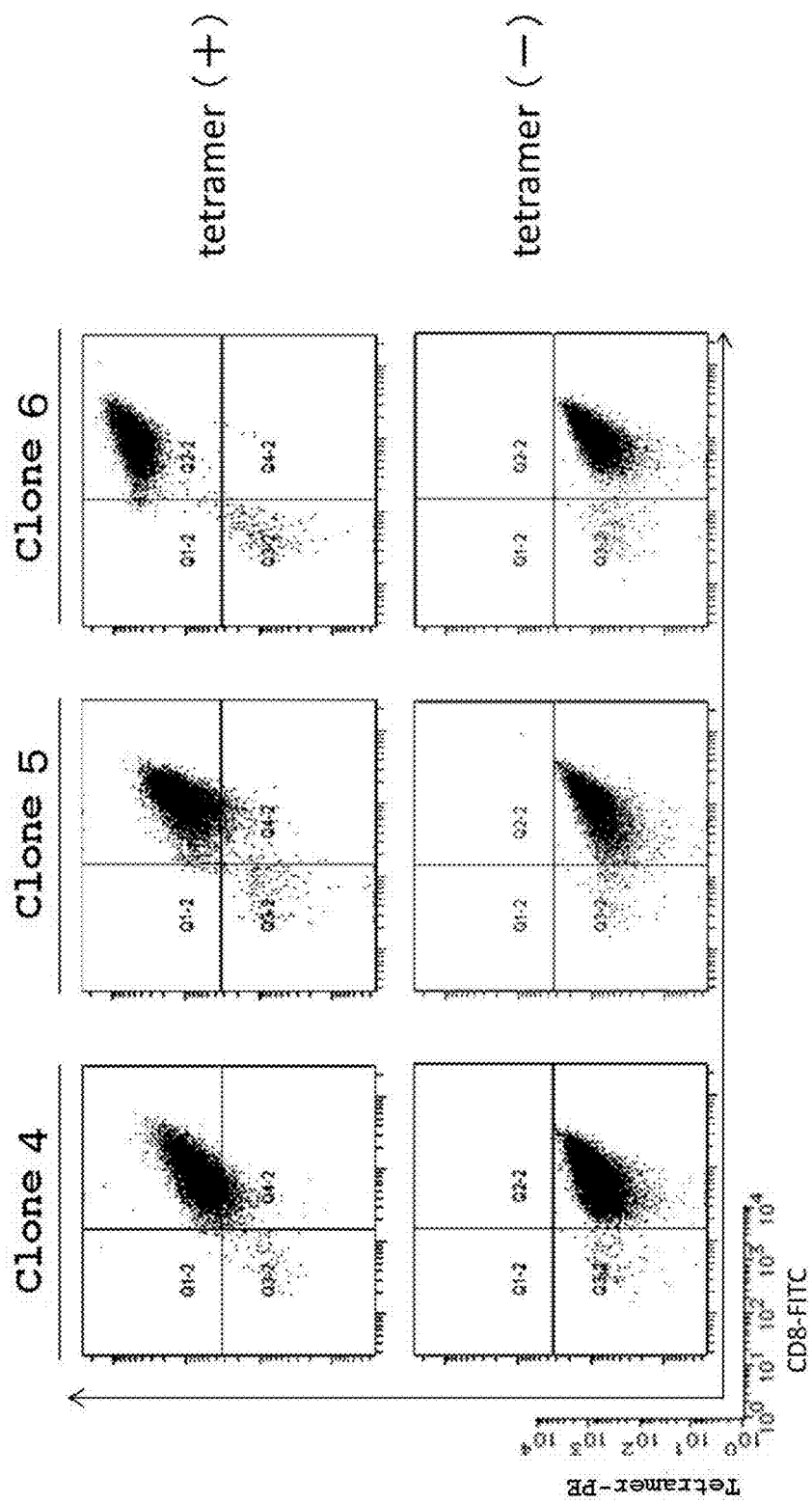

[Fig. 33]
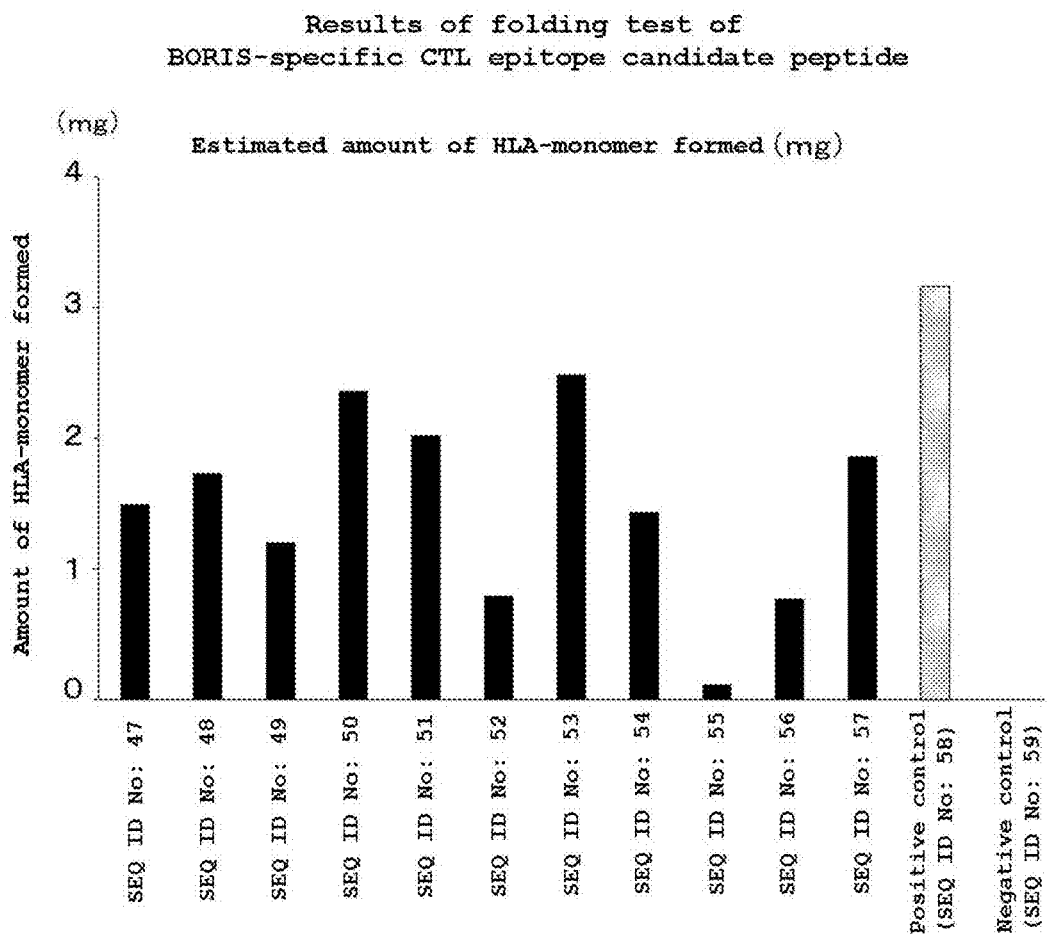

[Fig. 34]
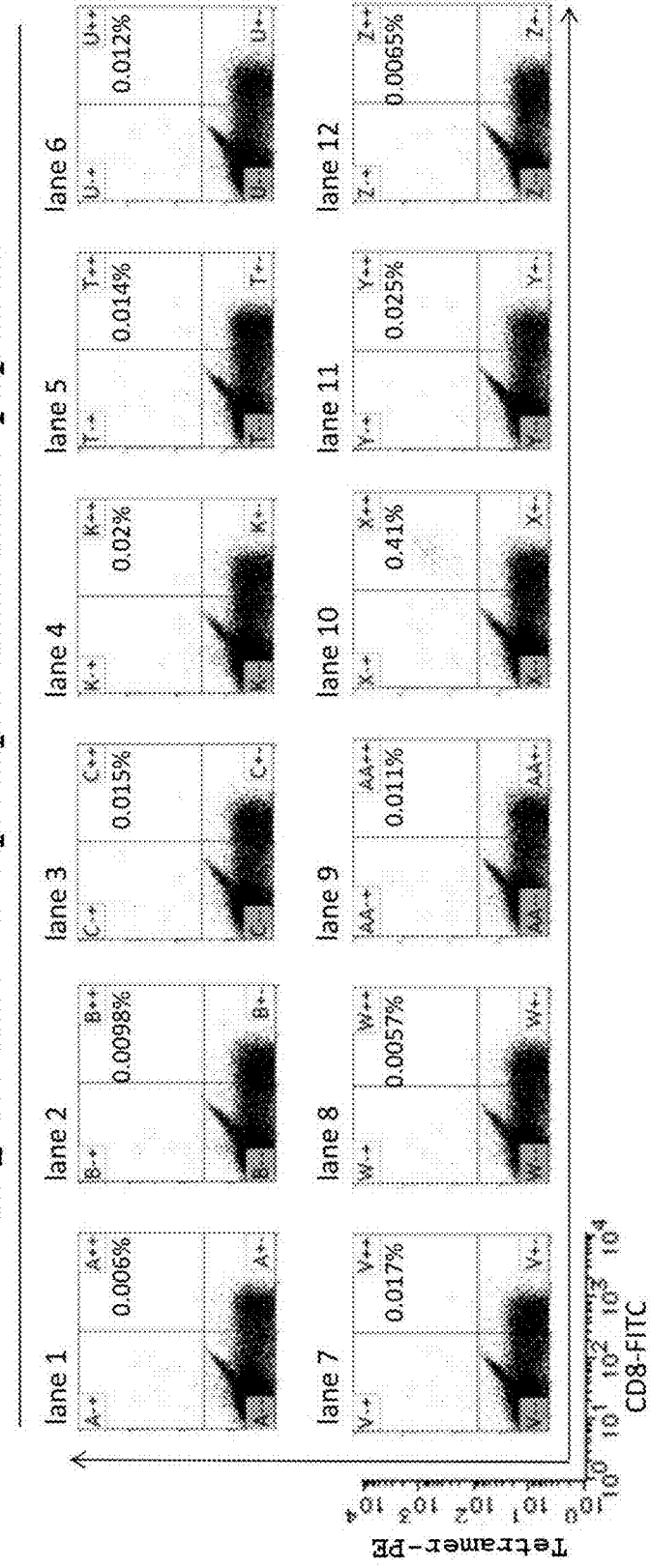

[Fig. 35]
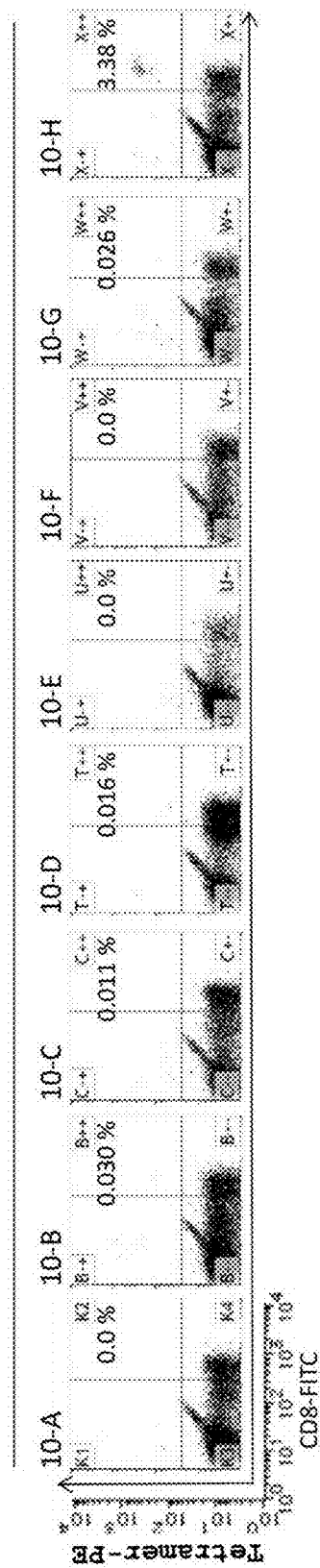

[Fig. 36]
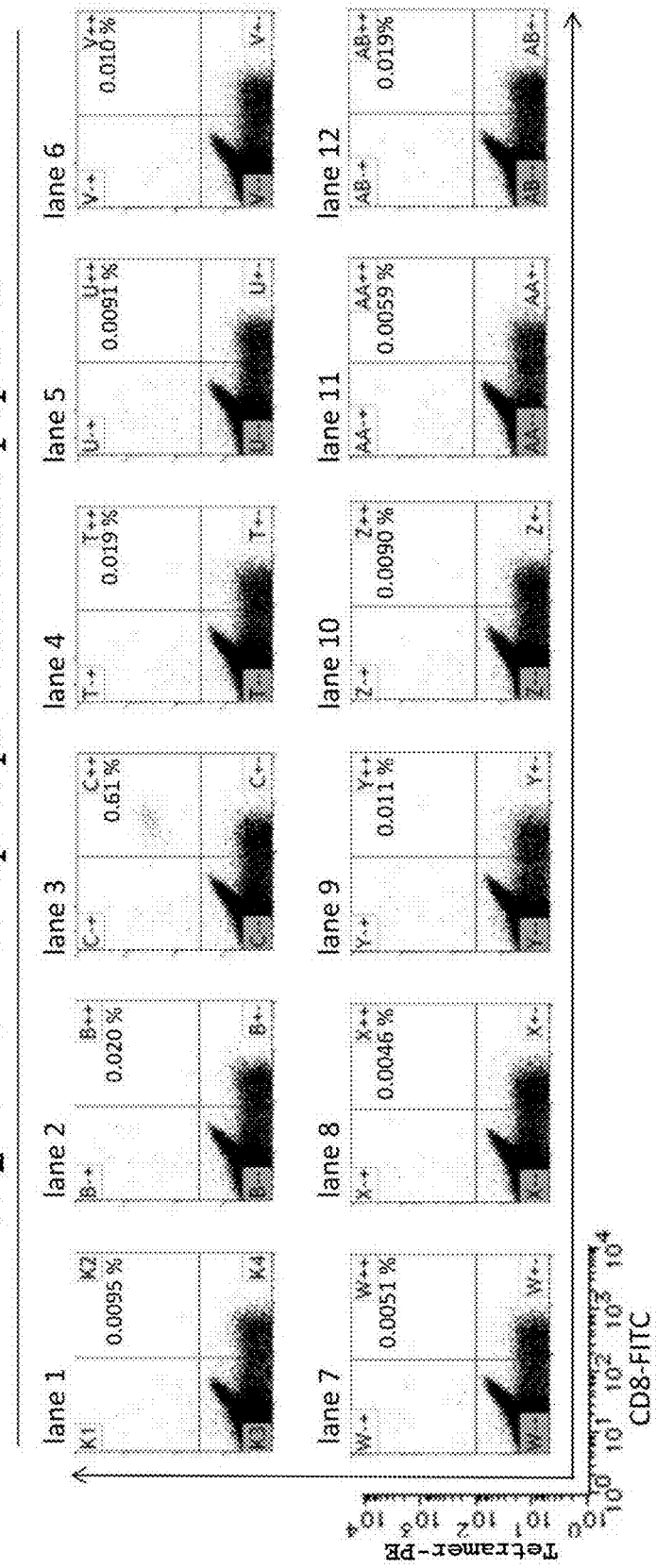

[Fig. 37]
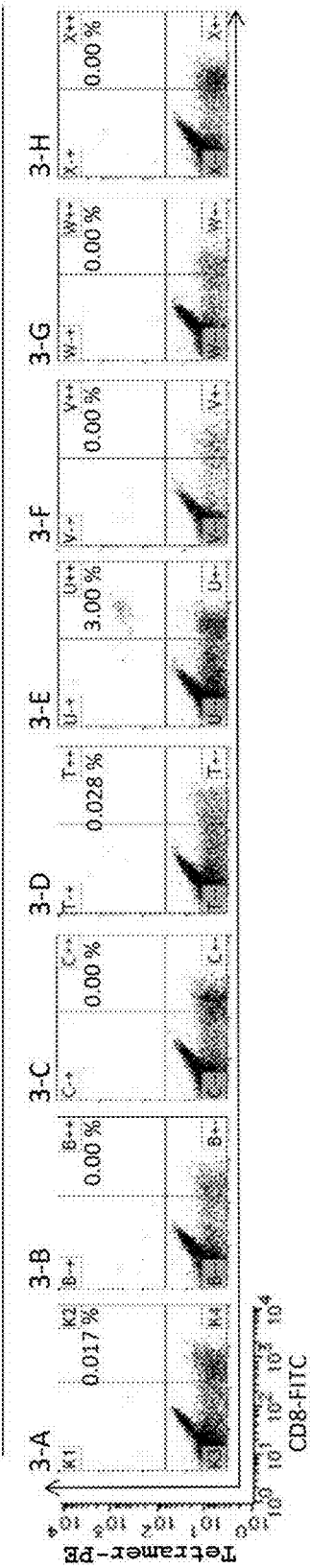

[Fig. 38]
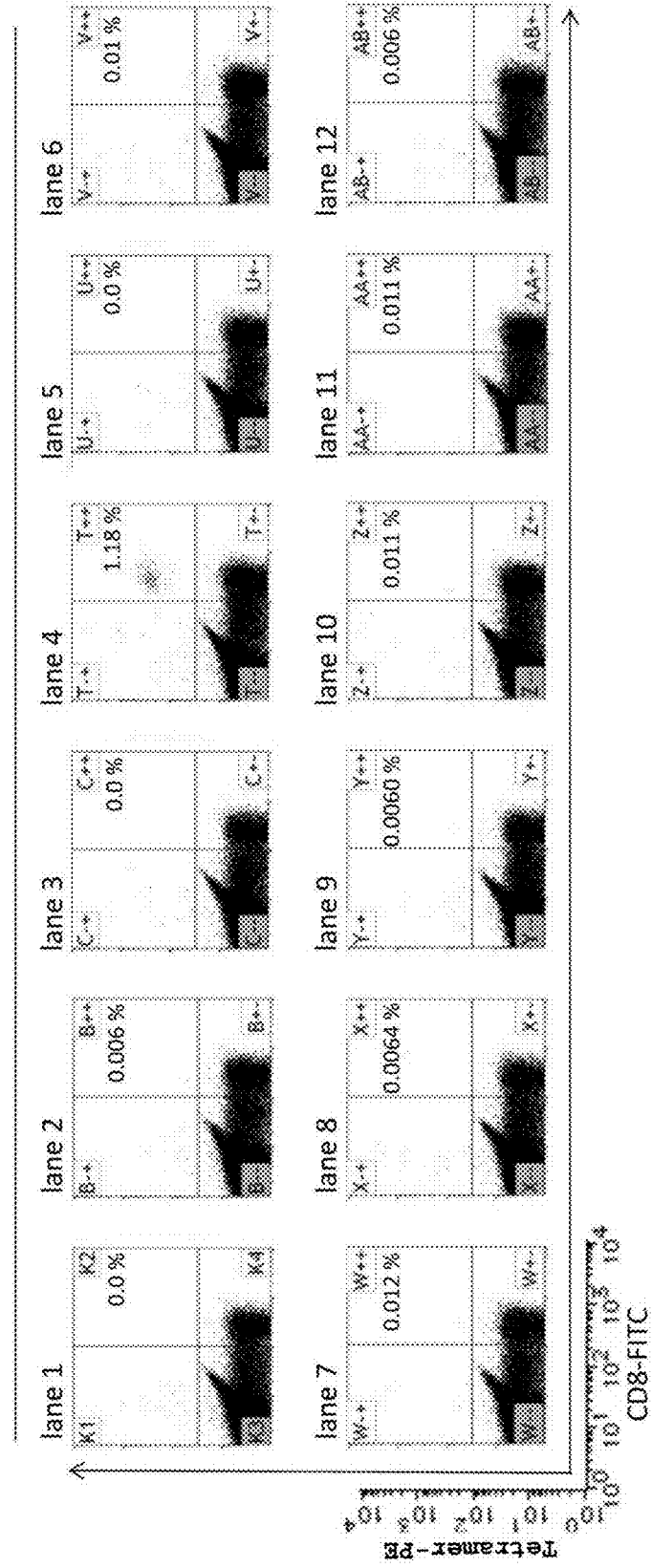

[Fig. 39]
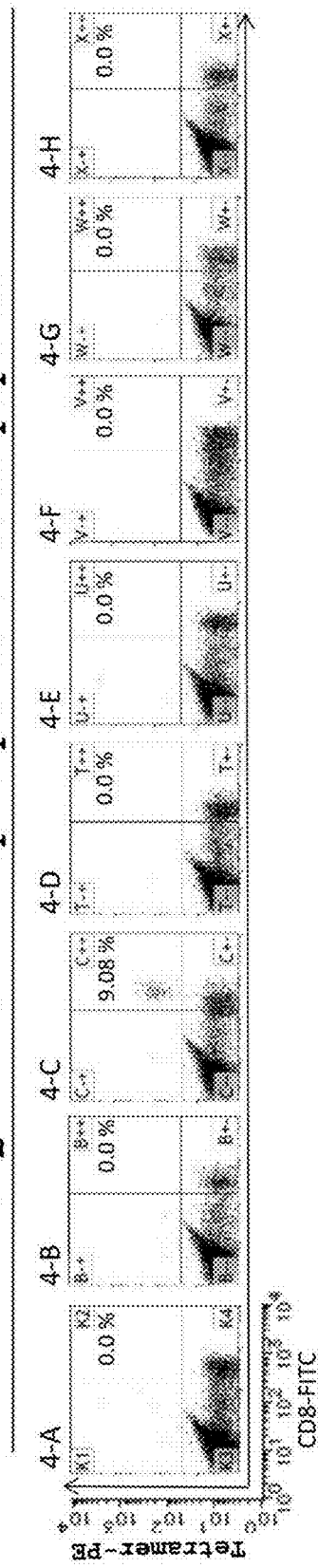

[Fig. 40]
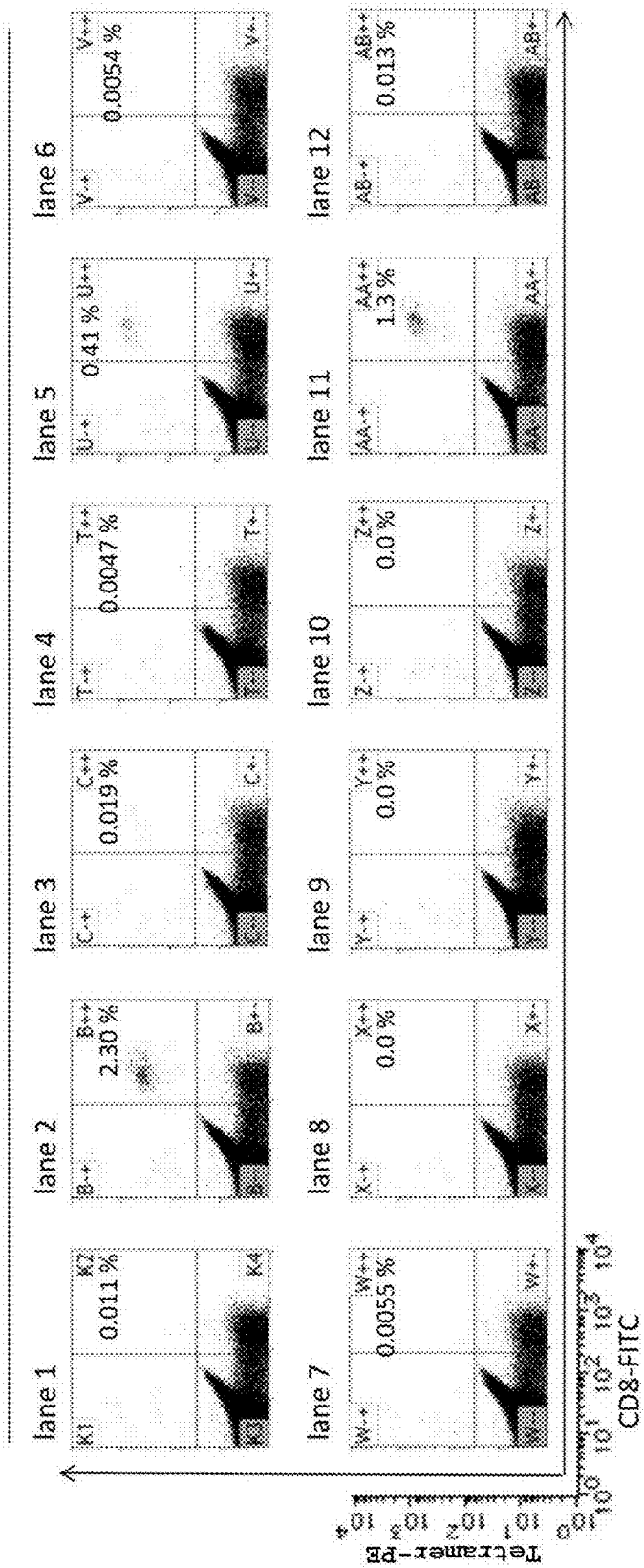

[Fig. 41]
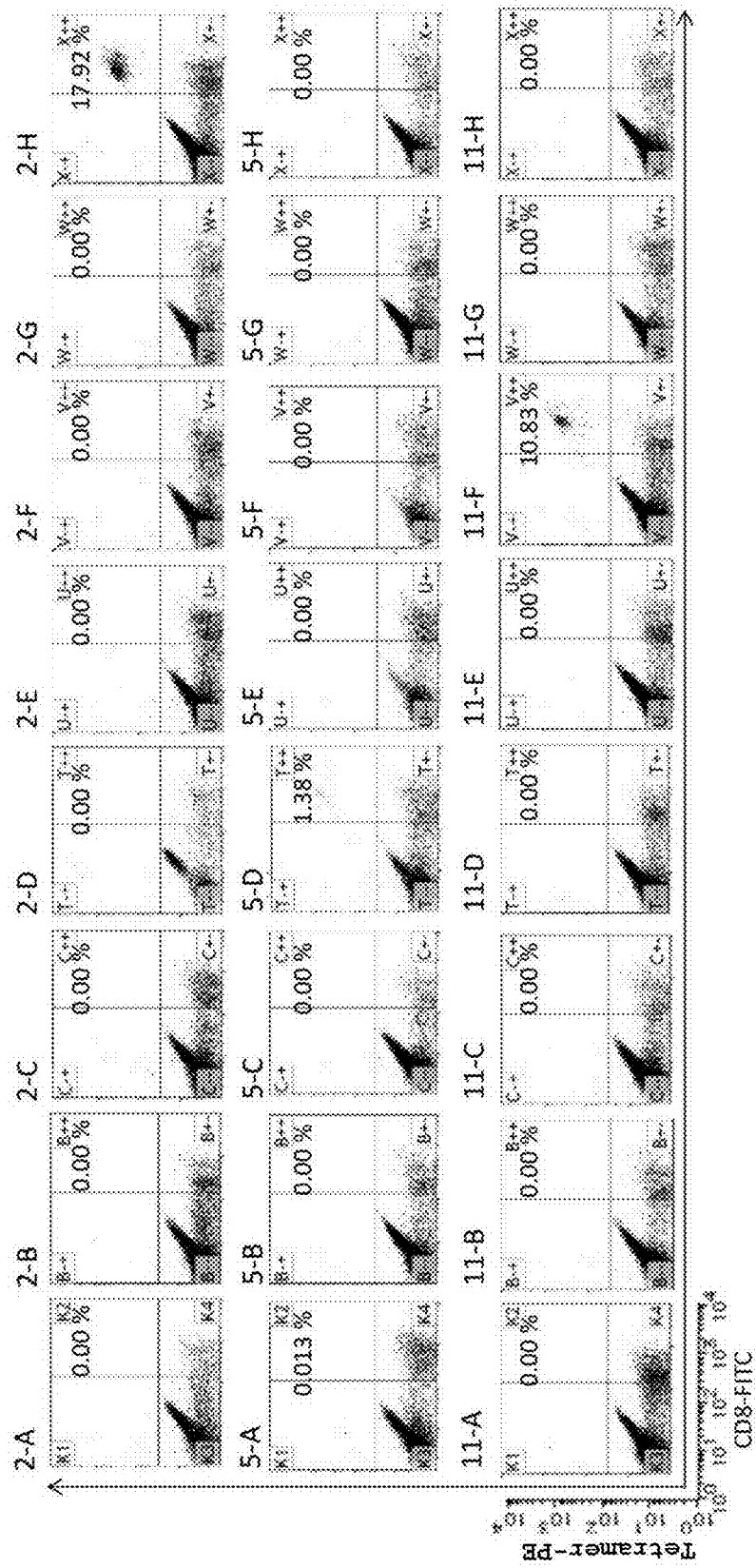

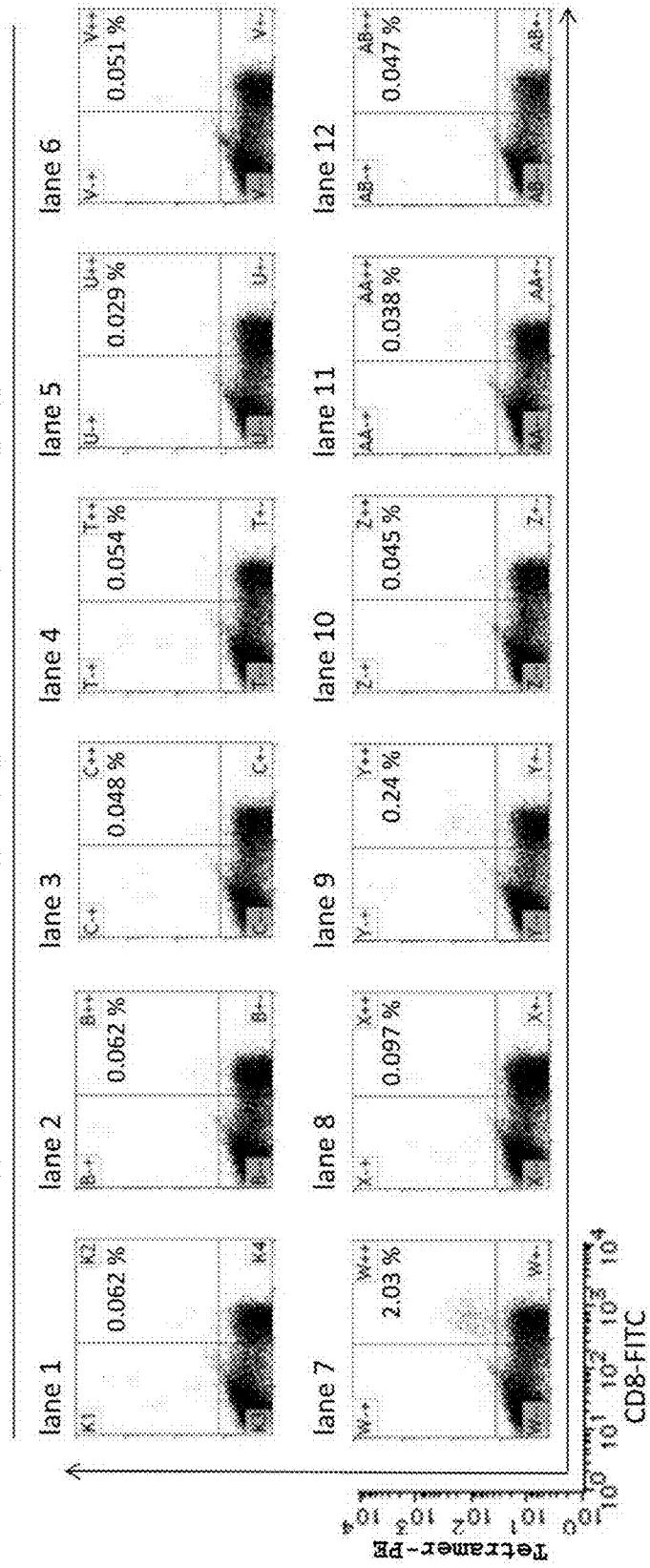
[Fig. 42]

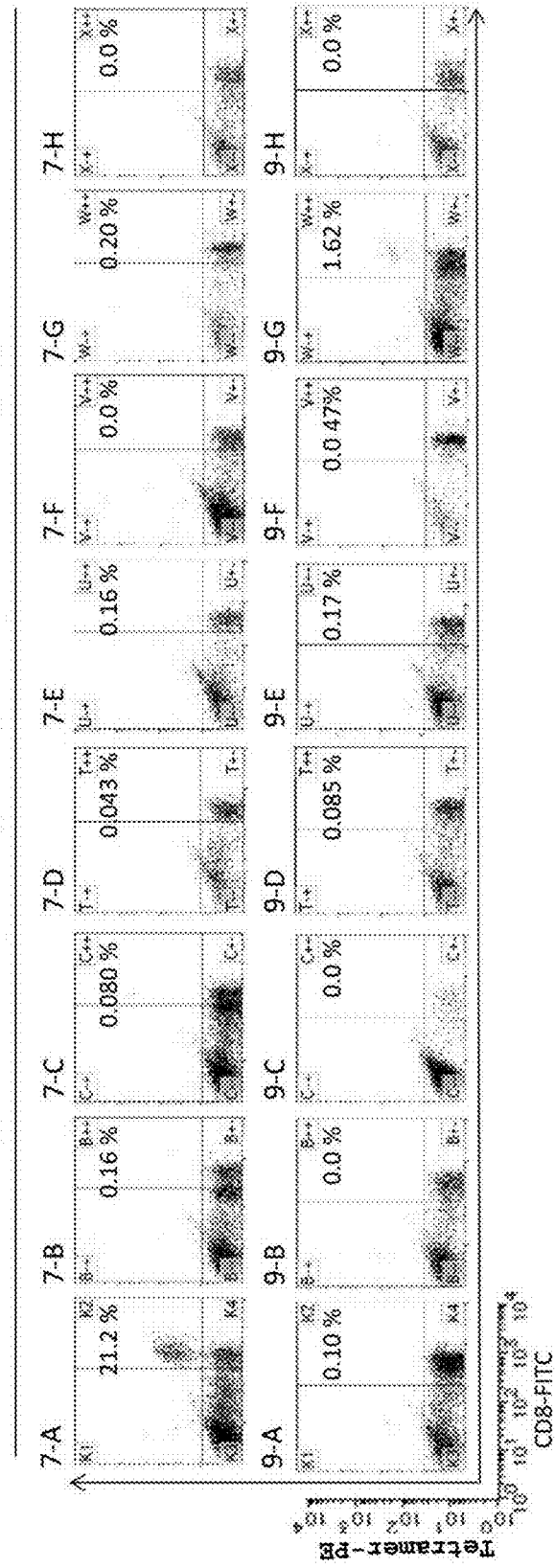
[Fig. 43]

[Fig. 44]
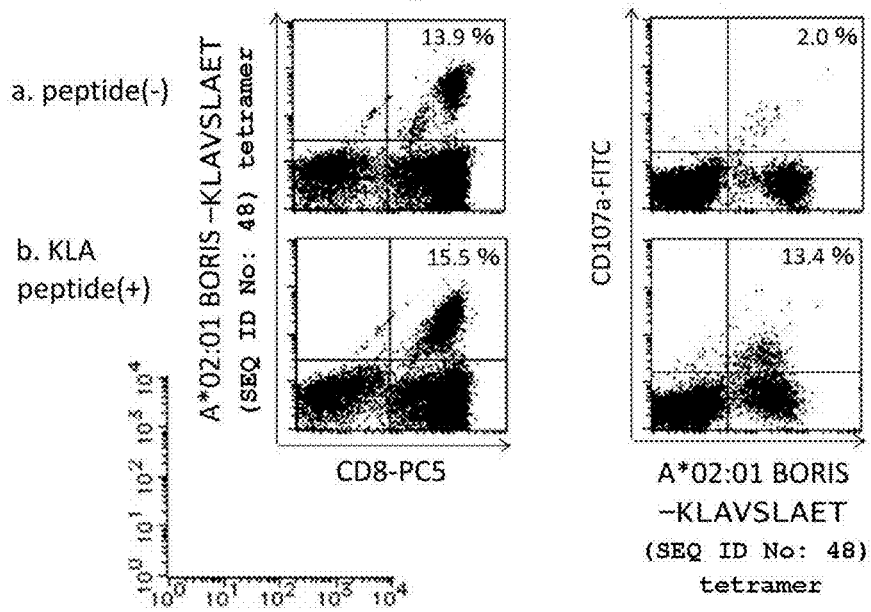
[Fig. 45]
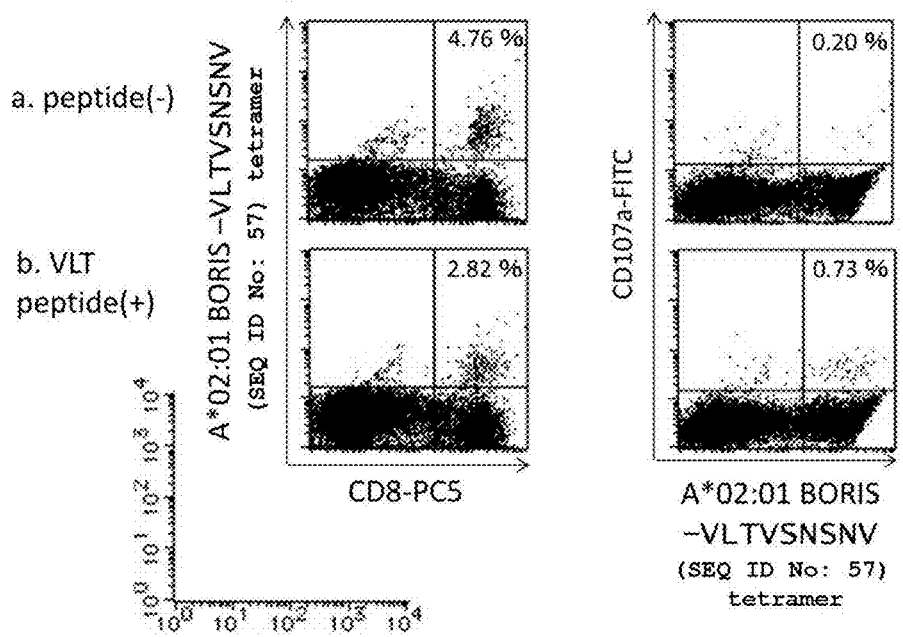

[Fig. 46]
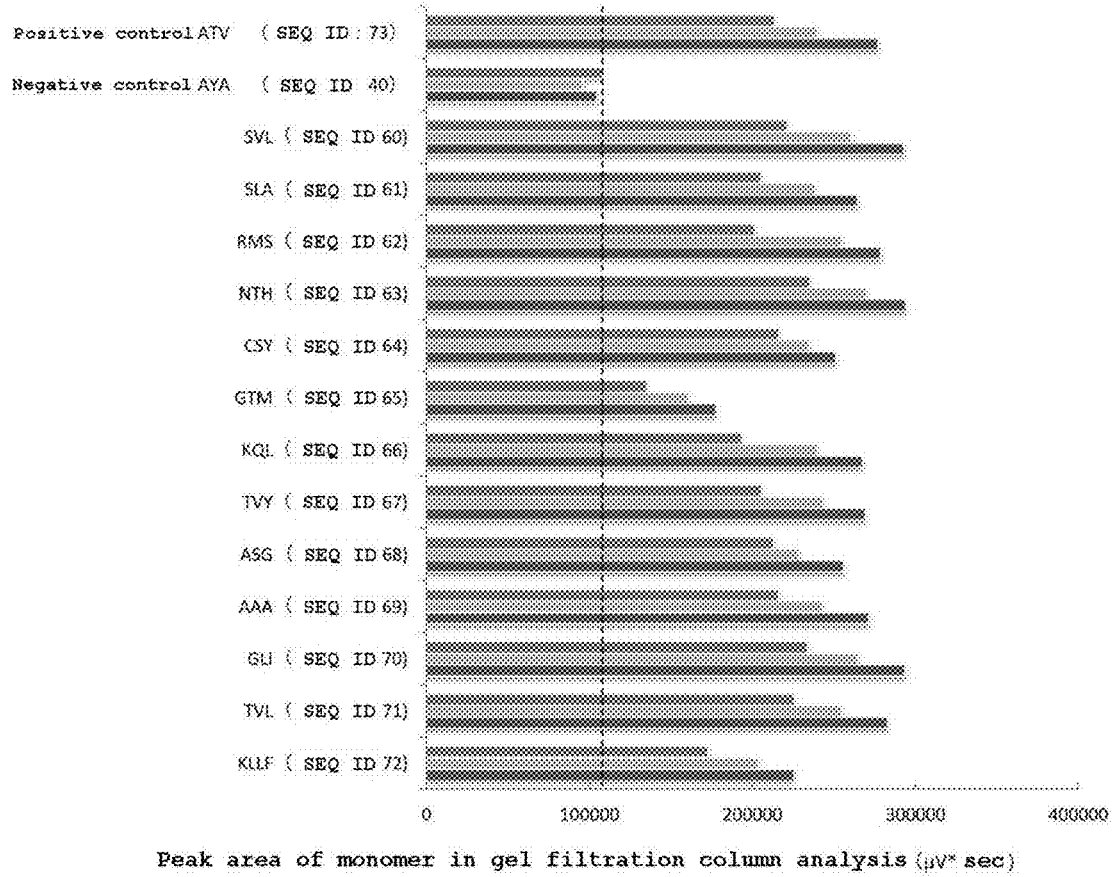

[Fig. 47]
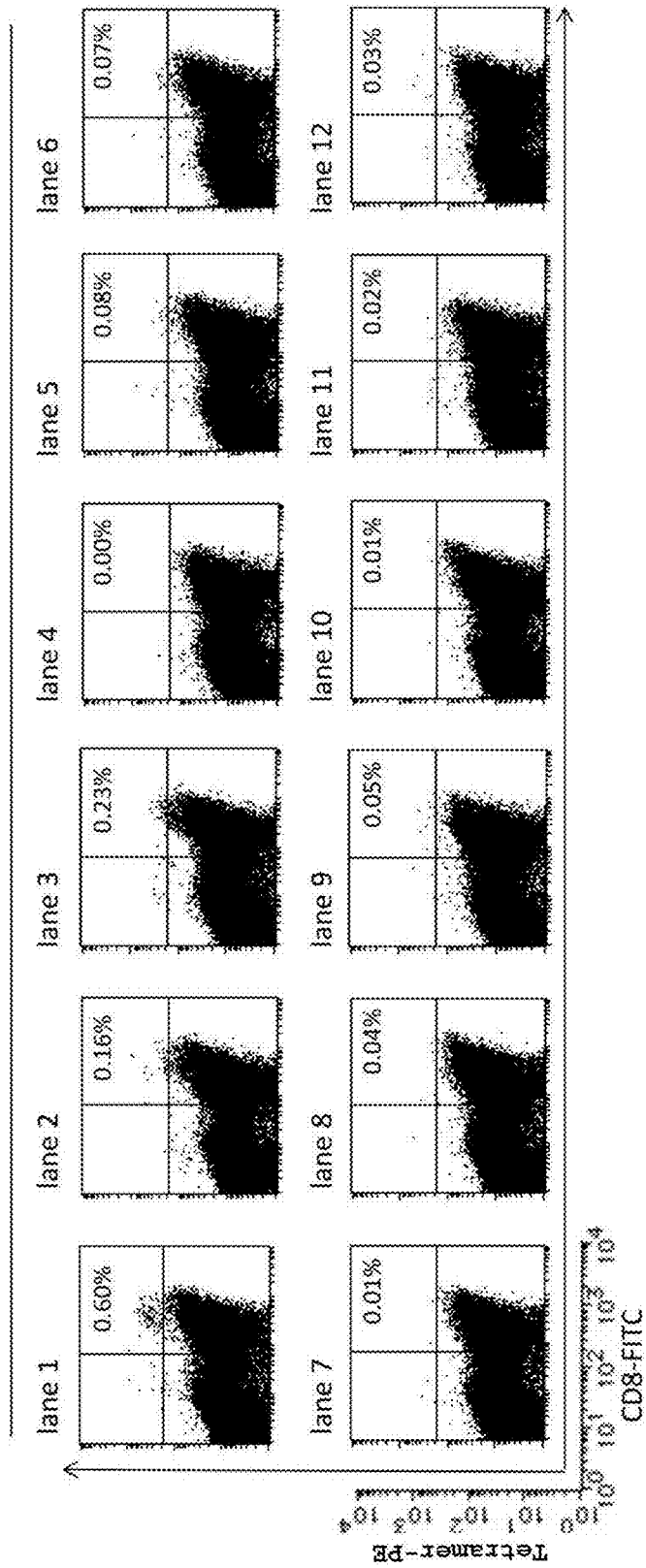

[Fig. 48]
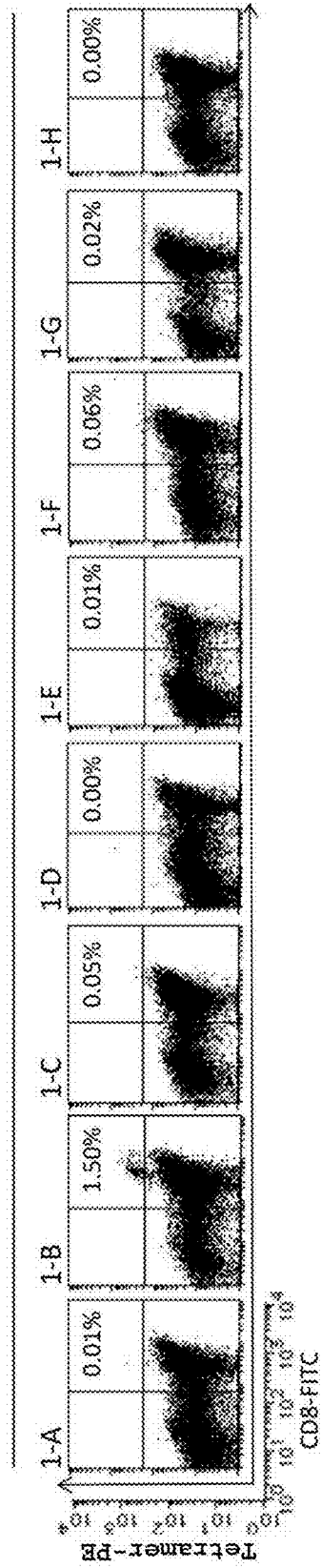

[Fig. 49]
Result of induction of BORIS-specific CTL
(sample: *11-13, third stage)
Sample: *11-13
SEQ ID No: 60 + SEQ ID No: 63 + SEQ ID No: 66 + SEQ ID No: 70
epitope candidate peptide
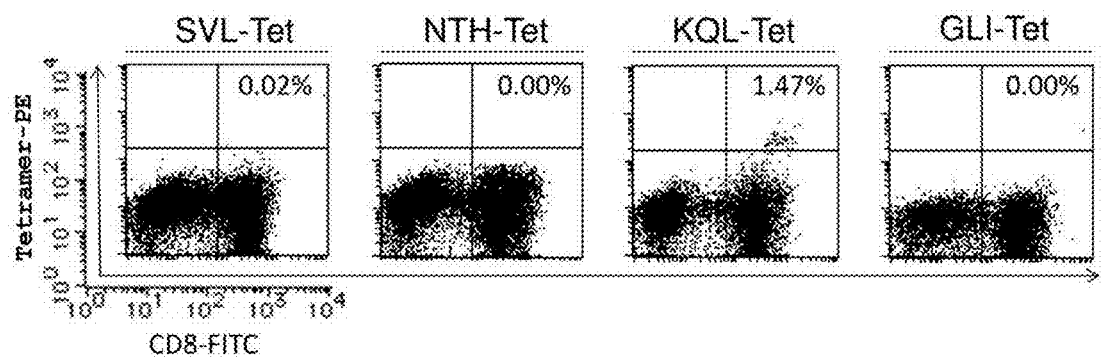

[Fig. 50]
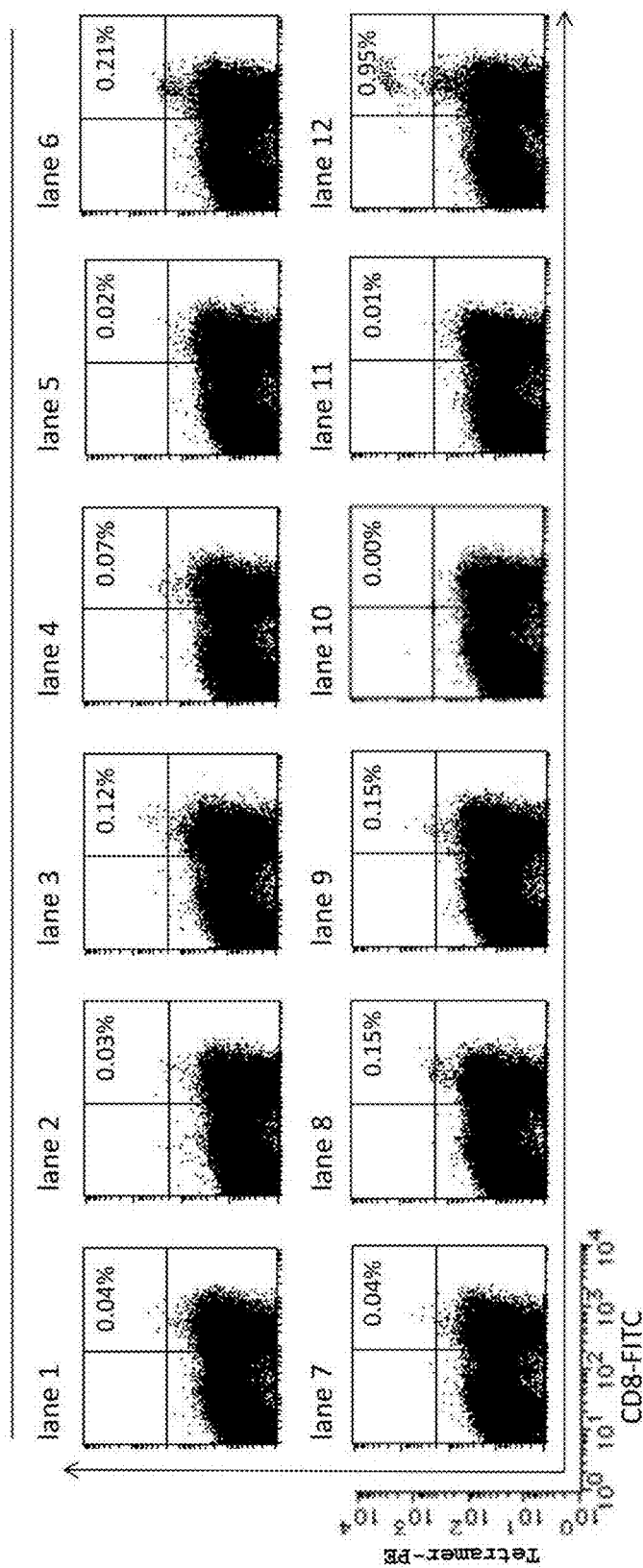

[Fig. 51]
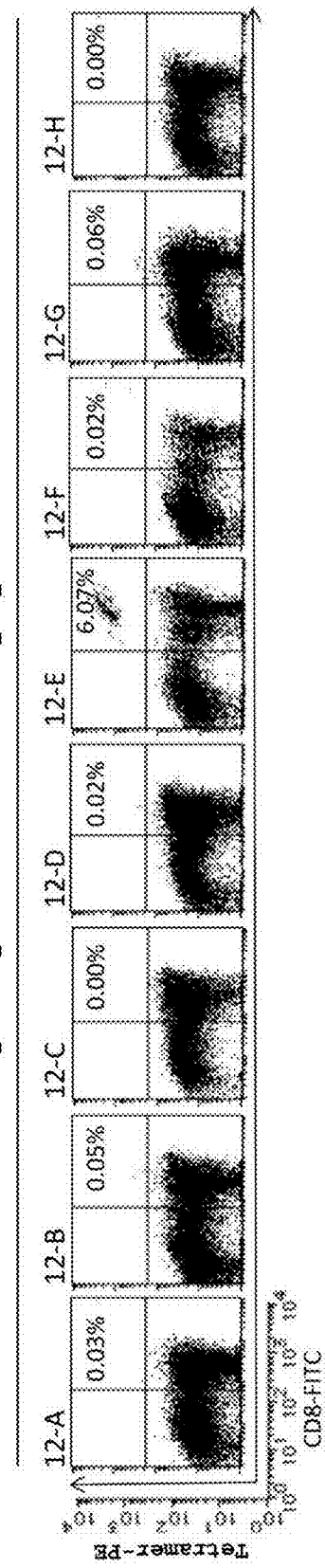

[Fig. 52]
Result of induction of BORIS-specific CTL
(sample: *11-13, third stage)
Sample: *11-13
SEQ ID No: 61 + SEQ ID No: 64 + SEQ ID No: 67 + SEQ ID No: 71
epitope candidate peptide
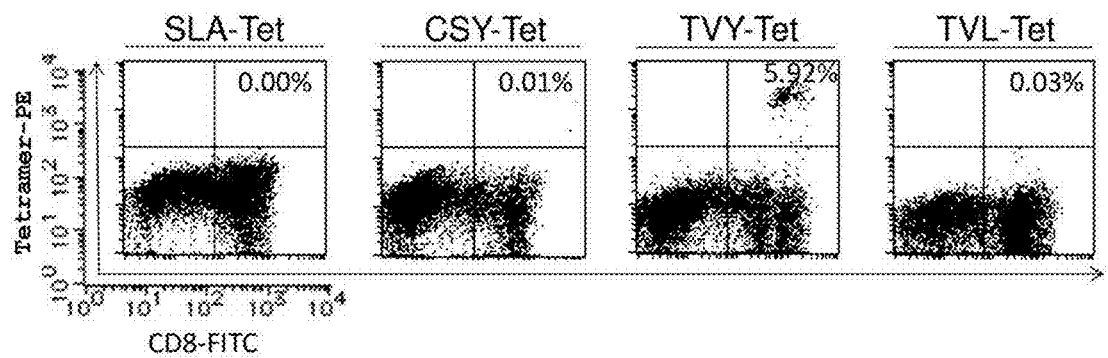

[Fig. 53]
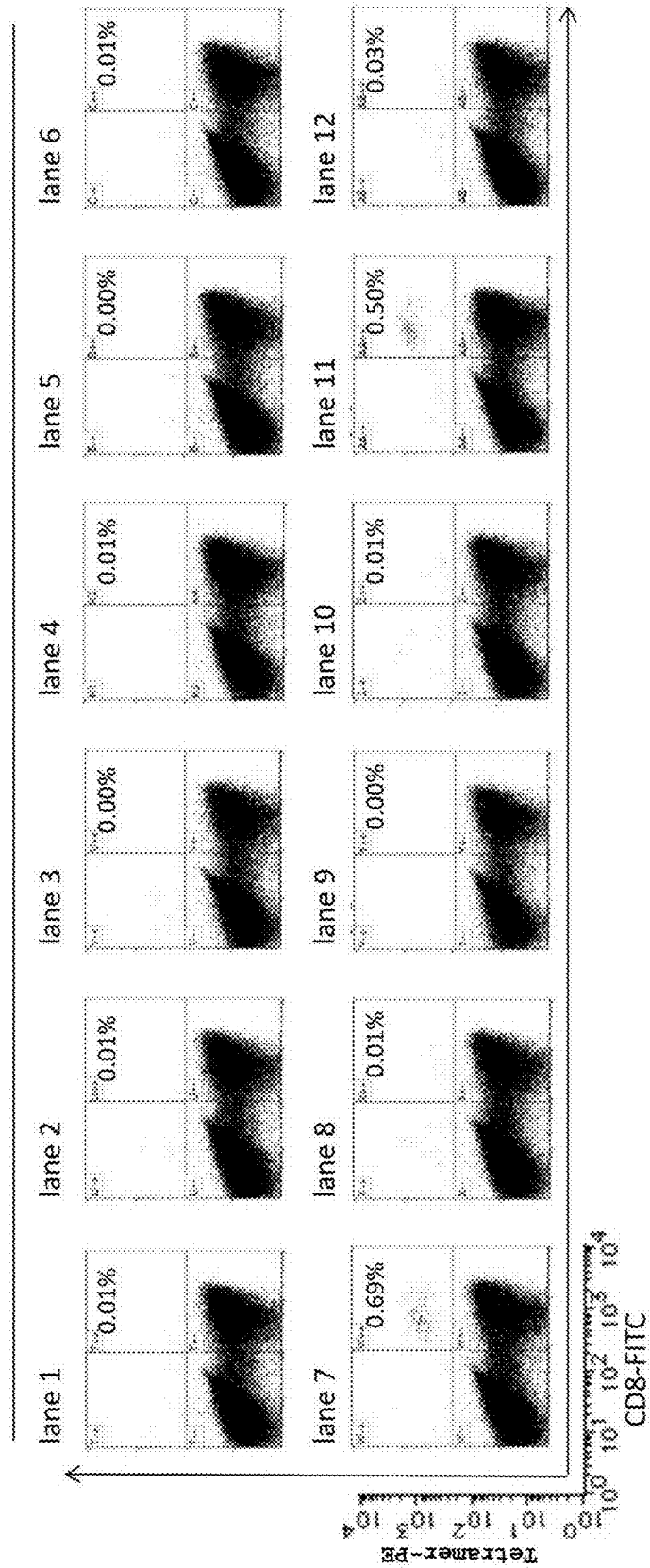

[Fig. 54]
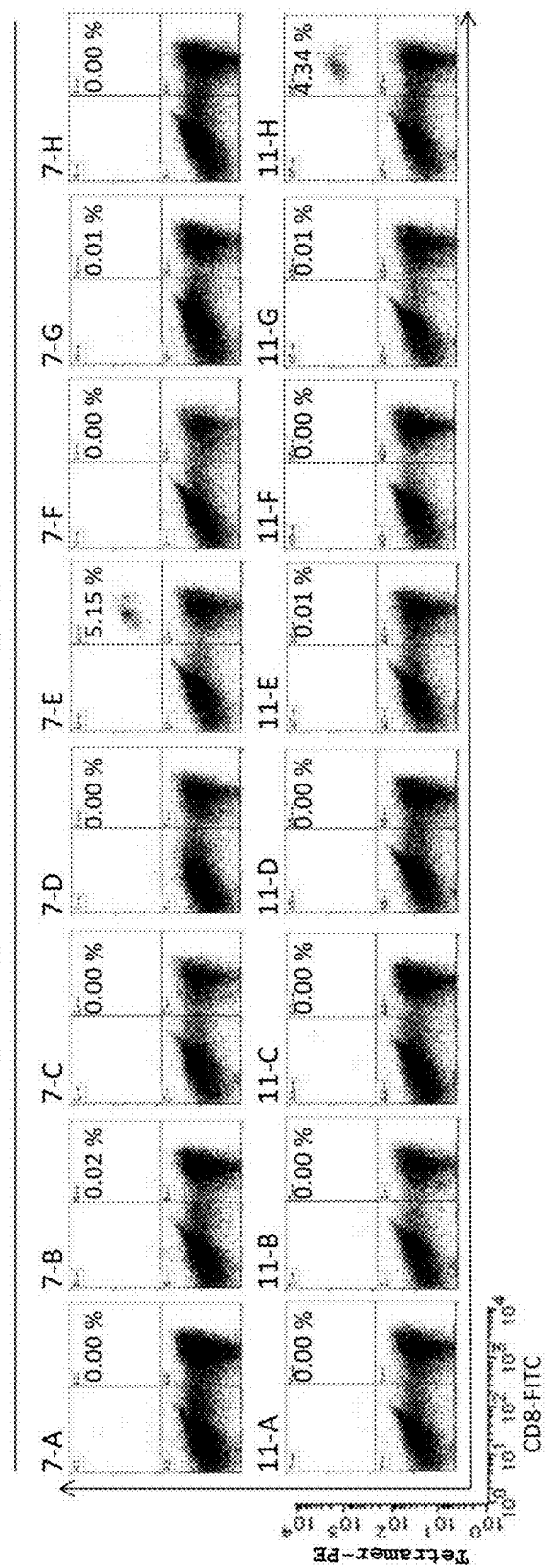

[Fig. 55]
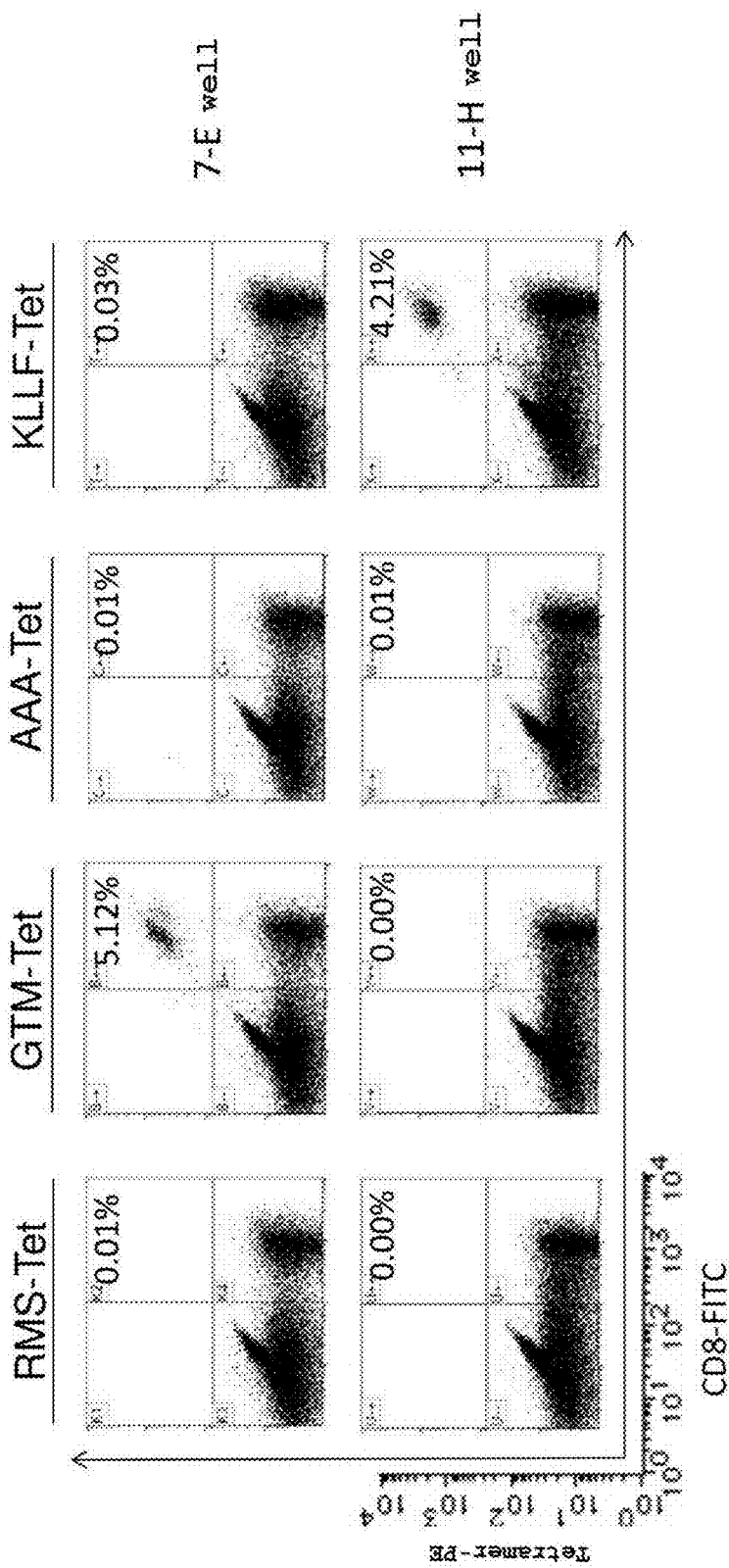

[Fig. 56]

Specificity of BORIS sf5-specific antibody and BORIS sf6-specific antibody

Primary antibody
Lane 1, 2, 5, 6: Myc Tag antibody
Lane 3, 4: BORIS sf5 -specific antibody
Lane 7, 8: BORIS sf6 -specific antibody Secondary antibody
Lane 1, 2, 5, 6: HRP-labeled anti-mouse IgG
Lane 3, 4: HRP-labeled anti-mouse IgG
Lane 7, 8: HRP-labeled anti-mouse IgG Sample: cell extract
Lane 1, 3, 5, 7: 293T
Lane 2, 4: BORIS sf5/293T
Lane 6, 8: BORIS sf6/293T

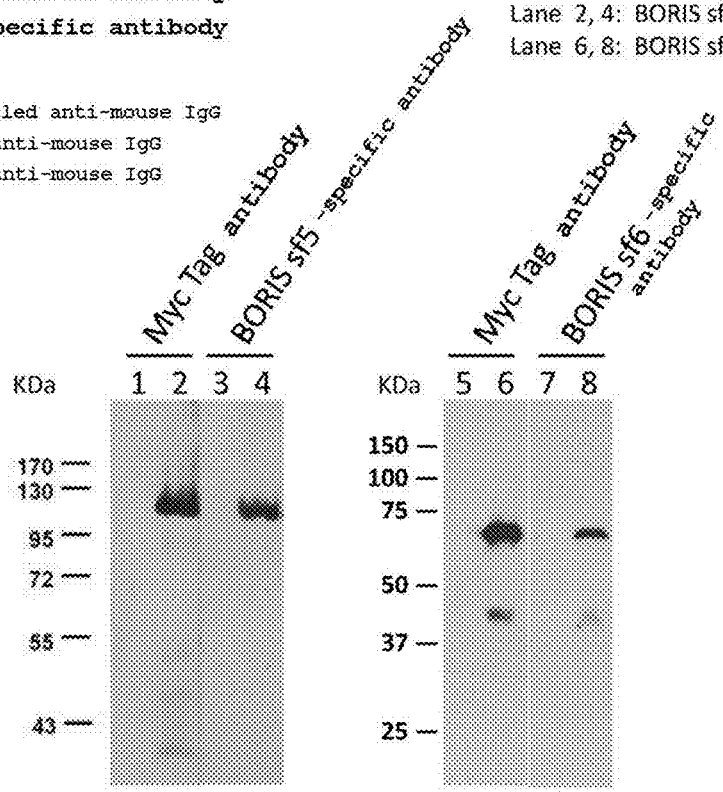

[Fig. 57]

Example of staining of lung cancer tissue section using BORIS sf5-specific antibody (a)

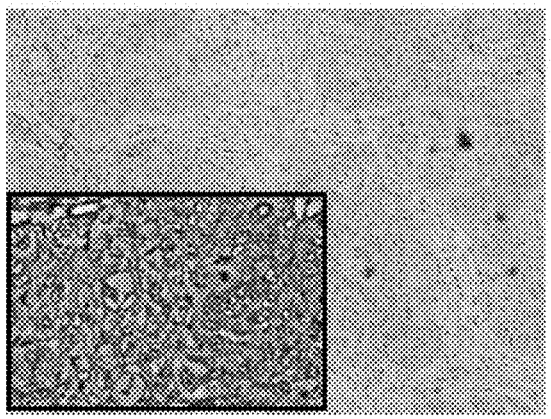

(b)

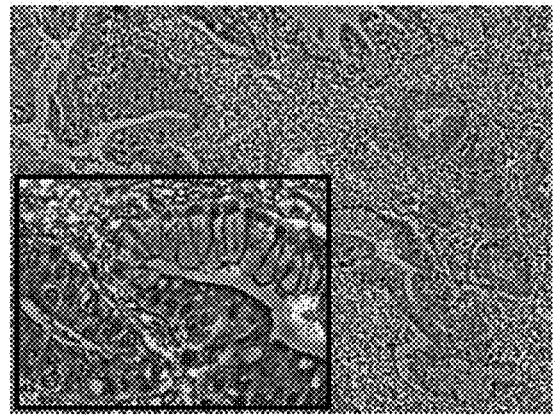

TUMOR ANTIGEN PEPTIDE

RELATED APPLICATION

This application is a national stage filing under 35 U.S.C. § 371 of International Application No. PCT/JP2015/076994, filed Sep. 24, 2015, the entire contents of which is incorporated by reference herein in its entirety.

TECHNICAL FIELD

The present invention relates to a BORIS-derived tumor antigen peptide which is useful as an agent for the prevention and/or treatment of a cancer, and the like.

BACKGROUND ART

The therapeutic effect of anti-cancer agents that have been developed to date is not sufficient and the probability of curing a cancer by treatment with an anti-cancer agent alone is very low. The inability of conventional treatment agents to selectively target cells that form the basis of cancer tissue can be cited as a cause of this. In recent years, as such 'cells that form the basis of cancer tissue' the presence of cancer stem cells has been reported. Cancer stem cells are cells that are present in small proportions among cancer cells; they have high tumorigenicity, replication competence, and differentiation potency, and are thought to be causal cells involved in the occurrence, recurrence, and metastasis of a cancer. Therefore, if cancer stem cells can be targeted, it can be expected that the possibility of suppressing effectively the proliferation, recurrence, and metastasis of a cancer will be high. That is, the development of a technique for detecting cancer stem cells and a novel treatment agent that targets cancer stem cells are important issues in cancer medicine.

On the other hand, in the elimination of tumor cells, virus-infected cells, etc. in a living body, cell-mediated immunity, in particular that involving cytotoxic T cells (called CTLs), has an important function. In the case of the elimination of tumor cells, a CTL recognizes a complex between an antigen peptide (tumor antigen peptide) and an MHC (Major Histocompatibility Complex) class I antigen (called an HLA class I antigen in the case of humans) on a tumor cell and attacks and destroys the tumor cell. A tumor antigen peptide is produced by in-cell degradation, by a protease, of a protein (a tumor antigen protein) that is expressed specifically in a tumor cell, after it has been synthesized in the cell. The tumor antigen peptide thus produced binds to an MHC class I antigen (HLA class I antigen) in the endoplasmic reticulum to form a complex, which is transported to the cell surface, and the antigen is presented. A tumor-specific CTL recognizes the complex that contains the antigen peptide that has been thus subjected to antigen presentation, and an anti-tumor effect is exhibited by the tumor cell being attacked via cytotoxic action or lymphokine production. Accompanying the elucidation of such a series of actions, a therapy in which a tumor antigen protein or a tumor antigen peptide is utilized as a so-called cancer immunotherapy agent (cancer vaccine) to thus enhance cancer-specific CTLs in the body of a cancer patient is in the process of being developed.

The BORIS (Brother of the Regulator of Imprinted Sites) gene is a paralog of the CTCF gene, and has 11 zinc finger regions between two peptide-encoding regions, that is, a region encoding an N terminal peptide region and a region encoding a C terminal peptide region. BORIS is known to function as a usual transcription factor such as a repressor and an activator for various types of gene expression and, in addition, is known to be expressed in various tumor cells, in particular cancer stem cells. Furthermore, it has been reported that the zinc finger region of BORIS has high homology with the CTCF gene; BORIS has 23 isoforms classified into six subfamily groups, and all thereof are splicing variants formed after transcription (Non-Patent Document 1). Furthermore, since BORIS is not expressed in normal tissue other than the testis, it is attracting attention as a target candidate in cancer diagnosis and treatment, and antibodies specific to BORIS subfamilies, siRNA for inhibiting the expression of the BORIS gene, etc. have been reported (Patent Documents 1 and 2). Moreover, it has also been reported that a BORIS protein sequence has been analyzed, sequences restricted to HLA-A0201 have been predicted therefrom, and a CTL that specifically recognizes a cell actually presenting one among these sequences as an antigen could be induced (Non-Patent Document 2).

PRIOR ART DOCUMENTS

Patent Documents

[Patent Document 1] International Patent Application WO2008/028066
[Patent Document 2] US Patent Application Laid-open No. 2009/0169613

Non-Patent Documents

[Non-Patent Document 1] Pugacheva et al., PLoS ONE 5 (11): e13872
[Non-Patent Document 2] Romagnoli et al., Rapporti ISTISAN. 2006; 06 (50), 36-40

DISCLOSURE OF INVENTION

Problems to be Solved by the Invention

It is an object of the present invention to provide a BORIS-derived tumor antigen peptide, in particular a BORIS isoform- or subfamily-specific tumor antigen peptide, and a pharmaceutical composition, etc. containing the above peptide as an active ingredient that is useful for the prevention and/or treatment of a cancer, in particular a pharmaceutical composition, etc. for specifically treating cancer stem cells.

Means for Solving the Problems

While investigating BORIS as a tumor antigen used in a cancer vaccine treatment, the present inventors have found that BORIS of a specific subfamily is specifically expressed in a cell that shows stem cell-like properties in cervical cancer or ovarian cancer. Upon further investigation based on such a finding, it has been found that it is possible, by inducing a cytotoxic T cell (CTL) that recognizes a cell expressing BORIS of a specific isoform or subfamily, to treat many cancer cells and/or cancer stem cells, and as a result of yet further investigation the present invention has been accomplished.

That is, the present invention relates to the following:
[1] A method for inducing a CTL that specifically recognizes a cell expressing a BORIS gene belonging to isoform A or C or subfamily 5 or 6, the method comprising bringing into contact with a peripheral blood lymphocyte either (a) or (b) below:
(a) a polypeptide that is a partial peptide of the BORIS protein, has a length of 8 to 20 amino acids, and has HLA-binding capacity,
(b) a polynucleotide encoding at least one polypeptide described in (a) above.
[2] The method according to [1], the method being carried out in vitro.
[3] A polypeptide used in the method according to [1] or [2], the polypeptide being a partial peptide of a polypeptide represented by SEQ ID No: 1 or SEQ ID No: 2, having a length of 8 to 20 amino acids, and having HLA-binding capacity.
[4] The polypeptide according to [3], the polypeptide having a length of 8 to 11 amino acids.
[5] The polypeptide according to [3] or [4], the polypeptide being a partial peptide of a polypeptide represented by SEQ ID No: 1.
[6] The polypeptide according to [5], the polypeptide being represented by SEQ ID No: 3, SEQ ID No: 4, SEQ ID No: 5, or SEQ ID No: 72.
[7] The polypeptide according to [3] or [4], the polypeptide being a partial peptide of a polypeptide represented by SEQ ID No: 2.
[8] The polypeptide according to [7], the polypeptide being represented by SEQ ID No: 10.
[9] A polypeptide used in the method according to [1] or [2], the polypeptide having HLA-A11 antigen-binding capacity.
[10] The polypeptide according to [9], wherein it is represented by SEQ ID No: 65, SEQ ID No: 66, SEQ ID No: 67, or SEQ ID No: 72.
[11] A polypeptide used in the method according to [1] or [2], the polypeptide having HLA-A2 antigen-binding capacity and being represented by SEQ ID No: 4, SEQ ID No: 5, SEQ ID No: 10, SEQ ID No: 47, or SEQ ID No: 57.
[12] A polypeptide used in the method according to [1] or [2], the polypeptide having HLA-A24 antigen-binding capacity.
[13] The polypeptide according to [12], wherein it is represented by SEQ ID No: 3 or 10.
[14] The polypeptide according to any one of [3] to [13], the polypeptide having one or a plurality of amino acids added, deleted, or substituted.
[15] A polynucleotide used in the method according to [1] or [2], the polynucleotide encoding the polypeptide according to any one of [3] to [14].
[16] A cytotoxic T cell (CTL) inducer comprising at least one of the polypeptides according to any one of [3] to [14] as an active ingredient.
[17] A pharmaceutical composition comprising the CTL inducer according to [16] as an active ingredient.
[18] A composition for the treatment of cancer stem cells, comprising the CTL inducer according to [16] as an active ingredient.
[19] A composition for the prevention and/or treatment of a cancer, comprising the CTL inducer according to [16] as an active ingredient.
[20] A composition for the prevention and/or treatment of a cancer, comprising as an active ingredient a cytotoxic T cell (CTL) induced by the method according to [1] or [2].
[21] The composition for the prevention and/or treatment of a cancer according to [19] or [20], wherein the cancer is lung cancer or a cancer in a female-specific organ.
[22] An expression vector comprising the polynucleotide according to [15].
[23] A pharmaceutical composition for the treatment or prevention of a cancer, comprising as an active ingredient the polynucleotide according to [15] or the expression vector according to [22].
[24] An HLA-tetramer comprising an HLA and the polypeptide according to any one of [3] to [14].
[25] A method for producing an antigen-presenting cell, comprising bringing into contact in vitro a cell having antigen-presenting ability and (a) or (b) below:
(a) the polypeptide according to any one of [3] to [14],
(b) a polynucleotide encoding at least one polypeptide described in (a) above.
[26] An antibody that specifically binds to at least part of a polypeptide represented by SEQ ID No: 1 or SEQ ID No: 2.
[27] A kit for detecting a BORIS protein, the kit comprising the antibody according to [26].

Effects of the Invention

In accordance with the present invention, there can be provided a method for inducing a CTL that recognizes BORIS of a specific isoform or subfamily, a tumor antigen peptide that is useful as a CTL inducer used in the method, and a pharmaceutical composition, etc. that is useful for the prevention and/or treatment of a cancer containing the above as an active ingredient. In particular, since a cell having stem cell-like properties (that is, a cancer stem cell) expresses BORIS of a specific subfamily in some cancers, it becomes possible to selectively treat a cancer stem cell with the treatment agent of the present invention.

BRIEF DESCRIPTION OF DRAWINGS

FIG. 1 is a photograph of a spheroid formed by a spheroid formation assay.
FIG. 2 is a graph showing relative expression levels of stemness genes SOX2, NANOG, and Oct3/4 in cervical cancer cell lines CaSki and TCS.
FIG. 3 is a diagram showing expression of BORIS in normal tissue. (a) shows the result of RT-PCR, and (b) shows relative expression levels.
FIG. 4 is a graph showing relative expression levels of BORIS in bulk group cells and sphere group cells of various cervical cancer cell lines.
FIG. 5 is a graph showing relative expression levels of BORIS in various cancer cells.
FIG. 6 is a diagram showing a comparison of the amount of expression of BORIS subfamilies between bulk group cells and sphere group cells in cervical cancer cell lines CaSki and MS751.
FIG. 7 is a diagram showing a comparison of the amount of expression of BORIS subfamilies between bulk group cells and sphere group cells in ovarian cancer cell lines TOV21G and smov2.
FIG. 8-1 is a photograph showing the result of a sphere formation assay when there was overexpression of BORIS subfamilies in the TCS cell line, which is a cervical cancer cell line.
FIG. 8-2 is a graph showing the result of a sphere formation assay when there was overexpression of BORIS subfamilies in the TCS cell line, which is a cervical cancer cell line.

FIG. 9-1 is a photograph showing the result of a sphere formation assay when there was overexpression of BORIS subfamilies in the SKG-IIIb cell line, which is a cervical cancer cell line.

FIG. 9-2 is a graph showing the result of a sphere formation assay when there was overexpression of BORIS subfamilies in the SKG-IIIb cell line, which is a cervical cancer cell line.

FIG. 10 is a graph showing the result of an HLA-A02-binding assay of HLA-binding peptide candidates abstracted from a BORIS sf6-specific sequence.

FIG. 11 is a graph showing the result of a folding test of HLA-A*24:02-binding BORIS-specific CTL epitope candidate peptides. The graph shows the amount of HLA-monomer formed estimated from the peak area representing the HLA-monomer.

FIG. 12-1 is a diagram showing the result of a first stage analysis in which a reaction with an HLA-tetramer reagent was analyzed using a flow cytometer when a sample harvested from sample number A24-38 was cocultured with RMM peptide.

FIG. 12-2 is a diagram showing the result of a second stage analysis in which a reaction with an HLA-tetramer reagent was analyzed using a flow cytometer when a sample harvested from sample number A24-38 was cocultured with RMM peptide. Since CTLs were detected in lanes 2, 4, 8, and 9 in the first stage analysis, these lanes were analyzed in the second stage analysis.

FIG. 13 is a diagram showing the result of a functional analysis of the function of RMM peptide-specific CTLs using RMM-Tet. It can be seen that IFNγ was produced specifically to RMM peptide when stimulation was carried out with RMM peptide.

FIG. 14-1 shows a graph in which mRNA expression (a) and cell proliferation (b) were compared in CaSki cell line transfected with siRNA.

FIG. 14-2 is a microscopy image of CaSki cells transfected with siRNA.

FIG. 15 is a graph comparing stemness gene expression in CaSki cell line transfected with siRNA.

FIG. 16-1 is a graph comparing sphere formation capability of CaSki cell line (a) and MS751 cell line (b) transfected with siRNA.

FIG. 16-2 is a microscopy image of cell lines transfected with siRNA.

FIG. 17 shows a graph comparing radiation tolerance of cell lines transfected with siRNA.

FIG. 18 is a Kaplan-Meier survival curve showing that when BORIS expression is high the survival rate is extremely low.

FIG. 19-1 is a diagram showing a comparison of the amount of expression of BORIS subfamilies between bulk group cells and sphere group cells in small cell lung cancer cell lines SBC1, SBC3, SBC5, and Lc817.

FIG. 19-2 is a diagram showing a comparison of the amount of expression of BORIS subfamilies between bulk group cells and sphere group cells in non-small cell lung cancer cell lines Lu99A and 86-2.

FIG. 19-3 is a diagram showing a comparison of the amount of expression of BORIS subfamilies between bulk group cells and sphere group cells in lung squamous cancer cell lines LK2, EBC1, and Sq1.

FIG. 19-4 is a diagram showing a comparison of the amount of expression of BORIS subfamilies between bulk group cells and sphere group cells in lung adenocarcinoma cell lines A549, LHK2, LHK2-SOX2, and PC3.

FIG. 19-5 is a diagram showing a comparison of the amount of expression of BORIS subfamilies between bulk group cells and sphere group cells in lung adenocarcinoma primary cultured cells Primary3, Primary4, Primary5, and Primary7.

FIG. 20 is a diagram showing the result of a first stage analysis in which a sample harvested from sample number A2-34 was cocultured with KLL peptide, and a reaction with an HLA-tetramer reagent was then analyzed using a flow cytometer.

FIG. 21 is a diagram showing the result of a second stage analysis in which a sample harvested from sample number A2-34 was cocultured with KLL peptide, and a reaction with an HLA-tetramer reagent was then analyzed using a flow cytometer. Since in the first stage analysis CTLs were detected in lanes 5 and 11, in the second stage analysis these lanes were analyzed.

FIG. 22 is a diagram showing the result of a first stage analysis in which a sample harvested from sample number A2-29 was cocultured with LLF peptide, and a reaction with an HLA-tetramer reagent was then analyzed using a flow cytometer.

FIGS. 23-1 and 23-2 are diagrams showing the result of a second stage analysis in which a sample harvested from sample number A2-29 was cocultured with LLF peptide, and a reaction with an HLA-tetramer reagent was then analyzed using a flow cytometer. Since in the first stage analysis CTLs were detected in lanes 1, 2, 4, 5, 6, 7, 8, 9, 10, and 11, in the second stage analysis these lanes were analyzed.

FIG. 24 is a diagram showing the result when a sample harvested from sample number A2-S1 was cocultured with LLF peptide-presenting cells, and a reaction with an HLA-tetramer reagent was then analyzed using a flow cytometer.

FIG. 25 is a diagram showing the result when the IFNγ production capability of CTLs induced by coculturing samples harvested from sample numbers A2-S1, A2-S2, and A2-S3 with LLF peptide-presenting cells was analyzed using ELISPOT.

FIG. 26 is a diagram showing the result when CTLs induced when a sample harvested from sample number A2-S1 was cocultured with LLF peptide-presenting cells were monocloned and amplified, and a reaction with an HLA-tetramer reagent was then analyzed using a flow cytometer.

FIG. 27 is a diagram showing the result when CTLs induced when a sample harvested from sample number A2-S1 was cocultured with LLF peptide-presenting cells were monocloned and amplified, and the IFNγ production capability was then analyzed using ELISPOT.

FIG. 28 is a diagram showing the result when CTLs induced when a sample harvested from sample number A2-S1 was cocultured with LLF peptide-presenting cells were monocloned and amplified, and the cytotoxicity was then analyzed using an LDH killing assay.

FIG. 29 is a diagram showing the result when a sample harvested from sample number A24-S4 or sample number A2-S5 was cocultured with RMM peptide-presenting cells, and a reaction with an HLA-tetramer reagent was then analyzed using a flow cytometer.

FIG. 30 is a diagram showing the result of analyzing, using ELISPOT, the IFNγ production capability of CTLs induced when a sample harvested from sample number A24-S4 or sample number A2-S5 was cocultured with RMM peptide-presenting cells.

FIG. 31 is a diagram showing the result of analyzing, using a flow cytometer, a reaction with an HLA-tetramer reagent after CTLs induced when a sample harvested from sample number A24-S4 was cocultured with RMM peptide-presenting cells were monocloned and amplified.

FIG. 32 is a diagram showing the result of analyzing, using a flow cytometer, a reaction with an HLA-tetramer reagent after CTLs induced when a sample harvested from sample number A2-S5 was cocultured with RMM peptide-presenting cells were monocloned and amplified.

FIG. 33 is a graph showing the result of a folding test of HLA-A*02:01-restricted BORIS-specific CTL epitope candidate peptides. The graph shows the amount of HLA-monomer formed estimated from the peak area representing the HLA-monomer.

FIG. 34 is a diagram showing the result of a first stage analysis in which a reaction with an HLA-tetramer reagent was analyzed using a flow cytometer when a sample harvested from sample number A2-29 was cocultured with VLE peptide.

FIG. 35 is a diagram showing the result of a second stage analysis in which a reaction with an HLA-tetramer reagent was analyzed using a flow cytometer when a sample harvested from sample number A2-29 was cocultured with VLE peptide. Since in the first stage analysis CTLs were detected in lane 10, in the second stage analysis lane 10 was analyzed.

FIG. 36 is a diagram showing the result of a first stage analysis in which a reaction with an HLA-tetramer reagent was analyzed using a flow cytometer when a sample harvested from sample number A2-27 was cocultured with VLE peptide.

FIG. 37 is a diagram showing the result of a second stage analysis in which a reaction with an HLA-tetramer reagent was analyzed using a flow cytometer when a sample harvested from sample number A2-27 was cocultured with VLE peptide. Since in the first stage analysis CTLs were detected in lane 3, in the second stage analysis lane 3 was analyzed.

FIG. 38 is a diagram showing the result of a first stage analysis in which a reaction with an HLA-tetramer reagent was analyzed using a flow cytometer when a sample harvested from sample number A2-34 was cocultured with VLE peptide.

FIG. 39 is a diagram showing the result of a second stage analysis in which a reaction with an HLA-tetramer reagent was analyzed using a flow cytometer when a sample harvested from sample number A2-34 was cocultured with VLE peptide. Since in the first stage analysis CTLs were detected in lane 4, in the second stage analysis lane 4 was analyzed.

FIG. 40 is a diagram showing the result of a first stage analysis in which a reaction with an HLA-tetramer reagent was analyzed using a flow cytometer when a sample harvested from sample number A2-29 was cocultured with KLA peptide.

FIG. 41 is a diagram showing the result of a second stage analysis in which a reaction with an HLA-tetramer reagent was analyzed using a flow cytometer when a sample harvested from sample number A2-29 was cocultured with KLA peptide. Since in the first stage analysis CTLs were detected in lanes 2, 5, and 11, in the second stage analysis lanes 2, 5, and 11 were analyzed.

FIG. 42 is a diagram showing the result of a first stage analysis in which a reaction with an HLA-tetramer reagent was analyzed using a flow cytometer when a sample harvested from sample number A2-29 was cocultured with VLT peptide.

FIG. 43 is a diagram showing the result of a second stage analysis in which a reaction with an HLA-tetramer reagent was analyzed using a flow cytometer when a sample harvested from sample number A2-29 was cocultured with VLT peptide. Since in the first stage analysis CTLs were detected in lanes 7 and 9, in the second stage analysis lanes 7 and 9 were analyzed.

FIG. 44 is a diagram showing the result of a functional analysis of the function of KLA peptide-specific CTLs using KLA-Tet. It can be seen that CD107a was detected specifically to KLA peptide when stimulation was carried out with KLA peptide.

FIG. 45 is a diagram showing the result of a functional analysis of the function of VLT peptide-specific CTLs using VLT-Tet. It can be seen that CD107a was induced specifically to VLT peptide when stimulation was carried out with VLT peptide.

FIG. 46 is a graph showing the result of a folding test of HLA-A*11:01-restricted BORIS-specific CTL epitope candidate peptides. The graph shows the peak area representing the HLA monomer.

FIG. 47 is a diagram showing the result of a first stage analysis in which a reaction with an HLA-tetramer reagent was analyzed using a flow cytometer when a sample harvested from sample number *11-13 was cocultured with SVL peptide, NTH peptide, KQL peptide, and GLI peptide.

FIG. 48 is a diagram showing the result of a second stage analysis in which a reaction with an HLA-tetramer reagent was analyzed using a flow cytometer when a sample harvested from sample number *11-13 was cocultured with SVL peptide, NTH peptide, KQL peptide, and GLI peptide. Since in the first stage analysis CTLs were detected in lane 1, in the second stage analysis lane 1 was analyzed.

FIG. 49 is a diagram showing the result of a third stage analysis in which a reaction with an HLA-tetramer reagent was analyzed using a flow cytometer when a sample harvested from sample number *11-13 was cocultured with SVL peptide, NTH peptide, KQL peptide, and GLI peptide. Since in the second stage analysis CTLs were detected in well B of lane 1, in the third stage analysis well B of lane 1 was analyzed.

FIG. 50 is a diagram showing the result of a first stage analysis in which a reaction with an HLA-tetramer reagent was analyzed using a flow cytometer when a sample harvested from sample number *11-13 was cocultured with SLA peptide, CSY peptide, TVY peptide, and TVL peptide.

FIG. 51 is a diagram showing the result of a second stage analysis in which a reaction with an HLA-tetramer reagent was analyzed using a flow cytometer when a sample harvested from sample number *11-13 was cocultured with SLA peptide, CSY peptide, TVY peptide, and TVL peptide. Since in the first stage analysis CTLs were detected in lane 12, in the second stage analysis lane 12 was analyzed.

FIG. 52 is a diagram showing the result of a third stage analysis in which a reaction with an HLA-tetramer reagent was analyzed using a flow cytometer when a sample harvested from sample number *11-13 was cocultured with SLA peptide, CSY peptide, TVY peptide, and TVL peptide. Since in the second stage analysis CTLs were detected in well E of lane 12, in the third stage analysis well E of lane 12 was analyzed.

FIG. 53 is a diagram showing the result of a first stage analysis in which a reaction with an HLA-tetramer reagent was analyzed using a flow cytometer when a sample harvested from sample number *11-16 was cocultured with RMS peptide, GTM peptide, AAA peptide, and KLLF peptide.

FIG. 54 is a diagram showing the result of a second stage analysis in which a reaction with an HLA-tetramer reagent was analyzed using a flow cytometer when a sample harvested from sample number *11-16 was cocultured with RMS peptide, GTM peptide, AAA peptide, and KLLF peptide. Since in the first stage analysis CTLs were detected in lane 7 and lane 11, in the second stage analysis, lanes 7 and 11 were analyzed.

FIG. 55 is a diagram showing the result of a third stage analysis in which a reaction with an HLA-tetramer reagent was analyzed using a flow cytometer when a sample harvested from sample number *11-16 was cocultured with RMS peptide, GTM peptide, AAA peptide, and KLLF peptide. Since in the second stage analysis CTLs were detected in well E of lane 7 and well H of lane 11, in the third stage analysis well E of lane 7 and well H of lane 11 were analyzed.

FIG. 56 shows the result of western blotting using a 293T cell extract in which Myc Tag BORIS sf5 and BORIS sf6 were transiently forcibly expressed. Since it was confirmed that for both specific antibodies bands were observed at the same positon as that when Myc Tag antibody was used, the specificity of these antibodies was shown.

FIG. 57 shows the result of immunostaining a lung cancer tissue section using a BORIS sf5-specific antibody. It was confirmed that even for the same lung cancer tissue, there were those that were positive for expression of BORIS sf5 and those that were negative therefor. (a) shows a negative stained image and (b) shows a positive stained image. In (b) cells stained with a brown color were scatteringly observed, whereas almost no staining was observed in (a).

MODES FOR CARRYING OUT THE INVENTION

The present invention is explained in detail below.
(1) Polypeptide of the Present Invention The 'epitope peptide' referred to in the present invention means a polypeptide that binds to an MHC (an HLA for humans) and is subjected to antigen presentation on the cell surface. The epitope peptide includes a CTL epitope peptide that binds to an MHC class I, is subjected to antigen presentation, and is recognized by a CD8-positive T cell, and a helper epitope peptide that binds to an MHC class II, is subjected to antigen presentation, and is recognized by a CD4-positive T cell.

Among epitope peptides, a protein-derived polypeptide that is specifically or over expressed in a tumor cell is in particular called a tumor antigen peptide. The antigen presentation referred to here means a phenomenon in which a polypeptide present within a cell binds to an MHC and this MHC/antigen peptide complex is localized on the cell surface. As described above, it is known that an antigen presented on a cell surface is recognized by a T cell, etc. and then activates cell-mediated immunity or humoral immunity; since an antigen presented by an MHC class I activates cell-mediated immunity and is also recognized by a T cell receptor of a naive T cell to thus induce the naive T cell to become a CTL having cytotoxicity, a tumor antigen peptide used in immunotherapy is preferably a polypeptide that binds to an MHC class I and is presented as an antigen.

On the other hand, an antigen protein that is taken in by an antigen-presenting cell such as a dendritic cell binds to an MHC class II, is subjected to antigen presentation on the surface of the antigen-presenting cell, is recognized by a CD4 positive T cell, and finally can induce a helper T cell, which activates cellular immunity or humoral immunity. Since a helper T cell not only has similar cytotoxicity to a CTL, but also plays an important part in the maintenance of activity and survival of a CTL, a polypeptide that binds to an MHC class II and is subjected to antigen presentation is also preferable as a tumor antigen peptide used in immunotherapy. It is known that a polypeptide that binds to an MHC class I has a length of about 8 to 11 amino acids and a polypeptide that binds to MHC class II has a length of about 12 to 20 amino acids.

In the present invention, a 'tumor' includes a benign tumor and a malignant tumor (cancer, malignant neoplasm). Cancer includes a hematopoietic tumor, an epithelial malignant tumor (carcinoma), and a nonepithelial malignant tumor (sarcoma).

In the present invention, when referring simply to 'BORIS', it means the Brother of the Regulator of Imprinted Sites gene, or an mRNA or protein, which is an expression product of the gene. It is known that expression control of the BORIS gene involves three types of promoters (called promoter A, promoter B, and promoter C in sequence from upstream), and there are broadly speaking three isoforms (called isoform A, isoform B, and isoform C corresponding to the respective promoter) depending on the promoter that controls the transcription. Each isoform is further classified into a plurality of splicing variants according to the manner in which splicing is received at the time of transcription. From this, it is known that BORIS has a total of 23 isoforms, that is, six isoforms A (A1 to A6), eight isoforms B (B0 to B7), and nine isoforms C (C1 to C9). For example, BORIS C1 isoform has a sequence represented by SEQ ID No: 76.

As described above, BORIS is a paralog of CTCF, which is also called an 11-zinc finger protein, and the BORIS protein has a structure having an N terminal peptide region and a C terminal peptide region at the N terminal and the C terminal of the 11 zinc finger regions respectively. The N terminal peptide region has a length of 24 amino acids, 53 amino acids, or 258 amino acids according to the isoform, and the sequences of those having the same length are highly conserved. The C terminal peptide region has various lengths, and the sequences thereof are also different from each other. BORIS is classified into six subfamilies (subfamily 1 to 6, in the present specification also simply abbreviated to sf1 to sf6) according to the sequence of the C terminal peptide region. Therefore, the C terminal sequence of each subfamily is a sequence characteristic of the respective subfamily, and it is highly conserved among isoforms belonging to the same subfamily.

The polypeptide of the present invention is subjected to antigen presentation on the cell surface of a cell expressing BORIS of a specific isoform or subfamily, and specifically BORIS belonging to isoform A or C or subfamily 5 or 6. Therefore, the polypeptide of the present invention is a partial peptide of BORIS belonging to isoform A or C or subfamily 5 or 6, has a length of 8 to 20 amino acids, and has HLA-binding capacity. Many cancer cells, including cancer stem cells, express such BORIS, and because of this the polypeptide of the present invention is useful in cancer immunotherapy.

In one embodiment, the polypeptide of the present invention is a partial peptide of a polypeptide represented by SEQ ID No: 1, which is a sequence characteristic of BORIS sf6, or SEQ ID No: 2, which is a sequence characteristic of BORIS sf5, the polypeptide including a peptide binding to an MHC, and in particular to an HLA; it is preferably a peptide that is subjected to antigen presentation by means of an MHC, in particular an HLA, and more preferably a peptide that is subjected to antigen presentation by means of an MHC, in particular an HLA, and can induce a CTL. There are several types of HLA; the polypeptide of the present invention preferably can bind to an HLA class I, more preferably can bind to HLA-A24, HLA-A11, or HLA-A02, and yet more preferably can bind to two or more HLAs among HLA-A24, HLA-A11, and HLA-A02. In another embodiment, a polypeptide that can bind to an HLA class II is also preferable.

For example, in the case in which the MHC is an HLA class I, it is known that most antigens presented via an HLA class I molecule are degraded by means of a cytoplasmic proteasome, are then transported to a TAP (transporter in antigen processing), bind to a complex between an HLA class I molecule and β2-microglobulin that is associated with the TAP within the rough endoplasmic reticulum, and are transported to the cell surface by exocytosis via a Golgi apparatus. Therefore, the polypeptide of the present invention may be subjected to a treatment such as processing prior to binding to an MHC, and a peptide that forms an epitope peptide as a result of such a treatment is also included in the polypeptide of the present invention. For example, since fusing a target peptide or protein with HSP70, HSP90, or gp96, which are chaperones acting in the series of antigen presentation pathways, enables antigen presentation to be carried out efficiently, in one embodiment the polypeptide of the present invention is fused with a chaperone that functions in an antigen presentation pathway.

Furthermore, the epitope peptide of the present invention may be one that has been modified in various ways so that it can be introduced easily into a living body. Examples of various types of modification that make introduction into a living body easy include a PT (Protein Transduction) domain of HIV. The PT domain of HIV is a peptide formed from the 49$^{th}$ to 57$^{th}$ amino acids of the Tat protein. Adding it to the N terminal and/or C terminal of a protein or peptide that is to be modified enables a target protein or peptide to be easily introduced into a cell.

As described above, since the polypeptide of the present invention may be subjected to a treatment such as processing prior to binding to an MHC, the amino acid length is not particularly limited as long as it is a sequence containing an amino acid sequence of an epitope peptide. However, it is preferable that the polypeptide of the present invention itself is an epitope peptide, and therefore the amino acid length is preferably on the order of about 8 to about 20 amino acids, more preferably about 8 to about 11 amino acids, and yet more preferably about 8 to about 10 amino acids.

In a preferred embodiment, the polypeptide of the present invention is a polypeptide that is a partial peptide of a polypeptide represented by SEQ ID No: 1, has a length of 8 to 11 amino acids, and has HLA-binding capacity.

In another preferred embodiment, the polypeptide of the present invention is a polypeptide that is a partial peptide of a polypeptide represented by SEQ ID No: 2, has a length of 8 to 11 amino acids, and has HLA-binding capacity.

Whether or not the polypeptide has 'HLA-binding capacity' can be discovered simply by using a method known in the art. Examples of such a method include, but are not limited to, an HLA-binding assay in which the amount of HLA expressed on the cell surface (that is, the amount of HLA binding to a polypeptide) is observed as the intensity of fluorescence using a monoclonal antibody to HLA as described in WO2010/50190, a binding assay using BIAcore surface plasmon resonance (SPR) described in Kim et al., Methods Mol Biol. 2013; 960: 447-59, etc., and a method using iTopia (iTopia Epitope Discovery System Assay, Beckman Coulter) in which observation is carried out using an HLA antibody that specifically binds only when a polypeptide and an HLA fixed to a solid phase are bound, described in Shin et al., PNAS, November 2007; 104: 19073-19078, etc.

As a result of examining partial peptides of the polypeptides represented by SEQ ID No: 1 and SEQ ID No: 2, polypeptides represented by SEQ ID No: 3, SEQ ID No: 4, SEQ ID No: 5 and SEQ ID No: 72 together with a polypeptide represented by SEQ ID No: 10 have been identified as epitope peptide candidates. Therefore, in a more preferred embodiment, the polypeptide of the present invention is a polypeptide represented by SEQ ID No: 3, SEQ ID No: 4, SEQ ID No: 5 or SEQ ID No: 72. In another more preferred embodiment, the polypeptide of the present invention is a polypeptide represented by SEQ ID No: 10.

In another embodiment, the polypeptide of the present invention is a polypeptide that is a partial peptide of BORIS belonging to isoform A or C or subfamily 5 or 6 and has HLA-A11 antigen-binding capacity. Since the HLA-A11 antigen is an HLA belonging to HLA type I, the polypeptide of the present embodiment preferably has a length of about 8 to about 11 amino acids.

As a result of examining partial peptides of BORIS having HLA-A11 antigen-binding capacity, polypeptides represented by SEQ ID No: 60 to 73 have been identified as epitope peptide candidates. As a result of further investigation into these polypeptides, high CTL inducibility was confirmed for SEQ ID No: 65, SEQ ID No: 66, SEQ ID No: 67, and SEQ ID No: 72. Therefore, in a more preferred embodiment, the polypeptide of the present invention is a polypeptide represented by SEQ ID No: 65, SEQ ID No: 66, SEQ ID No: 67, or SEQ ID No: 72. Among them, a polypeptide represented by SEQ ID No: 72 is more preferable since it is a partial polypeptide of a BORIS sf6 characteristic sequence (SEQ ID No: 1) as described above. In yet another preferred embodiment, the polypeptide of the present invention is a polypeptide represented by SEQ ID No: 65, SEQ ID No: 66, or SEQ ID No: 67; these are also partial peptides of the polypeptide represented by SEQ ID No: 76, and in particular peptides that are present in the zinc finger region. It has been thought that since a conventional BORIS zinc finger region has high homology with CTCF, which is known to be ubiquitously expressed in somatic cells, it would be difficult to obtain a BORIS-specific tumor antigen peptide. Therefore, it is surprising that a zinc finger region-derived BORIS-specific tumor antigen peptide has been obtained from the present research by the present inventors.

In another embodiment, the polypeptide of the present invention is a polypeptide that is a partial peptide of BORIS belonging to isoform A or C or subfamily 5 or 6 and has HLA-A2 antigen and/or HLA-A24 antigen-binding capacity. Since HLA-A2 antigen and HLA-A24 antigen are HLAs belonging to HLA type I, the polypeptide of the present embodiment preferably has a length of about 8 to about 11 amino acids.

As a result of examining BORIS partial peptides having HLA-A2 antigen and/or HLA-A24 antigen-binding capacity, polypeptides represented by SEQ ID No: 3 to 16 and 47 to 57 have been identified as epitope peptide candidates. As a result of further examination of these polypeptides, it has been confirmed that a desirable HLA-binding capacity is shown in SEQ ID No: 3, SEQ ID No: 4, SEQ ID No: 5, SEQ ID No: 10, SEQ ID No: 47, SEQ ID No: 48, and SEQ ID No: 57. Therefore, in a more preferred embodiment, the polypeptide of the present invention is a polypeptide represented by SEQ ID No: 3, SEQ ID No: 4, SEQ ID No: 5, SEQ ID No: 10, SEQ ID No: 47, SEQ ID No: 48, or SEQ ID No: 57. Since, among them, polypeptides represented by SEQ ID No: 3, SEQ ID No: 4, and SEQ ID No: 5 are partial polypeptides of BORIS sf6 characteristic sequence (SEQ No: 1) as described above, they are more preferable. Furthermore, since a polypeptide represented by SEQ ID No: 10 is a partial polypeptide of BORIS sf5 characteristic sequence (SEQ ID No: 2) as described above and has both HLA-A2 antigen and HLA-A24 antigen-binding capacity, it is more preferable. In yet another preferred embodiment, the polypeptide of the present invention is a polypeptide represented by SEQ ID No: 47, SEQ ID No: 48, or SEQ ID No: 57, these also being partial peptides of the polypeptide represented by SEQ ID No: 76. Moreover, among them polypeptides represented by SEQ ID No: 47 and SEQ ID No: 57 are more preferable.

Polypeptides represented by SEQ ID No: 4, SEQ ID No: 5, SEQ ID No: 10, SEQ ID No: 47, SEQ ID No: 48, and SEQ ID No: 57 are particularly preferable. It has been confirmed by research by the present inventors that these polypeptides can induce specific cytotoxic T cells (CTLs).

Among the polypeptides of the present embodiment, examples of polypeptides having HLA-A2 antigen-binding capacity include, but are not limited to, polypeptides represented by SEQ ID No: 4, SEQ ID No: 5, SEQ ID No: 10, SEQ ID No: 47, and SEQ ID No: 57.

Among the polypeptides of the present embodiment, examples of polypeptides having HLA-A24 antigen-binding capacity include, but are not limited to, polypeptides represented by SEQ ID No: 3 and SEQ ID No: 10.

In another embodiment, the polypeptide of the present invention is a polypeptide having one or a plurality of amino acids of the above polypeptide added, deleted, or substituted. Naturally, the polypeptide of the present embodiment is still a polypeptide having HLA-binding capacity, in which one or a plurality of amino acids have been added, deleted, or substituted.

It is known that a peptide having the property of binding to an HLA antigen, an HLA class I antigen in particular, has specific amino acids at specific positions; this is called an anchor motif, and it is thought that HLA-binding capacity is not lost even if an anchor motif is replaced by another anchor motif. Therefore, addition, deletion, and substitution on the polypeptide of the present invention is preferably addition, deletion, and substitution in which an anchor motif is replaced with another anchor motif. For example, it is known that in a polypeptide having the property of binding to an HLA-A11 antigen, any of Ile, Met, Ser, Thr, or Val is often located at the $2^{nd}$ position from the N terminal and either of Lys or Arg is often located at the $9^{th}$ or $10^{th}$ position, and preferred examples of the addition, deletion, and substitution include substitution of Ile at the $2^{nd}$ position from the N terminal with Met, Ser, Thr, or Val.

That is, preferred examples of the addition, deletion, or substitution of the present invention include,
(a) an HLA-A11 antigen-binding peptide having an amino acid at the $2^{nd}$ position from the N terminal changed to Ile, Met, Ser, Thr, or Val;
(b) an HLA-A11 antigen-binding peptide having an amino acid at the $9^{th}$ or $10^{th}$ from the N terminal changed to Lys or Arg;
(c) an HLA-A24 antigen-binding peptide having an amino acid at the $2^{nd}$ position from the N terminal changed to Trp, Phe, Met, or Tyr;
(d) an HLA-A24 antigen-binding peptide having an amino acid at the $9^{th}$ or $10^{th}$ from the N terminal changed to Phe, Leu, Ile, or Trp;
(e) an HLA-A2 antigen-binding peptide having an amino acid at the $2^{nd}$ position from the N terminal changed to Ile, Val, Ala, or Thr; and/or
(f) an HLA-A2 antigen-binding peptide having an amino acid at the $9^{th}$ or $10^{th}$ from the N terminal changed to Val, Leu, Ile, Ala, or Met.

Synthesis of the polypeptide of the present invention may be carried out in accordance with known methods used in usual peptide chemistry. Such known methods include methods described in the literature (Peptide Synthesis, Interscience, New York, 1966; The Proteins, Vol. 2, Academic Press Inc., New York, 1976; Peptide Synthesis, Maruzen Co., Ltd., 1975; Basics and Experiments of Peptide Synthesis, Maruzen Co., Ltd., 1985; Development of Pharmaceuticals Seq. Vol. 14 Peptide Synthesis, Hirokawa Shoten Co., 1991, these publications forming part of the present application by reference), etc.

With regard to the polypeptide of the present invention, in vivo activity can be confirmed by subjecting it to a CTL induction method, which is described later, an assay using a human model animal (WO02/47474, Int J. Cancer: 100, 565-570 (2002)), etc.

Since many cancer cells, including cancer stem cells, express BORIS belonging to isoform A or C or subfamily 5 or 6, the polypeptide of the present invention can be used for inducing a cytotoxic T cell (CTL) that specifically recognizes these cells, as described in the present specification. Therefore, the polypeptide of the present invention is useful for the prevention and/or treatment of a cancer, etc., and may be an active ingredient of a pharmaceutical composition. In particular, since the present inventors have found that among BORIS subfamilies, sf5 and/or sf6 are specifically expressed in cancer stem cells, the polypeptide of the present invention that is derived from an amino acid sequence characteristic of such a subfamily can be particularly suitably used in a pharmaceutical composition for treating cancer stem cells. Furthermore, the polypeptide of the present invention may be one for the prevention and/or treatment of a cancer. Moreover, the present invention also relates to use of the polypeptide of the present invention in the production of a pharmaceutical for the prevention and/or treatment of a cancer.

(2) Polynucleotide of the Present Invention

The polynucleotide of the present invention includes a polynucleotide that encodes at least one of the polypeptides of the present invention. The polynucleotide of the present invention may be any of cDNA, mRNA, cRNA, or synthetic DNA. It may have either a single-strand or a double-strand configuration. Specific examples include a polynucleotide comprising a nucleotide sequence expressiblly encoding an amino acid sequence described in SEQ ID No: 3, SEQ ID No: 4, SEQ ID No: 5, SEQ ID No: 10, SEQ ID No: 47, SEQ ID No: 48, SEQ ID No: 57, SEQ ID No: 65, SEQ ID No: 66, SEQ ID No: 67, or SEQ ID No: 72. In one embodiment, the polynucleotide of the present invention is used for producing the polypeptide of the present invention within a host using a gene recombination technique. In this case, since the frequency of amino acid codon usage is different between hosts, the amino acid codon may be changed so as to conform to the frequency of usage in the host in which production is carried out.

The polynucleotide of the present invention may take on either a single strand or a double strand configuration. When the polynucleotide of the present invention is a double strand, a recombinant expression vector expressing the polypeptide of the present invention may be produced by inserting the polynucleotide of the present invention into an expression vector. That is, the scope of the polynucleotide of the present invention includes a recombinant expression vector produced by inserting the double strand polynucleotide of the present invention into an expression vector.

The polynucleotide of the present invention is useful for the prevention and/or treatment of a cancer, etc. as described in the present specification, and may be an active ingredient of a pharmaceutical composition. Furthermore, the polynucleotide of the present invention may be one for the prevention and/or treatment of a cancer. Moreover, the present invention also relates to use of the polynucleotide of the present invention in the production of a pharmaceutical for the prevention and/or treatment of a cancer.

With regard to the expression vector used in the present invention, various types may be used according to the host used, the intended application, etc., and a person skilled in the art may select it as appropriate. Examples of expression vectors that can be used in the present invention include a plasmid, a phage vector, a virus vector, a cosmid vector, a fosmid vector, and an artificial chromosome vector (HAC, YAC, BAC, PAC). For example, when the host is *Escherichia coli*, examples of the vector include plasmid vectors such as pUC118, pUC119, pBR322, pCR3, and pGATA and phage vectors such as λZAPII and λgt11. When the host is a yeast, examples of the vector include pYES2, pYEUra3, and pYAC4. When the host is an insect cell, examples include pAcSGHisNT-A, pIEx, and pBAC. When the host is an animal cell, examples include plasmid vectors such as pCEP4, pKCR, pCDM8, pGL2, pcDNA3.1, pRc/RSV, and pRc/CMV and virus vectors such as a retrovirus vector, an adenovirus vector, an adeno-associated virus vector, a vaccinia vector, a Sendai virus vector, and a lentivirus vector.

The vector may have as appropriate a factor such as a promoter that can induce expression, a gene encoding a signal sequence, a selection marker gene, or a terminator. Furthermore, in order to make isolation and purification easy, a sequence for expression as a fusion protein with thioredoxin, a His tag, GST (glutathione S-transferase), etc. may be added. In this case, a GST fusion protein vector (pGEX4T, etc.) having an appropriate promoter (lac, tac, trc, trp, CMV, SV40 early promoter, etc.) that functions within a host cell, a vector having a tag sequence such as Myc or His (pcDNA3.1/Myc-His, etc.) and, furthermore, a vector expressing a fusion protein with thioredoxin and a His tag (pET32a), etc. may be used.

Transforming a host with the expression vector prepared as above enables a transformed cell containing the expression vector to be prepared. The host used here may be any cell as long as the function of the polypeptide of the present invention is not impaired, and examples include a bacterium such as an *Escherichia coli* or attenuated *Salmonella*, a yeast, an insect cell, and an animal cell. Examples of the *Escherichia coli* include *E. coli* K-12 strain HB101, C600, JM109, DH5α, AD494 (DE3), and BL21. Examples of the yeast include *Saccharomyces cerevisiae*. Examples of the animal cell include L929 cells, BALB/c3T3 cells, C127 cells, CHO cells, COS cells, Vero cells, HeLa cells, and 293-EBNA cells. Examples of the insect cell include sf9, Hi5, and S2.

As a method for introducing the expression vector into the host cell, a standard introduction method suitable for the host cell may be used. Specific examples include a calcium phosphate method, a DEAE-dextran method, an electroporation method, and a method (lipofection method) using a gene transfer lipid (Lipofectamine, Lipofectin; Gibco-BRL). After introduction, culturing is carried out in a standard medium containing a selection marker, thus enabling a transformed cell in which the expression vector has been introduced into the host cell to be selected.

Continuing culturing the transformed cell thus obtained under suitable conditions enables the polypeptide of the present invention to be produced. The polypeptide thus obtained may be further isolated and purified by usual biochemical purification means. Examples of the purification means include salting out, ion-exchange chromatography, adsorption chromatography, affinity chromatography, and gel permeation chromatography. When the polypeptide of the present invention is expressed as a fusion protein with thioredoxin, a His tag, a GST, etc. as described above, isolation and purification may be carried out by a purification method utilizing the properties of the fusion protein or the tag. Furthermore, when a bacterium such as attenuated *Salmonella* is used as the host cell, this bacterium may be used as a gene delivery carrier, that is, a bacterium as a host cell may be directly delivered into the body of a subject.

The polynucleotide encoding the polypeptide of the present invention may have a DNA configuration or an RNA configuration. These polynucleotides of the present invention may be easily produced by standard methods known in the present technical field based on amino acid sequence information of the polypeptide of the present invention and information on the DNA sequence encoded thereby. Specifically, they may be produced by standard DNA synthesis, amplification by means of PCR, etc.

The polynucleotide encoding the polypeptide of the present invention includes a polynucleotide encoding the epitope peptide.

(3) CTL Inducer Having Polypeptide of the Present Invention as Active Ingredient Since as described above the polypeptide of the present invention can be used in a method for inducing a CTL for a cancer cell, it can be a CTL inducer as a tumor antigen peptide.

That is, peripheral blood lymphocytes are isolated from a human blood sample, they are stimulated in vitro by adding the polypeptide of the present invention, and CTLs that specifically recognize HLA antigen-positive cells that have been pulsed with the peptide can be induced (J. Immunol., 154, p. 2257, 1995). The presence or absence of CTL induction may be confirmed by measuring for example the amount of various cytokines (for example IFNγ) produced by CTLs when reacting with antigen peptide-presenting cells, by means of for example an ELISA method, etc. It may also be confirmed by a method for measuring CTL toxicity toward antigen peptide-presenting cells labeled with $^{51}$Cr ($^{51}$Cr release assay, Int. J. Cancer, 58: p 317, 1994).

Furthermore, a CTL clone may be established by a method described in Int. J. Cancer, 39, 390-396, 1987, N. Eng. J. Med, 333, 1038-1044, 1995, etc.

A CTL induced by the polypeptide of the present invention has a cytotoxic action toward a cell presenting the polypeptide of the present invention as an antigen and the ability to produce a lymphokine. Since the polypeptide of the present invention is a tumor antigen peptide as described above, it can exhibit an anti-tumor action, and preferably an anti-cancer action, via the above functions. Therefore, the polypeptide of the present invention and a CTL induced thereby can be an active ingredient of a pharmaceutical or a pharmaceutical composition for the prevention and/or treatment of a cancer.

When a CTL inducer containing the polypeptide of the present invention as an active ingredient is administered to a cancer patient, the polypeptide of the present invention is presented to an HLA antigen of an antigen-presenting cell, a CTL that is specific to a complex between the HLA antigen and the presented peptide proliferates and destroys the cancer cells, and as a result the cancer can be prevented and/or treated. Therefore, a CTL inducer containing the polypeptide of the present invention as an active ingredient can preferably be used for a subject who is positive for an HLA-A02 antigen, an HLA-A11 antigen, and/or an HLA-A24 antigen. It may more preferably used for a subject having a cancer expressing BORIS belonging to isoform A or C or subfamily 5 or 6, and yet more preferably a subject having a BORIS sf5 and/or sf6-positive cancer. Examples of a cancer that is positive for BORIS belonging to isoform A or C or subfamily 5 or 6 include a cancer (tumor) such as cervical cancer, ovarian cancer, uterine cancer, breast cancer, colon cancer, lung cancer, or melanoma, and the CTL inducer of the present invention may be used for the prevention and/or treatment of such cancers. In particular, it may preferably be used in the prevention and/or treatment of a cancer of the lung and a cancer in a female-specific organ, such as cervical cancer, ovarian cancer, or uterine cancer.

The 'prevention' of a cancer referred to here includes not only preventing a patient from having a cancer but also prevention of recurrence in a patient who has been subjected to surgery to remove a primary tumor and prevention of metastasis of a tumor that could not be completely removed by a cancer treatment such as surgery, radiotherapy, or drug therapy. Furthermore, the 'treatment' of a cancer includes not only curing and improvement of the symptoms of a cancer that reduces the size of the cancer but also prevention of progress by suppressing cancer cell proliferation, tumor enlargement, or metastasis of cancer cells from a primary focus.

A CTL inducer containing the polypeptide of the present invention as an active ingredient is particularly effective for an HLA-A02-, HLA-A11-, or HLA-A24-positive cancer patient who has a cancer positive for BORIS belonging to isoform A or C or subfamily 5 or 6, and preferably BORIS sf5 and/or sf6. Specifically, it may be used for the prevention or treatment of a cancer (tumor) such as for example cervical cancer, ovarian cancer, uterine cancer, breast cancer, colon cancer, lung cancer, or melanoma. In particular, it may preferably be used for the prevention and/or treatment of a cancer in a female-specific organ, such as cervical cancer, ovarian cancer, or uterine cancer.

The preparation form of a CTL inducer containing the polypeptide of the present invention as an active ingredient is not particularly limited, and examples include an oil emulsion (emulsion preparation), macromolecular nanoparticles, a liposome preparation, a particulate preparation bonded to beads having a diameter of a few μm, a lipid-bonded preparation, a microsphere preparation, and a microcapsule preparation.

A CTL inducer containing the polypeptide of the present invention as an active ingredient may be administered as a mixture with a pharmaceutically acceptable carrier, for example an appropriate adjuvant, or in combination therewith, so as to establish cell-mediated immunity effectively.

As the adjuvant, an adjuvant known in the present technical field may be applied, and specific examples include a gel type such as aluminum hydroxide, aluminum phosphate, or calcium phosphate, a bacterial type such as CpG, monophosphoryl lipid A (monophosphoryl lipid A; MPL), cholera toxin, *Escherichia coli* heat-labile toxin, pertussis toxin, or muramyl dipeptide (Muramyl dipeptide; MDP), an oil emulsion type (emulsion preparation) such as Freund's incomplete adjuvant, MF59, or SAF, a macromolecular nanoparticle type such as an immunostimulatory complex (Immunostimulatory complex; ISCOMs), a liposome, biodegradable microspheres (Biodegradable microsphere), or saponin-derived QS-21, a synthetic type such as a nonionic block copolymer, a muramyl peptide analog (Muramyl peptide analogue), a polyphosphazene, or a synthetic polynucleotide, and a cytokine type such as IFN-α, IFN-β, IFN-γ, IL-2, or IL-12.

Examples of an administration method include any known administration method such as intradermal administration, subcutaneous administration, intramuscular administration, or intravenous administration. The dose of the polypeptide of the present invention in a preparation may be adjusted as appropriate according to the target disease to be treated, the age and body weight of the patient, etc., but it is usually 0.0001 mg to 1000 mg, preferably 0.001 mg to 1000 mg, and more preferably 0.1 mg to 10 mg, this being preferably administered once in a few days or a few months.

As described above, due to the use of a CTL inducer containing the polypeptide of the present invention as an active ingredient, a cancer that is positive for BORIS belonging to isoform A or C or subfamily 5 or 6 can be treated effectively. Therefore, in one embodiment the present invention comprises a pharmaceutical composition containing the CTL inducer as an active ingredient, and preferably a composition for the treatment of cancer stem cells or a composition for the prevention and/or treatment of a cancer.

(4) CTL Inducer Containing Polynucleotide of the Present Invention as Active Ingredient Since a cell in which the polynucleotide of the present invention is expressed becomes a cell that presents the polypeptide of the present invention as an antigen, it has the feature that it is recognized by a T cell via a T cell receptor. Therefore, the polynucleotide of the present invention can also become a CTL inducer. An induced CTL can exhibit, in the same way as for a CTL induced by the polypeptide of the present invention, an anti-tumor action, and preferably an anti-cancer action, via cytotoxic action or lymphokine production. Therefore, the polynucleotide of the present invention can be an active ingredient of a pharmaceutical or a pharmaceutical composition for the treatment or prevention of a cancer. A CTL inducer containing the polynucleotide of the present invention as an active ingredient enables a cancer to be treated and/or prevented by for example administering the polynucleotide of the present invention to a cancer patient so that expression takes place.

For example, when the polynucleotide of the present invention incorporated into an expression vector is administered to a cancer patient by the method below, a tumor antigen peptide is highly expressed within antigen-presenting cells. The tumor antigen peptide thus produced subsequently binds to an HLA-A02 antigen, an HLA-A11 antigen, an HLA-A24 antigen, etc. to form a complex, this complex is presented at high density on the antigen-presenting cell surface, cancer-specific CTLs thereby proliferate efficiently in the body, and the cancer cells are destroyed. As described above, the treatment or prevention of a cancer is achieved.

The CTL inducer containing the polynucleotide of the present invention as an active ingredient may preferably be used for an HLA-A02 antigen-, HLA-A11 antigen-, and/or HLA-A24 antigen-positive subject. It may preferably be used for a subject having a cancer expressing BORIS belonging to isoform A or C or subfamily 5 or 6, and more preferably a subject having a BORIS sf5- and/or sf6-positive cancer. Examples of cancers that are positive for BORIS belonging to isoform A or C or subfamily 5 or 6 include cancers (tumors) such as cervical cancer, ovarian cancer, uterine cancer, breast cancer, colon cancer, lung cancer, and melanoma, and the CTL inducer of the present invention may be used for the prevention or treatment of these cancers. In particular, it may preferably be used for the prevention and/or treatment of lung cancer and a cancer in a female-specific organ, such as cervical cancer, ovarian cancer, or uterine cancer.

Examples of the method involving the virus vector include a method in which the DNA of the present invention is integrated into for example a DNA virus or RNA virus such as a retrovirus, adenovirus, adeno-associated virus, herpes virus, vaccinia virus, Sendai virus, lentivirus, poxvirus, poliovirus, or sindbis virus, and incorporation is carried out. Among them, a method involving a retrovirus, adenovirus, adeno-associated virus, vaccinia virus, etc. is particularly preferable.

Examples of other methods include a method in which an expression plasmid is directly administered intramuscularly (DNA vaccine method), a liposome method, a lipofection method, a microinjection method, a calcium phosphate method, and an electroporation method, and a DNA vaccine method and a liposome method are particularly preferable. Furthermore, a bacterial vector method in which an expression plasmid is introduced into a bacterium such as attenuated *Salmonella*, and the bacterium is administered to thus make the polypeptide of the present invention be expressed may also be used.

When the polynucleotide of the present invention is administered, administration may be carried out by selecting as appropriate an administration route and an administration form according to the target disease to be treated, the symptoms, etc. For example, administration may be carried out in a form that can be injected into a vein, an artery, subcutaneously, intradermally, intramuscularly, etc. When administration is carried out, for example, a preparation form such as a liquid may be employed, but it is usually made into an injection, etc. containing the polynucleotide of the present invention, which is an active ingredient, and a pharmaceutically acceptable carrier (carrier) may be added as necessary. With regard to a liposome or a membrane fusion liposome (Sendai virus (HVJ)-liposome, etc.) containing the polynucleotide of the present invention, a liposome preparation such as a suspension, a frozen agent, or a centrifugation-concentrated frozen agent may be employed.

The content of the polynucleotide of the present invention in a preparation may be adjusted as appropriate according to the target disease to be treated, the age and body weight of the patient, etc.; it may be for example 0.0001 mg to 100 mg as a polynucleotide content, and preferably 0.001 mg to 10 mg of the polynucleotide of the present invention, it being administered once in a few days or a few months.

A person skilled in the art can appropriately select a suitable cell, vector, administration method, administration form, and dose.

(5) Antigen-Presenting Cell of the Present Invention

The polypeptide or the polynucleotide of the present invention described above may be utilized in the treatment of a cancer patient, for example in vitro, as follows. That is, either the polypeptide or the polynucleotide of the present invention and cells having antigen-presenting ability are brought into contact with each other, thus enabling antigen-presenting cells to be prepared. Preparation of the antigen-presenting cells may be carried out in vitro or in vivo, but it is preferably carried out in vitro. Specifically, the present invention provides an antigen-presenting cell presenting a complex between for example an HLA-A02 antigen, an HLA-A11 antigen, or an HLA-A24 antigen and the polypeptide of the present invention on the cell surface of a cancer patient-derived isolated cell having antigen-presenting ability preferably by bringing the cell into contact with either the polypeptide or the polynucleotide of the present invention in vitro, and a method for producing same.

Examples of the antigen-presenting cell of the present invention include (1) an epitope peptide-pulsed antigen-presenting cell formed by mixing the antigen-presenting cell and the CTL epitope peptide in an appropriate culture liquid for 30 minutes to 1 hour, (2) a cell in which a CTL epitope peptide is presented by an antigen-presenting cell by means of gene transfer, etc. using nucleic acids encoding the CTL epitope peptide, and (3) an artificially prepared artificial antigen-presenting cell having antigen-presenting ability.

The 'cell having antigen-presenting ability' referred to here is not particularly limited as long as it is a cell expressing on the cell surface an MHC, preferably an HLA-A02 antigen, an HLA-A11 antigen, and/or an HLA-A24 antigen, that can present the polypeptide of the present invention, and among them it is preferably a professional antigen-presenting cell, and particularly preferably a dendritic cell, which is considered to have high antigen-presenting ability. An artificially prepared artificial antigen-presenting cell having antigen-presenting ability can be prepared by for example fixing a complex of three components, that is, an HLA, a CTL epitope peptide, and $\beta$2-microglobulin, to a lipid bilayer or a plastic, latex, etc. bead and fixing a costimulator such as CD80, CD83, or CD86 that can stimulate CTLs, or fixing an antibody, etc. that agonistically acts on CD28, which is a ligand on the T cell side that binds to a costimulator.

Furthermore, with regard to a substance that is added in order to prepare the antigen-presenting cell of the present invention from the cell having antigen-presenting ability, it may be either the polypeptide or the polynucleotide of the present invention.

The antigen-presenting cell of the present invention is obtained by for example isolating cells having antigen-presenting ability from a cancer patient, and pulsing the cells with the polypeptide of the present invention in vitro so as to make them present a complex between an HLA-A02 antigen, an HLA-A11 antigen, and/or an HLA-A24 antigen and the polypeptide of the present invention. When dendritic cells are used, for example, lymphocytes are separated from the peripheral blood of a cancer patient by the Ficoll method, non-adherent cells are then removed, adherent cells are cultured in the presence of GM-CSF and IL-4 to thus induce dendritic cells, and the dendritic cells are pulsed by culturing together with the polypeptide of the present invention, thus enabling the antigen-presenting cell of the present invention to be prepared.

Furthermore, when the antigen-presenting cell of the present invention is prepared by introducing the polynucleotide of the present invention into the cell having antigen-presenting ability, the polynucleotide may be in the form of a DNA or the form of an RNA. Methods for preparing an antigen-presenting cell by introducing a polynucleotide are known in the art, and a person skilled in the art may select a method as appropriate.

The antigen-presenting cell can be an active ingredient of the CTL inducer. The CTL inducer containing the antigen-presenting cell as an active ingredient preferably contains physiological saline, phosphate buffered physiological saline (PBS), a medium, etc. in order to maintain the antigen-presenting cell stably. Examples of an administration method include intravenous administration, subcutaneous administration, and intradermal administration. Returning a CTL inducer containing such an antigen-presenting cell as an active ingredient to the body of the patient enables a CTL that is specific to a cancer cell presenting the polypeptide of the present invention as an antigen to be efficiently induced in the body of a patient having a cancer that is positive for BORIS belonging to isoform A or C or subfamily 5 or 6, and as a result a cancer that is positive for BORIS belonging to isoform A or C or subfamily 5 or 6 and that presents the polypeptide of the present invention as an antigen can be treated.

(6) Cytotoxic T Cell (CTL) of the Present Invention

The peptide and the polynucleotide of the present invention may be utilized in the treatment of a cancer patient as follows. That is, a CTL, in particular a CTL that specifically recognizes a cell expressing a BORIS gene belonging to isoform A or C or subfamily 5 or 6, may be induced by bringing either the polypeptide or the polynucleotide of the present invention into contact with peripheral blood lymphocytes. That is, the present invention provides a CTL that is induced by bringing either the polypeptide or the polynucleotide of the present invention into contact with peripheral blood lymphocytes derived from a cancer patient, and a method for carrying out the induction. Such a method may be carried out in vitro or in vivo, but it is preferably carried out in vitro.

Specific examples of the method for inducing a CTL of the present invention include the method below. First, PBMCs or T cells are directly stimulated with the polypeptide of the present invention or stimulated with antigen-presenting cells pulsed with the peptide, gene transferred antigen-presenting cells, or artificially prepared artificial antigen-presenting cells having antigen-presenting ability. CTLs that have been induced by stimulation are cultured in a 5% $CO_2$ incubator at 37° C. for 7 to 10 days. The required CTL cell count is secured by repeating stimulation with a CTL epitope peptide and IL-2 or with antigen-presenting cells and IL-2 once a week.

In a melanoma for example, it has been confirmed that an adoptive immunotherapy in which a large number of intratumoral infiltrating T cells from the patient in question are cultured in vitro and returned to the patient has a therapeutic effect. Furthermore, in a mouse melanoma it has been confirmed that metastasis is suppressed by stimulating spleen cells in vitro with TRP-2 tumor antigen peptide so as to make CTLs specific to the tumor antigen peptide proliferate and administering the CTLs to a melanoma-transplanted mouse. This is based on the result that CTLs that specifically recognize a complex between a tumor antigen peptide and an MHC of an antigen-presenting cell proliferate in vitro. It is therefore considered that a therapy in which peripheral blood lymphocytes of a patient are stimulated in vitro using the polypeptide or the polynucleotide of the present invention to thus increase tumor-specific CTLs and the CTLs are subsequently returned to the patient will be useful.

The CTLs may be an active ingredient of a treatment agent or a preventive agent for a cancer. The treatment agent or the preventive agent preferably contains physiological saline, phosphate buffered physiological saline (PBS), a medium, etc. in order to stably maintain the CTLs. Examples of administration methods include intravenous administration, subcutaneous administration, and intradermal administration. Returning the cancer treatment or preventive agent containing such CTLs as an active ingredient to the body of a patient enables the cytotoxicity of the CTLs to cancer cells in the body of a patient having a cancer that is positive for BORIS belonging to isoform A or C or subfamily 5 or 6 of the present invention to be promoted, and the cancer to be treated by destroying the cancer cells.

(7) HLA-Multimer of the Present Invention

An HLA-tetramer refers to a tetramer formed by biotinylating a complex (HLA-monomer) in which an HLA and β2 microglobulin are associated with a peptide (antigen peptide) and binding it to avidin (Science 279: 2103-2106 (1998), Science 274: 94-96 (1996)) and is described in for example U.S. Pat. No. 5,635,363, French Patent Laid-open No. FR9911133, U.S. Pat. Nos. 5,723,584, 5,874,239, 5,932,433, 6,265,552, Registered Japanese Patent No. 4976294, etc. HLA-tetramers containing various types of antigen peptides are now being prepared, and an HLA-tetramer containing the polypeptide of the present invention and HLA-A02, HLA-A11, or HLA-A24 can be easily prepared. Furthermore, an HLA-dimer and an HLA-pentamer are also based on the same principle, the HLA monomer being formed into the dimer and the pentamer respectively. Therefore, an HLA monomer and an HLA multimer, in particular an HLA-tetramer, containing HLA-A02, HLA-A11, or HLA-A24 and the polypeptide of the present invention, that is, a partial peptide of BORIS belonging to isoform A or C or subfamily 5 or 6 having HLA-binding capacity, in particular HLA class I binding capacity, are also one embodiment of the present invention.

Specific examples include an HLA-tetramer containing the polypeptide of the present invention and HLA-A02, HLA-A11, or HLA-A24. The HLA-tetramer is preferably fluorescently labeled so that bound CTLs can be easily selected or detected by known detection means such as flow cytometry or a fluorescence microscope. Specific examples include HLA-tetramers labeled with phycoerythrin (PE), fluorescein isothiocyanate (FITC), peridinin chlorophyll protein (PerCP), etc.

Examples of an HLA-tetramer production method include those described in U.S. Pat. No. 5,635,363, French Patent Application No. FR9911133, Science 279: 2103-2106 (1998), Science 274: 94-96 (1996), etc., and a person skilled in the art can select an appropriate method. A preparation example is described in brief below.

First, an HLA-A24, HLA-A11, or HLA-A02 expression vector and a β2 microglobulin expression vector are introduced into *Escherichia coli* or mammalian cells that can express a protein and expression is carried out. Here, it is preferable to use *Escherichia coli* (for example, BL21). The monomer HLA-A24, HLA-A11, or HLA-A02 complex thus obtained and the polypeptide of the present invention are mixed to thus form a soluble HLA-peptide complex. Subsequently, the C terminal site sequence of the HLA-A02, HLA-A11, or HLA-A24 in the HLA-peptide complex is biotinylated with BirA enzyme. This biotinylated HLA-peptide complex and fluorescently-labeled avidin are mixed at a molar ratio of 4:1, thus preparing an HLA tetramer. In each of the above steps, it is preferable to carry out protein purification by means of gel filtration, etc.

Due to the use of the HLA-tetramer (or monomer) of the present invention, the tumor specific CTLs of the present invention can be detected and purified. Examples of methods for forming CTLs include the methods below.

(i) PBMCs and an appropriate concentration of the HLA-tetramer of the present invention are reacted. Since the CTL binding to the HLA-tetramer of the present invention is stained with a labeling dye, only CTLs that have been stained are isolated using a cell sorter, a microscope, etc. Proliferation of the CTLs thus isolated is stimulated with a T cell-stimulating agent such as an anti-CD3 antibody, PHA, or IL-2 or with antigen-presenting cells whose proliferative capacity has been lost by X-ray irradiation, mitomycin treatment, etc., thus giving the required number of cells.

(ii) The HLA-monomer and/or tetramer of the present invention is made into a solid phase on a sterile plate, etc., and PBMCs are cultured on the solid phase plate. In order to isolate CTLs binding to the HLA-monomer and/or tetramer of the present invention made into a solid phase on the plate, after other unbound floating cells are washed away, only specific CTLs remaining on the plate are suspended in a new medium. Proliferation of the CTLs thus isolated is stimulated with a T cell-stimulating agent such as an anti-CD3 antibody, PHA, or IL-2 or with antigen-presenting cells whose proliferative capacity has been lost by X-ray irradiation, mitomycin treatment, etc., thus giving the required number of cells.

(iii) The HLA-monomer and/or tetramer of the present invention and a costimulator such as CD80, CD83, or CD86 or an antibody that agonistically acts on CD28, which is a ligand on the T cell side binding to a costimulator, etc. are made into a solid phase on a sterile plate, and PBMCs are cultured on the solid phase plate. 2 days later, IL-2 is added to the medium, and culturing is carried out in a 5% $CO_2$ incubator at 37° C. for 7 to 10 days. The cultured cells are collected and culturing is continued on a fresh solid phase plate. This procedure is repeated, thus giving the required number of CTL cells.

By the use of an antibody to a cell surface protein (CD62L, CCR7, CD45RA, etc.) in combination, the CTL differentiation stage can be examined (Seder R A, Ahmed R., Nat Immunol., 2003; 4: 835-842). Alternatively, by combination with intracellular cytokine staining, it can be used also for evaluation of CTL function. Therefore, by identifying a CTL epitope peptide and preparing an HLA-tetramer it becomes possible to quantitatively and qualitatively determine CTL induction for the epitope peptide, and it is possible to contribute greatly to obtaining diagnostic information concerning a disease in which a protein from which the epitope peptide is derived is involved.

(8) Tumor Detection Method (Test Method, Diagnostic Method)

The present invention also provides a tumor detection method (test method, diagnostic method) utilizing the HLA-tetramer of the present invention.

The detection method (diagnostic method) of the present invention using the HLA-tetramer of the present invention typically involves harvesting a test subject's blood or harvesting some of the test tissue for which a tumor is suspected by means of a biopsy, etc., and detecting/measuring the amount of CTLs that recognize a complex between an HLA antigen and a tumor antigen peptide derived from BORIS belonging to isoform A or C or subfamily 5 or 6 by means of the HLA-tetramer of the present invention, thus detecting, testing, or diagnosing the presence or absence or the extent of a cancer (tumor) that is positive for BORIS belonging to isoform A or C or subfamily 5 or 6 such as cervical cancer, ovarian cancer, uterine cancer, breast cancer, colon cancer, lung cancer, or melanoma. In particular, it is possible to detect, test, or diagnose the presence or absence or the extent of a disease such as lung cancer or a cancer in a female-specific organ, such as cervical cancer, ovarian cancer, or uterine cancer.

CTL specific to BORIS, in particular BORIS belonging to isoform A or C or subfamily 5 or 6, in a biological sample harvested from a subject can be quantitatively determined using the HLA-tetramer of the present invention. Quantitative determination may be carried out for example as follows. Peripheral blood or PBMCs harvested from a subject is reacted with an appropriate concentration of HLA-tetramer. Since CTLs binding to the HLA-tetramer are stained with a labeling dye, they are counted using a flow cytometer, a microscope, etc. When reacted with the HLA-tetramer reagent, reaction with an anti-CD3 antibody, anti-CD4 antibody, anti-CD8 antibody, etc. that has been labeled with a dye different from the HLA-tetramer reagent enables T cell subsets of the BORIS-specific CTLs to be determined at the same time.

For example, the detection (test, diagnostic) method of the present invention can detect (test, diagnose) the presence or absence or the extent of improvement of a tumor when a therapeutic drug is administered to a patient having a tumor in order to improve the tumor. Furthermore, the detection (test, diagnostic) method of the present invention may be applied to the selection of a cancer patient to whom a pharmaceutical containing the polypeptide or the polynucleotide of the present invention as an active ingredient can be applied effectively, and to the prediction, assessment, etc. of the therapeutic effect of the pharmaceutical.

A specific embodiment of the detection (test) method of the present invention using the HLA-tetramer of the present invention includes steps (a) and (b), and optionally step (c), as follows:

(a) a step of bringing a biological sample obtained from a test subject into contact with the HLA-tetramer of the present invention, (b) a step of measuring the amount of CTLs that recognize a complex between an HLA antigen and a BORIS sf5- or sf6-derived tumor antigen peptide in the biological sample using the amount of cells to which the HLA-tetramer binds as an indicator, and (c) a step of determining the presence of a cancer based on the result of (b).

A specific embodiment of the diagnostic method of the present invention using the HLA-tetramer of the present invention includes steps (a), (b), and (c) above.

One embodiment of the detection method (test method, diagnostic method) of the present invention using the HLA-tetramer of the present invention is carried out by detecting CTLs specific to the polypeptide of the present invention in a biological sample and measuring the amount thereof. For example, the HLA-tetramer of the present invention is prepared, and this can be used for quantitatively determining by means of a flow cytometer the amount of antigen peptide-specific CTLs in peripheral blood lymphocytes of a patient for whom a cancer is suspected.

The prediction, assessment, determination, or diagnosis of the presence or absence of a tumor may be carried out by, for example, measuring the amount of CTLs specific to the polypeptide of the present invention in a test subject's blood or test tissue for which a tumor is suspected or the amount of cells presenting the polypeptide of the present invention. In this process, depending on the circumstances, the level of expression of the BORIS gene or mRNA of BORIS belonging to isoform A or C or subfamily 5 or 6, the level of the polypeptide of the present invention, or the level of CTLs, etc. in corresponding normal tissue may be used as a reference value, and this reference value may be compared with the level in the sample obtained from the test subject, the difference between the two being assessed.

Here, the comparison of the levels between the test tissue of the test subject and the corresponding normal tissue may be carried out by measuring a biological sample of the test subject and a biological sample of a healthy subject in parallel. When it is not carried out in parallel, the average value or the statistical median of the amounts of CTLs specific to the polypeptide of the present invention obtained using a plurality (at least two, preferably at least three, and more preferably at least five) of normal tissue pieces under uniform measurement conditions may be used in the comparison as the value for a healthy subject, that is, a reference value.

Furthermore, in a test subject to which the polypeptide or the polynucleotide of the present invention is administered, it is also possible by measuring the amount of CTLs specific to the polypeptide of the present invention to assess whether or not CTLs have actually been induced. For example, it is possible to assess whether the treatment with the polypeptide or the polynucleotide of the present invention is effective by using as an indicator the amount of CTLs specific to the polypeptide of the present invention in the tissue of the test subject being for example at least twice the level thereof of a healthy subject, and preferably at least three times.

(9) Preventive and/or Therapeutic Method for Cancer

The present invention also relates to a method for preventing and/or treating a cancer in a subject, the method including a step of administering an effective amount of an active ingredient selected from the group consisting of the polypeptide, the polynucleotide, the CTL, and the antigen-presenting cell of the present invention to a subject requiring same.

The 'subject' in the present invention means any biological individual, preferably an animal, more preferably a mammal, and more preferably a human individual. In the present invention, the subject may be healthy or may have any disease, but when the prevention and/or treatment of a cancer is intended, it typically means a subject having a cancer or having a risk thereof. In one embodiment of the present invention, the subject is HLA-A02 positive, HLA-A11 positive, and/or HLA-A24 positive. In one embodiment of the present invention, the subject has a cancer that is positive for BORIS belonging to isoform A or C or subfamily 5 or 6 or has a risk thereof. In one embodiment of the present invention, the subject is HLA-A02 positive, HLA-A11 positive, and/or HLA-A24 positive and has a cancer that is positive for BORIS belonging to isoform A or C or subfamily 5 or 6 or has a risk thereof.

With regard to the polypeptide, the polynucleotide, the CTL, and the antigen-presenting cell of the present invention used in the preventive/therapeutic method of the present invention, any one described in the present specification can be cited. The effective amount referred to in the present invention is an amount that for example reduces the symptoms of a cancer or delays or halts the progress thereof, and is preferably an amount that suppresses or cures a cancer. Furthermore, it is preferably an amount that does not cause an adverse effect that exceeds the benefit obtained by administration. Such an amount may be determined as appropriate by means of an in vitro test using cultured cells, etc. or a test in a model animal such as a mouse or a rat, and such test methods are well known to a person skilled in the art. The specific dose of an active ingredient may be determined while taking into consideration various conditions related to a subject requiring same, for example, the seriousness of symptoms, the general health state, age, and body weight of the subject, the sex of the subject, diet, timing and frequency of administration, concomitant medication, response to treatment, dosage form, compliance with treatment, etc.

In the case of for example the polypeptide of the present invention, the specific dose is usually 0.0001 mg to 1000 mg, preferably 0.001 mg to 1000 mg, and more preferably 0.1 mg to 10 mg, and this is preferably administered once in a few days or a few months. Furthermore, in the case of the polynucleotide of the present invention, it is usually 0.0001 mg to 100 mg, and preferably 0.001 mg to 10 mg, and this is administered once in a few days or a few months. As an administration method, any known appropriate administration method such as intradermal administration, subcutaneous administration, intramuscular administration, or intravenous administration may be used.

One embodiment of the preventive/therapeutic method of the present invention further includes, prior to the administration step, a step of selecting a subject who is HLA-A02 positive, HLA-A11 positive, and/or HLA-A24 positive as the subject for the prevention/treatment. This embodiment of the present invention may further include, prior to the selection step, a step of determining the HLA type of a subject. Determination of the HLA type of a subject may be carried out by any known method. Furthermore, one embodiment of the preventive/therapeutic method of the present invention further includes, prior to the administration step, a step of selecting a subject having a cancer that is positive for BORIS belonging to isoform A or C or subfamily 5 or 6 as a subject for the prevention/treatment. This embodiment of the present invention may further include, prior to the selection step, a step of detecting a cancer that is positive for BORIS belonging to isoform A or C or subfamily 5 or 6 in a subject. Detection of a cancer that is positive for BORIS belonging to isoform A or C or subfamily 5 or 6 in a subject may employ the tumor detection method described in (8) above. One embodiment of the preventive/therapeutic method of the present invention further includes, prior to the administration step, a step of selecting a subject who is HLA-A02 positive, HLA-A11 positive, and/or HLA-A24 positive and has a cancer that is positive for BORIS belonging to isoform A or C or subfamily 5 or 6 as a subject for the prevention/treatment. This embodiment of the present invention may further include, prior to the selection step, a step of determining the HLA type of a subject and a step of detecting a cancer that is positive for BORIS belonging to isoform A or C or subfamily 5 or 6 in a subject.

All patents, applications, and other publications referred to in the present specification are incorporated herein by reference in their entirety.

(10) Antibody of the Present Invention

The present invention also provides an antibody that specifically binds to at least part of BORIS belonging to isoform A or C or subfamily 5 or 6, preferably at least part of a polypeptide represented by SEQ ID No: 1, SEQ ID No: 2 or SEQ ID No: 76, and more preferably at least part of a polypeptide represented by SEQ ID No: 1 or SEQ ID No: 2. Therefore, the antibody of the present invention can preferably specifically recognize BORIS belonging to subfamily or 6. The antibody may be a polyclonal antibody or a monoclonal antibody, but is preferably a monoclonal antibody.

Furthermore, the antibody of the present invention also includes antibody functional fragments such as Fab, Fab', F(ab')2, Fv, scFv, dsFv, Diabody, and sc(Fv)2. Furthermore, a multimer of these functional fragments (e.g. dimer, trimer, tetramer, polymer) is also included in the antibody of the present invention.

Production of the antibody of the present invention may be carried out in accordance with a method known in the art. For example, a rabbit, etc. is immunized with the whole or part of a polypeptide represented by SEQ ID No: 1 or 2 as an immunogen, and purification of the serum thereof is carried out, thus enabling an antibody to be obtained.

The antibody of the present invention is an antibody that can specifically bind to BORIS belonging to isoform A or C or subfamily 5 or 6, and can detect a cell expressing BORIS belonging to isoform A or C or subfamily 5 or 6 or detect BORIS belonging to isoform A or C or subfamily 5 or 6 itself. Therefore, in one embodiment of the present invention, a kit for the detection and/or kit for the purification of a BORIS protein containing the antibody of the present invention is provided.

The kit of the present invention is not particularly limited as long as it contains the antibody of the present invention, and includes any kit known in the art; examples thereof include, but are not limited to, a kit used in an ELISA method, western blot method, chromatography method, immunostaining, etc.

The kit of the present invention may further contain, in addition to the antibody of the present invention, one or more of any component that is suitable for the application of the kit, and examples of such a component include, but are not limited to, a secondary antibody that may be labeled or may not be labeled, a chromogenic reagent, a solvent, a buffer, a positive control, a negative control, a reaction vessel, a pretreatment reagent, a blocking reagent, a slide glass, a cover glass, and an instruction manual for each application.

(10) Others

The present invention is based on the finding that a BORIS protein, in particular BORIS sf5 and/or sf6a, is highly expressed in cells having sternness properties in cervical cancer or ovarian cancer. Therefore, various techniques based on such a finding are included in the present invention.

In one embodiment, the present invention relates to an antibody that specifically recognizes BORIS sf5 or sf6. Such an antibody may be prepared using a method known in the art so that it recognizes a polypeptide having an amino acid sequence described in SEQ ID No: 1 or 2 or a part thereof as an epitope. Due to the use of such an antibody, it is possible to detect for example the amount of expression of BORIS sf5 and/or sf6 in a specific tissue and/or cell, and it is thereby possible to determine the presence or absence of a cancer stem cell or a tumor in a tissue or a subject. Furthermore, by suppressing the function of BORIS sf5 and/or sf6 that affects the sternness of cancer stem cells by the use of such an antibody, it is possible to treat cancer stem cells and carry out the prevention and/or treatment of a cancer.

Furthermore, another embodiment of the present invention relates to a polynucleotide having a sequence that is complementary to that of the BORIS gene. As described above, the BORIS gene, in particular a specific subfamily thereof, is particularly strongly expressed in cancer stem cells and is thought to affect the sternness. Therefore, it is thought that by inhibiting the expression of the BORIS gene, the sternness in cancer stem cells can be suppressed. Therefore, in a preferred embodiment, the polynucleotide of the present invention may be used as an inhibitory nucleic acid, in particular an siRNA. Moreover, the polynucleotide of the present invention may be used as a primer or a probe for detecting DNA or mRNA of BORIS sf5 and/or sf6 in a sample.

Yet another embodiment of the present invention relates a method for detecting cancer stem cells, the method including detecting the level of BORIS sf5 and/or sf6 mRNA and/or polypeptide in a sample obtained from a subject, and comparing the detected level with the level of BORIS sf5 and/or sf6 mRNA and/or polypeptide in normal tissue and/or cells as a reference value. As a method for detecting the mRNA and/or polypeptide level, a method known in the art may be used. Examples of the method for detecting the mRNA level include RT-PCR, DNA microarray, and northern blotting. In such a method for detecting the mRNA level, the primer and/or probe for BORIS sf5 and/or sf6 may be used. Examples of a method for detecting polypeptide level include immunohistochemical staining and western blotting. In such a method for detecting the polypeptide level, the antibody specific to BORIS sf5 and/or sf6 may be used.

In another embodiment, the present invention relates to a method for detecting a tumor in a subject, the method including detecting the level of BORIS sf5 and/or sf6 mRNA and/or polypeptide in a sample from a subject, and comparing the detected level with the level of BORIS sf5 and/or sf6 mRNA and/or polypeptide in normal tissue and/or cells as a reference value. As a method for detecting the level of mRNA and/or polypeptide, a method known in the art may be used. Examples of the method for detecting the mRNA level include RT-PCR, DNA microarray, and northern blotting. In such a method for detecting the mRNA level, the primer and/or probe for BORIS sf5 and/or sf6 may be used. Examples of the method for detecting the polypeptide level include immunohistochemical staining and western blotting. In such a method for detecting the polypeptide level, the antibody specific to BORIS sf5 and/or sf6 may be used. In the present invention, the method for detecting a tumor of the present embodiment may be carried out instead of the method of (8) above. Therefore, it may be used in the step of detecting a cancer in (9) above.

Yet another embodiment of the present invention relates to a pharmaceutical composition for treating a cancer associated with cancer stem cells, the cancer being of a female-specific organ, and the pharmaceutical composition containing a BORIS protein or a partial peptide of an isoform thereof. Whereas among cancer-testis antigens expression of BORIS is low, particularly in tissue other than the testis, the present inventors have found that it is strongly expressed in a cancer of a female-specific organ, such as cervical cancer, ovarian cancer, or uterine cancer, in particular a cancer containing cells having stemness. Therefore, it is expected to exhibit particularly excellent effects such as low side effects and high specificity in the treatment of a cancer in a female-specific organ.

EXAMPLES

The present invention is specifically explained below by reference to Examples, but the present invention should not be construed as being limited thereto. Unless otherwise specified, experimental methods employ methods usually used in the art such as methods described in for example 'Experimental Manual for Immunology' (Meneki Jikken Sosaho), Ed by: Shunsuke Uda, Susumu Konta, Tasuku Honjo, Toshiyuki Hamaoka.

Furthermore, the BORIS isoforms and subfamilies used in the Examples below are listed in the table below. Unless otherwise specified, when an isoform name is written it means a specific isoform, when a subfamily name is written it means any one of the isoforms belonging to the subfamily, and when simply 'BORIS' is written it means an expression product of the usual BORIS gene without specifying an isoform or a subfamily, or the BORIS B0 isoform. Furthermore, in the Examples below, 'peptide name-Tet' means an HLA tetramer binding to the peptide shown by the peptide name.

TABLE 1

Accession Number summary of BORIS isoforms

| Isoform number | Isoform | Subfamily | Transcript size (bp) | Accession number |
|---|---|---|---|---|
| 1 | BORIS B1 | 5 | 2506 | DQ778111 |
| 2 | BORIS C3 | 4 | 3393 | DQ778115 |
| 3 | BORIS B0 | 1 | 3500 | AF336042 |
| 4 | BORIS A1 | 1 | 3601 | DQ778108 |
| 5 | BORIS A2 | 1 | 3701 | DQ778109 |
| 6 | BORIS C1 | 1 | 4073 | DQ778110 |
| 7 | BORIS A5 | 3 | 2955 | DQ778122 |
| 8 | BORIS A3 | 1 | 3897 | DQ778112 |
| 9 | BORIS A6 | 3 | 3002 | DQ778123 |
| 10 | BORIS C6 | 3 | 2995 | DQ778121 |
| 11 | BORIS B3 | 4 | 2267 | DQ778125 |
| 12 | BORIS C8 | 4 | 4030 | DQ778118 |
| 13 | BORIS C4 | 4 | 2999 | DQ778116 |
| 14 | BORIS B4 | 3 | 2300 | DQ778126 |
| 15 | BORIS C7 | 6 | >2964 | DQ778119 |
| 16 | BORIS C9 | 6 | >2241 | DQ778120 |
| 17 | BORIS B2 | 4 | 2056 | DQ778124 |
| 18 | BORIS A4 | 2 | 1529 | DQ778113 |
| 19 | BORIS C2 | 2 | 2001 | DQ778114 |
| 20 | BORIS C5 | 4 | 2394 | DQ778117 |
| 21 | BORIS B5 | 3 | 2173 | DQ778127 |
| 22 | BORIS B6 | 6 | >1627 | DQ778128 |
| 23 | BORIS B7 | 6 | >902 | DQ778129 |

Example 1

Isolation/Identification of Cancer Stem Cells (1) Isolation of Spheroid-Forming Cells Sphere formation has been reported as being one of the indicators of cancer stem cell markers in cervical cancer. Therefore, a spheroid formation assay using a low adherent cell culture plate was carried out. Cervical cancer cell lines (CaSki, TCS, MS751, SKG-IIIb, ME-180, and SiHa) were cultured using a multi well plate having an ultra low adherent surface (Ultra Low Attachment 6-well plate, Corning). Adherent cultured cells were peeled off with a solution containing 0.25% trypsin in 2 mM EDTA, and were plated on each well at $10^3$ cells/well. As a medium, one prepared by adding to a serum-free DMEM/F-12 medium 20 ng/mL of h-EGF (acquired from R&D systems), 10 ng/mL of b-FGF (acquired from R&D systems), 1% penicillin/streptomycin (acquired from GIBCO), 4 μg/mL of heparin, and a final concentration of 1% of N2 supplement (acquired from WAKO) was used, culturing was carried out under normal culturing conditions for 7 days or 14 days, and formation of spheroids of 100 μm or greater was confirmed for all of the cell lines (FIG. 1). In the test below, a group of cells denoted by 'sphere' means a group of cells isolated from a spheroid formed by nonadherent culturing in the same manner as in this test. Furthermore, a group of cells denoted by 'bulk' means a group of cells obtained by normal adherent culturing.

(2) Properties of Spheroid-Forming Cells

In order to confirm that the spheroid-forming cells were cells exhibiting stem cell-like properties, a radiation tolerance test, an anticancer agent resistance test, and flow cytometry analysis were carried out, and it was confirmed that the sphere group was a group showing more stem cell-like properties compared with the bulk group.

(3) Analysis of Stemness Gene Expression

The expression level of each of SOX2, NANOG, and Oct3/4 used as stemness genes in the bulk group and the sphere group of the CaSki and TCS cell lines was analyzed by quantitative RT-PCR. As a PCR instrument a STEPONE real-time PCR system (Applied Biosystems) was used, gene expression was detected as a threshold cycle number (Ct), and the relative expression level was quantified when the stemness gene expression in the bulk group by the ΔΔCt method was defined as 1. As a primer/probe mix for SOX2, NANOG, and Oct3/4, TaqMan gene expression (Applied Biosystems) was used.

The results are shown in FIG. 2. It can be seen that in either of the cell lines there was high stemness gene expression in cells of the sphere group. This suggests that cancer cells showing stem cell-like properties were concentrated in the sphere group. The cDNA microarray analysis described below was carried out using the CaSki cell line, in which stemness gene expression was found to be particularly marked.

(4) cDNA Microarray

A cDNA microarray was carried out in order to analyze a gene that was highly expressed in the sphere group compared with the bulk group. First, total RNA was extracted from each cell using a commercial aminoallyl RNA amplification kit ver2 (high yield type) (Sigma Aldrich) in accordance with the instructions included with the kit. 3 μg of the total RNA thus obtained was reverse transcribed using commercial oligo(dT) T7 promoter primer and reverse transcription enzyme, thus synthesizing cDNA. Next, cRNA was synthesized using T7 RNA polymerase, and at the same time Cy3 or Cy5 labeled cytidine triphosphate was incorporated. By this process, a sample of the sphere group cells was labeled with Cy5. A sample of the bulk group cells was labeled with Cy3 as control cells. The quality of cRNA was reconfirmed using NanoDrop (Thermo Scientific). Subsequently, the Cy3-labeled cRNA and the Cy5-labeled cRNA were combined and fragmented in a hybridization cocktail (Sigma Aldrich). The labeled cRNA was hybridized with a 60mer probe oligonucleotide microarray (Panorama Human Micro Array, Sigma Aldrich) and incubated at 50° C. for 20 hours. The intensity of fluorescence was determined using a Genepix 4000B Microarray Scanner (Axon Instruments). An experiment was carried out again using the same method by labeling a sample of the sphere group cells with Cy3 and labeling a sample of the bulk group cells with Cy5 (Dye Swap method).

(5) Selection of Cancer Stem Cell-Specific Antigen Candidate Protein

In the results of the cDNA microarray above, expression in the sphere group was confirmed with a cancer-testis antigen (CT antigen) as a subject. The results are shown in the table below.

TABLE 2

Genes of cancer testis antigens that were highly expressed in spheroid cells

| Gene name | Accession number | Definition | Dye 1 | Dye 2 |
|---|---|---|---|---|
| SPANXB2 | NM_145664 | ref\|Homo sapiens SPANX Family, member B2 (SPANXB2), mRNA | 2.08 | 1.04 |

TABLE 2-continued

Genes of cancer testis antigens that were highly expressed in spheroid cells

| Gene name | Accession number | Definition | Dye 1 | Dye 2 |
|---|---|---|---|---|
| SPANXA1 | NM_013453 | ref\|Homo sapiens sperm protein associated with the nucleus, X-linked, family member A1 (SPANXAiV mRNA | 1.14 | 3.62 |
| IL13RA2 | NM_000640 | ref\|Homo sapiens Interleukin 13 receptor, alpha 2 (IL13RA2), mRNA | 9.53 | 220.22 |
| CSAG2 | NM_004909 | ref\|Homo sapiens CSAG family, member 2 (CSAG2) transcript variant 2, mRNA | 1.80 | 4.17 |
| CSAG1 | NM_153478 | ref\|Homo sapiens chondrosarcoma associated gene1 (CSAG1), transcript variant a, mRNA | 1.72 | 3.79 |
| PLU-1 | NM_006618 | ref\|Homo sapiens lysine (K)-specific demethylase 5B (KDM5B), mRNA | 8.6 | 1.68 |
| BORIS | NM_080618 | ref\|Homo sapiens CCCTC- binding factor (zinc finger protein) like (CTCFL), mRNA | 9.02 | 1.04 |
| LY6K | NM_017527 | ref\|Homo sapiens lymphocyte antigen 6 complex, locus K (LY6K), transcript variant 1, mRNA | 1.86 | 2.84 |
| ROPN1 | NM_017578 | ref\|Homo sapiens ropporin, rhophilin associated protein 1 (ROPN1), mRNA | 1.91 | 2.74 |
| CT62 | NM_001102658 | ref\|Homo sapiens cancer/testis antigen 62 (CT62), mRNA | 3.33 | 8.93 |
| LEMD1 | NM_001001552 | ref\|Homo sapiens LEM domain containing 1 (LEMD1), transcript variant 3, mRNA | 8.76 | 20.44 |

BORIS was identified as a CT antigen specifically expressed in the sphere group. It is therefore suggested that BORIS can be an effective treatment target for cancer stem cells.

Example 2

Evaluation of BORIS as Treatment Target for Cancer Stem Cells (1) Analysis of Expression of BORIS in Normal Tissue Human Multiple Tissue cDNA Panels I and II (Clontech) were used as a cDNA library for normal tissue. With regard to PCR, a cDNA mixture containing 0.1 to 0.5 µL of cDNA, 0.1 µL of Taq DNA polymerase (Qiagen), and 12 pmol of primer was first heated at 94° C. for 2 minutes, subsequently dissociated at 94° C. for 15 seconds, annealed at 60° C. for 30 seconds, and elongated at 68° C. for 30 seconds, this cycle being carried out for 30 to 40 cycles. The primers used were SEQ ID Nos: 35 and 36.

The results are shown in FIG. 3. It can be seen that BORIS is hardly expressed in normal tissue other than the testis.

(2) Analysis of Expression of BORIS in Cervical Cancer Cell Line cDNA was harvested from the bulk group and the sphere group of each of MS751, TCS, CaSki, SKG-IIIb, ME-180, and SiHa cell lines as cervical cancer cell lines using the same method as in Example 1 (4), and the amount of BORIS expressed in each cell line was quantified by the same method as in Example 1 (3) as a relative expression level when the expression in the bulk group of the TCS cell line was defined as 1. TaqMan gene expression (Applied Biosystems) was used as a BORIS primer/probe mix.

The results are shown in FIG. 4. Compared with the bulk group the amount of BORIS expressed increased greatly in the sphere group for more than half the cell lines.

(3) Analysis of Expression of BORIS in Other Cancer Cell Lines

The amount of BORIS expressed in bulk group cells of RL95-2 and HEC-1-A as endometrial cancer cell lines and TOV-21G, ES-2, MCAS, Ovcar-3, SMOV-2, and SKOV-3 as ovarian cancer cell lines was quantified in the same way as for (2) as a relative expression level when the expression in the TCS bulk group was defined as 1.

The results are shown in FIG. 5. BORIS showed a high expression level not only in cervical cancer but also in endometrial cancer and ovarian cancer.

(4) Analysis of Expression of BORIS Subfamily Isoforms in Cervical Cancer Cell Line The amount of BORIS subfamily isoform expressed in cervical cancer cell lines was analyzed by RT-PCR in the same way as for (1). The primers in the table below were used as primers specific to each subfamily.

TABLE 3

Table 3: Base sequence of primers used

| | Forward primer (fw) | Reverse primer (rv) |
|---|---|---|
| BORIS (sf1) | CTGCGAAGGGATGGAAGGAA (SEQ ID No: 17) | GAACACGCAACCCGAATCC (SEQ ID No: 18) |
| BORIS (sf5) | GGATAATTCCGCAGGCTGTA (SEQ ID No: 19) | TGGTCGTTCAGAGGAGTGTG (SEQ ID No: 20) |
| BORIS (sf2) | TAACACCCACACAGGAACCA (SEQ ID No: 21) | GCCTCTACTAAGATGCCATGAA (SEQ ID No: 22) |
| BORIS (sf3a) | CTTTTCCCGCTGGATTCTCT (SEQ ID No: 23) | GTCAGGAGGACACTCAAGCA (SEQ ID No: 24) |
| BORIS (sf3b) | CCATTCACCTGCCTTTCTTG (SEQ ID No: 25) | GGTTTTAAGCCACTCCATTTTG (SEQ ID No: 26) |
| BORIS (sf4a) | CCACAAAGGGTCAGAAGGAA (SEQ ID No: 27) | GGTCAGGAGTGAGAGACATGG (SEQ ID No: 28) |
| BORIS (sf4b) | TGTGATGTCTGCATGTTCACC (SEQ ID No: 29) | GCAGATCACTTGAGGTCAGGA (SEQ ID No: 30) |
| BORIS (sf4c) | TGCACAGACATTCGGAGAAG (SEQ ID No: 31) | AGATCACACCGTCTCCGTTC (SEQ ID No: 32) |
| BORIS (sf6) | CTCAGGTAAGGGCTCTGGTG (SEQ ID No: 33) | TACTCCACACAGTGGGGTTG (SEQ ID No: 34) |
| BORIS | GATGCTGAAAAGGCCAAATC (SEQ ID No: 35) | ACTTGTAGGGCCTGGTTCCT (SEQ ID No: 36) |

The results are shown in FIG. 6. In the bulk group cells of the CaSki cell line, marked expression was observed for subfamilies (sf) 1 to 4, but in the sphere group cells sf6, for which expression was hardly observed in the bulk group cells, was strongly expressed. Furthermore, in the MS751 cell line also, expression of sf1 and sf6 was observed in the sphere group cells but not for the bulk group cells.

(5) Analysis of Expression of BORIS Subfamily Variants in Ovarian Cancer Cell Lines The same experiment as in (4) above was carried out using ovarian cancer cell lines TOV21G and SMOV-2 instead of cervical cancer cell lines CaSki and MS751. The results are shown in FIG. 7.

As in the results for the cervical cancer cell lines above, in the ovarian cancer cell lines also, expression specific to BORIS sf6 was observed in the sphere group cells. Furthermore, in the ovarian cancer cell line, in both of the cell lines expression of not only sf6 but also sf5 was markedly increased compared with the bulk group cells.

(6) Analysis of Expression of BORIS Subfamily Variants in Lung Cancer Cell Lines and Primary Cultured Cells Established from Surgically Resected Piece from Lung Cancer Patient The same experiment as in (5) above was carried out using primary cultured cells established from small cell lung cancer-, non-small cell lung cancer-, lung squamous cancer-, and lung adenocancer-derived cell lines, and a surgical resection piece from a lung cancer patient. Spheroid-forming cells were prepared using the same procedure as in Example 1 (1) except that the medium used did not have N2 supplement and heparin added. The results are shown in FIG. 19-1, FIG. 19-2, FIG. 19-3, FIG. 19-4, and FIG. 19-5.

In the lung cancer-derived cell lines also expression of BORIS gene was observed. Specifically, in the small cell lung cancer lines of FIG. 19-1, expression of BORIS sf5 was enhanced in the sphere groups for SBC1 and SBC5, and expression of sf6 was enhanced for Lc817. In FIG. 19-2 expression of BORIS sf5 and sf4a was confirmed, and similarly expression of BORIS in lung squamous cancer and lung adenocarcinoma and enhancement of expression in the sphere group were observed. Furthermore, as shown in FIG. 19-5, in primary cultured cells established from a surgical resection piece from a lung cancer patient expression of BORIS was also confirmed and, in particular, since in the Primary7 cells enhancement of expression of several sf6 were confirmed in the sphere group, it shows that BORIS can be a very promising antigen for cancer immunotherapy in lung cancer.

Example 3

Investigation into BORIS sf6

(1) Preparation of BORIS Isoform Overexpression Line

Retrovirus vectors encoding B0 isoform, which is a BORIS sf1 isoform, B3 isoform, which is an sf4 isoform, and B6 isoform and C7 isoform, which are sf6 isoforms, were prepared using a Platinum retrovirus expression system containing a pMXpuro vector and Plat-A cells, and introduced into a TCS cell line, thus preparing the respective BORIS isoform overexpression lines. When the amount of BORIS isoform expressed was ascertained by quantitative PCR, it was confirmed that compared with one into which a mock vector was introduced, expression was about 10,000 times. An overexpression line by introduction into the SKG-IIIb cell line was also prepared by the same method.

(2) Sphere Formation Assay

A sphere formation assay was carried out by the same method as in Example 1 (1) above by plating 1000 cells/well of the overexpressing TCS cell line and the overexpressing SKG-IIIb cell line and culturing for 2 weeks.

The results are shown in FIG. 8 and FIG. 9. In both of the cell lines, significant sphere formation was confirmed in lines in which there was overexpression of BORIS sf6, and in particular BORIS B6 isoform.

(3) Abstraction of BORIS sf6-Specific HLA-Binding Epitope Candidates

An epitope peptide that binds to an HLA class I molecule and is subjected to antigen presentation is formed from 8 to 10 amino acids; the $2^{nd}$ and $9^{th}$ or $10^{th}$ amino acids from the N terminal are the most important amino acids for binding to an HLA class I molecule, and are called an anchor motif. It has been reported that this anchor motif varies according to the type of HLA class I molecule. For example, as an epitope peptide that binds to an HLA-A2 molecule, which has been subject to the most research worldwide, a peptide formed from 9 to 10 amino acids having leucine at the $2^{nd}$ position from the N terminal and leucine or valine at the $9^{th}$ or $10^{th}$ position is the most well known. Furthermore, as a peptide binding to an HLA-A24 molecule, a peptide formed from 9 to 10 amino acids having any one of tyrosine, phenylalanine, methionine, or tryptophan at the $2^{nd}$ position from the N terminal and any one of leucine, isoleucine, tryptophan, or phenylalanine at the $9^{th}$ or $10^{th}$ position is the most well known.

Peptides having the above HLA-binding anchor motif structures were abstracted from the BORIS sf6-specific C terminal sequence (SEQ ID No: 1). As HLA-A2-binding peptide candidates, KLLFIGTIKV (KLL peptide: SEQ ID No: 4) and LLFIGTIKV (LLF peptide: SEQ ID No: 5), and as an HLA-A24-binding peptide candidate, SFKKLLFIGTI (SEQ ID No: 3) were abstracted and synthesized by standard methods.

(4) HLA-A2-Binding Assay

T2 cells were cultured at 26° C. overnight. Subsequently, the cells were washed with PBS, KLL peptide and LLF peptide synthesized in (3) as HLA-A2-binding peptide candidates, as positive controls CMV peptide (SEQ ID No: 37), which is a cytomegalovirus-derived peptide, and Influenza (SEQ ID No: 38), which is an influenza virus-derived peptide, and as a negative control GK-12 peptide (SEQ ID No: 39), which is an HLA-A24-binding peptide, were added, and coculturing was carried out at 26° C. for 3 hours. The temperature was set at 37° C., coculturing was carried out for a further 3 hours, and the supernatant was then removed by centrifuging, thus isolating the cells. An HLA-A2 antibody was added to the isolated cells, the mixture was allowed to stand at 4° C. for 1 hour, and then washed with PBS. A fluorescently-labeled anti-mouse IgG+IgM antibody was added thereto as a secondary antibody, the mixture was allowed to stand at 4° C. for 30 minutes, and 1% formalin was then added thereto, thus immobilizing the cells. The immobilized cells were subjected to measurement of FITC fluorescence intensity using a flow cytometer (BECTON DIKINSON or Beckman Coulter).

The results are shown in FIG. 10. It can be seen that T2 cells that had been incubated with the KLL peptide and the LLF peptide both exhibited comparable fluorescence intensity to that of the CMV peptide and the Influenza peptide, and the HLA-A2 molecule was localized on the cell surface to the same degree. This suggests that both of the peptides bind to HLA-A2 and were subjected to antigen presentation on the cell surface.

(5) Induction of BORIS sf6-Specific CTLs by Polypeptide Stimulation

Peripheral blood was harvested from two healthy adults who were known to possess HLA-A*02:01 and subjected to centrifugation at 3,000 rpm for 5 to 10 minutes, and a plasma portion in the supernatant was collected. PBMCs were separated from portions other than the plasma portion by density gradient centrifugation. 10 mL of a medium containing 2-mercaptoethanol (final concentration 55 µM), L-glutamine (final concentration 2 mM), as antibiotics streptomycin (final concentration 100 µg/mL) and penicillin G (final concentration 100 U/mL), and 5% plasma component in a Hepes modified RPMI1640 medium (Sigma) and about $3\times10^7$ cells/plate of the PBMCs separated above were placed in each well of a 96 well round-bottom cell culture micro test plate (BECTON DIKINSON), suspended, and cultured. The BORIS sf6-specific CTL epitope candidate peptide SEQ ID No: 4 or SEQ ID No: 5 was added thereto at a concentration of 10 µg/mL. After culturing for 2 days, IL-2 was added at a final concentration of 50 U/mL, and culturing was carried out for a further 2 weeks.

10 µL of PE-labeled HLA-tetramer reagent and 20 µL of CD8-FITC antibody were added to an appropriate amount of the cultured cells, gently mixed, and allowed to stand at 4° C. for 30 minutes. 1.5 mL of PBS was added thereto and mixed, the mixture was then centrifuged at 3,000 rpm for 5 minutes, the supernatant was aspirated and discarded, and the cells were suspended in 400 µL of PBS and analyzed using a flow cytometer within 24 hours.

Analysis was carried out in two stages. In the first stage, cells in 8 wells in one column of the 96 well round-bottom cell culture micro test plate were collected as one sample, and the presence or absence of induction of BORIS-specific CTLs in the sample was ascertained. A sample for which CTL induction was confirmed in this stage was subjected to second stage analysis. In the second stage, cells were collected individually from the 8 wells as single samples, and the presence or absence of induction of BORIS-specific CTLs in the sample was ascertained.

Diagrams of the results of analysis by flow cytometer are expressed as dot plot development diagrams in which the X axis is CD8 and the Y axis is fluorescence intensity with the HLA-tetramer reagent shown on a log scale. Numerals in the dot plot development diagram show the percentage of UR in (UR+LR) where divisions into four regions are expressed as UL (upper left), UR (upper right), LL (lower left), and LR (lower right), that is, the proportion of HLA-tetramer reagent-positive cells among CD8-positive cells.

FIG. 20 shows the first stage analysis result of a sample harvested after culturing PBMCs of sample number A2-34 with BORIS sf6-specific CTL epitope candidate peptide SEQ ID No: 4 for 13 days. When induction of SEQ ID No: 4-specific CTLs was ascertained using KLL-Tet, CD8-positive KLL-Tet-positive cell populations were clearly detected in the UR of lane 5 and lane for sample number A2-34. This shows that the peptide of SEQ ID No: 4 is a BORIS sf6-specific CTL epitope peptide, and BORIS-specific CTLs were present in the living body of sample number A2-34.

FIG. 21 shows the second stage results of lane 5 and lane for which CTL induction was confirmed by the first stage analysis. KLL peptide (SEQ ID No: 4)-specific CTLs were detected in well C of lane 5 and well F of lane 11. This proves that the KLL peptide is an HLA-A*02:01-restricted BORIS sf6-specific CTL epitope peptide. Since KLL peptide-specific CTLs were detected in two wells among the 96 wells, the proportion of KLL peptide-specific CTLs present in the peripheral blood PBMCs can be calculated by the equation below.

Frequency of KLL peptide-specific CTLs=(Number of HLA-tetramer reagent positive wells)/(Number of PBMCs used in experiment×CD8-positive rate prior to induction)= $2/(3\times10^7\times0.16)=4.17\times10^{-7}$ FIG. 22 shows the first stage analysis result of a sample harvested after culturing PBMCs of sample number A2-29 with BORIS sf6-specific CTL epitope candidate peptide SEQ ID No: 5 for 13 days. When induction of SEQ ID No: 5-specific CTLs was ascertained with LLF-Tet, a CD8-positive LLF-Tet-positive cell population was clearly detected in the UR of lane 1, lane 2, lane 4, lane 5, lane 6, lane 7, lane 8, lane 9, lane 10, and lane 11 for sample number A2-29. This shows that the peptide of SEQ ID No: 5 is a BORIS sf6-specific CTL epitope peptide, and BORIS sf6-specific CTLs were present within the living body of sample number A2-29.

FIGS. 23-1 and 2 show the second stage results of lane 1, lane 2, lane 4, lane 5, lane 6, lane 7, lane 8, lane 9, lane 10, and lane 11 for which CTL induction was confirmed in the first stage. LLF peptide (SEQ ID No: 5)-specific CTLs were detected in well B of lane 1, wells B, D, G, and H of lane 2, wells C, F, and G of lane 4, wells B, F, and G of lane 5, wells E and F of lane 6, well F of lane 7, wells C and G of lane 8, well C of lane 9, well A of lane 10, and well E of lane 11. This proves that the LLF peptide is an HLA-A*02:01-restricted BORIS sf6-specific CTL epitope peptide. Since LLF peptide-specific CTLs were detected in 19 wells among the 96 wells, the proportion of LLF peptide-specific CTLs present in the peripheral blood PBMCs can be calculated by the equation below.

Frequency of LLF peptide-specific CTLs=(Number of HLA-tetramer reagent positive wells)/(Number of PBMCs used in experiment×CD8-positive rate prior to induction)= $19/(3\times10^7\times0.17)=3.73\times10^{-6}$ (6) Induction of BORIS sf6-Specific CTLs by PHA-Blast Stimulation 50 mL of peripheral blood was harvested from three healthy adults who were known to possess HLA-A*02:01 and subjected to centrifugation, and a plasma portion of the supernatant was collected. PBMCs were separated from a blood cell portion after removing the plasma using Lymphoprep (Axis-Shield Pros As). The PBMCs thus separated were suspended in 10 mL of an AIM-V culture medium, plated on a cell culture dish, and cultured for 4 hours in a $CO_2$ incubator at 37° C. The AIM-V culture medium means a medium in which a final concentration of 10 mM of HEPES (Life Technologies Corporation) and a final concentration of 50 µM of 2-mercaptoethanol (Life Technologies Corporation) were added to Life Technologies Corporation AIM-V. Subsequently, only the suspended cells were collected, and CD8-positive cells and CD8-negative cells were separated by a magnetic cell sorting method using MACS beads (Miltenyi Biotec).

CD8 negative cells were suspended in the AIM-V culture medium, then poured into a 48 well plate (Corning) at about $4\times10^5$ cells/well, and cultured.

On the same day as the day when the above culturing started, a final concentration of 1 µg/mL of PHA (phytohemagglutinin, Wako) and a final concentration of 100 U/mL of IL-2 (Life Technologies Corporation) were added to some of the wells with CD8 negative cells. On the 4th day after starting culturing, the cells were collected in a culture tube (BD), suspended in 10 mL of the AIM-V culture medium, and placed in a 75 cm² culture flask (Nunc). A final concentration of 100 U/mL of IL-2 (Shionogi & Co., Ltd.,) was further added. On the 8$^{th}$ day after starting culturing, the cells were collected in a culture tube (BD) and suspended in 1 mL of AIM-V (Life Technologies Corporation), and SEQ ID No: 5 peptide (final concentration 20 μg/mL) was added. Subsequently, the mixture was allowed to stand at room temperature for 1 hour and subjected to irradiation with 100 Gy radiation, thus preparing PHA-blast cells.

Culturing of CD8-positive cells was carried out by suspending them in a medium in which a final concentration of 10% of human AB serum (Lonza Japan) was added to the AIM-V culture medium, and pouring about 2×10⁶ cells/well into a 48 well plate (Corning).

On the 8$^{th}$ day from starting culturing, 10 ng of IL-7 (R&D Systems) was added to each well. Furthermore, CD8-positive cells and PHA-blast cells were mixed at 5:1, and coculturing was started. On the 9$^{th}$ day and 16$^{th}$ day after starting culturing, preparation of PHA-blast cells was started again, on the 16$^{th}$ day and 23$^{rd}$ day, when preparation of PHA-blast cells was complete, CD8-positive cells and PHA-blast cells were mixed again at 5:1, and stimulation with PHA-blast cells was carried out a total of three times. On the 16$^{th}$ day after starting culturing 10 U/mL of IL-2 (Shionogi & Co., Ltd.) was added, the concentration was increased stepwise up to a final concentration of 50 U/mL, and culturing was continued until the 28$^{th}$ day.

A cell population that had been cultured for 28 days was stained with a PE-labeled HLA-tetramer reagent and a CD8-FITC antibody by the same method as in (5) above, and the presence or absence of induction of BORIS sf6-specific CTLs in the sample was thus ascertained.

FIG. 24 shows the analysis results of a sample fractioned from a cell population that was obtained by culturing PBMCs of sample number A2-S1 with BORIS sf6-specific CTL epitope candidate peptide SEQ ID No: 5 for 28 days. When the induction of SEQ ID No: 5-specific CTLs was ascertained with LLF-Tet, a CD8-positive LLF-Tet-positive cell population was clearly detected for sample number A2-S1. This shows that the peptide of LLF peptide (SEQ ID No: 5) is an HLA-A*02:01-restricted BORIS sf6-specific CTL epitope peptide, and BORIS-specific CTLs were present within the living body of sample number A2-S1.

(7) Functional Analysis of LLF Peptide-Specific CTLs

A functional analysis of BORIS-specific CTLs was carried out using an ELISPOT Set (BD) kit. First, part of the cell population for which BORIS sf6-specific CTLs had been induced was harvested and prepared at 5×10⁵ cells/mL. This sample was plated at 100 μL/well on an ELISPOST assay plate having an anti-IFNγ antibody made into a solid phase thereon, and was allowed to stand in a CO₂ incubator at 37° C. for 30 minutes. Cells obtained by pulsing T2 cells with the peptide of SEQ ID No: 5 were added to the plate at 5×10⁴ cells/well, and allowed to stand in a CO₂ incubator at 37° C. overnight. After washing, a biotin-labeled anti-IFNγ antibody was added thereto, and a reaction was carried out at room temperature for 2 hours. The reaction solution was washed, and HRP-labeled streptavidin was added. After washing, a coloration agent was added at 100 μL/well, a reaction was carried out for 15 to 30 minutes, and IFNγ-secreting CTLs were made into spots and measured.

The results are shown in FIG. 25. Compared with a case in which an HIV-derived peptide (SLY peptide) as a negative control was added or a case in which no peptide was added (PBS), when stimulation was carried out with the LLF peptide (SEQ ID No: 5), many IFNγ spots were clearly detected. It was therefore confirmed that in the PBMCs cultured with added LLF peptide, LLF peptide (SEQ ID No: 5)-specific CTLs that produced IFNγ by restimulation were induced.

(8) Sorting and Culturing of CTL Clone

The BORIS sf6-specific CTLs for which IFNγ production capability had been confirmed in (7) above were double stained with an HLA-tetramer reagent and an anti-CD8-FITC (MBL) antibody, and one cell each of the cells that had reacted with the HLA-tetramer reagent and the anti-CD8-FITC antibody was plated on a 96 well plate (Corning) using a flow cytometer. The medium used for culturing this cell was one formed by adding a final concentration of 10% of human AB serum (Lonza Japan), a final concentration of 1% of penicillin/streptomycin (Life Technologies Corporation), a final concentration of 1% of GlutaMAX (Life Technologies Corporation), a final concentration of 100 U/mL of IL-2 (Shionogi & Co., Ltd.), and a final concentration of 5 μg/mL of PHA (Wako) to the AIM-V culture medium. Cells obtained by subjecting 50000 PBMCs collected and fractioned from three healthy donors to irradiation with 100 Gy radiation were added to each well.

Furthermore, with regard to a cell isolated by a flow cytometer, the color of the medium was examined, and half the amount of the medium was replaced as required. Moreover, at the stage the cells increased, they were transferred to a 48 well plate.

The results of staining the CTLs thus cultured with the LLF-Tet and CD8-FITC antibody using the same method as in (5) above to thus ascertain amplification of CTL are shown in FIG. 26. From the results, a CD8-positive LLF-Tet-positive cell population was clearly detected. This shows that monocloning and amplification of BORIS-derived LLF peptide-specific CTLs were successful.

The results of treating the CTLs thus cultured by the same procedure as in (7) above and carrying out a functional analysis of the CTLs are shown in FIG. 27. The results showed that compared with a case (−) in which no peptide was added, when stimulated with the LLF peptide, many IFNγ spots were detected. It was thereby confirmed that the cultured CTLs were LLF peptide (SEQ ID No: 5)-specific CTLs that produced IFNγ by restimulation with the LLF peptide.

(9) Functional Analysis of LLF Peptide-Specific CTLs

Analysis was carried out using an LDH killing assay (TaKaRa Bio) of whether the LLF peptide-specific CTLs whose culturing was complete in (8) attack cells presenting the LLF peptide. First, target cells (Target) that would be the subject of attack by the LLF peptide-specific CTLs were prepared. Three types of cells were prepared, that is, cells obtained by pulsing T2 cells with the LLF peptide of SEQ ID No: 5, and as negative controls T2 cells pulsed with the HIV-derived peptide (SLY peptide) and T2 cells as they were. The target cells were plated on a 96 well V-bottom plate (Corning) at 1×10⁴ cells/well. With regard to the LLF-specific CTLs (Effector), cell suspensions having a concentration of 9×10⁵ cells/mL, 3×10⁵ cells/mL, and 1×10⁵ cells/mL were prepared, and 100 μL thereof per well was plated and mixed with the target cells plated on the 96 well plate. Subsequently, the 96 well plate was subjected to centrifugation at 1800 rpm for 10 minutes and then allowed to stand in a CO₂ incubator at 37° C. for 4 hours to 12 hours. The 96 well plate was centrifuged, the cells were precipitated, and 100 μL of the supernatant was then transferred to a flat-bottom 96 well plate. 100 μL of a reaction solution containing diaphorase was added to each well and allowed to stand at room temperature for 30 minutes, and the absorbance at 490 nm was then measured. This procedure allowed LDH that is usually present within a cell membrane to be released outside the cell due to damage to the cell membrane when the cell is injured, and it is therefore possible by measuring the amount of LDH in the culture liquid to assess cytotoxicity. This method was used to examine whether LLF peptide-specific CTLs recognize and attack target cells presenting the LLF peptide.

The results thereof are shown in FIG. 28. The X axis shows the ratio of Effector and Target cells as an E/T ratio and the Y axis shows cytotoxicity (%). The cytotoxicity can be calculated in accordance with the equation below. It is given by [sample actual value (absorbance at 490 nm: A490)–low control (A490)]/[high control (A490)–low control (A490)]×100. The high control (A490) is the measurement value of one to which 2% Triton X-100 was added to the Target cell suspension and the low control (A490) is the measurement value of a suspension with Target cells alone. The cytotoxicity (%) is given as the average value of three samples.

The LLF peptide-specific CTLs showed cytotoxic activity at a high level when T2 cells pulsed with the LLF peptide were the target cells compared with the negative controls in which T2 cells pulsed with an HIV-derived peptide (SLY peptide) were the target cells or T2 cells to which no peptide was added were the target cells. That is, it is clear that cytotoxicity that specifically recognized cancer cells presenting the LLF peptide (SEQ ID No: 5) was exhibited.

Example 4

Examination of BORIS sf5

(1) Abstraction of BORIS-Specific HLA-Binding Epitope Candidate

BORIS-specific HLA-binding epitope candidates were abstracted in the same way as in Example 3 (3) above. With regard to BORIS as the subject of analysis, the BORIS candidate BORIS B1 isoform (subfamily 5), which has the longest amino acid sequence and is specifically expressed in cancer stem cells, was used, and epitope candidates having the property of binding to HLA-A*24:02, which about 60% of Japanese people possess, were abstracted and synthesized. The peptides that were synthesized are shown below.

TABLE 4

Table 4: HLA-A*24: 02-binding BORIS-specific CTL epitope candidate peptides synthesized

| SEQ ID No: | Sequence |
|---|---|
| 6 | Val Phe His Glu Arg Tyr Ala Leu Ile |
| 7 | Thr Phe His Cys Asp Val Cys Met Phe |
| 8 | His Phe Thr Ser Glu Ala Val Glu Leu |
| 9 | Lys Tyr Ile Leu Thr Leu Gln Thr Val |
| 10 | Arg Met Met Leu Val Ser Ala Trp Leu |
| 11 | Lys Tyr Gln Cys Pro His Cys Ala Thr |
| 12 | Lys Tyr Ala Ser Val Glu Ala Ser Lys Leu |
| 13 | Leu Tyr Ser Pro Gln Glu Met Glu Val Leu |
| 14 | Ser Tyr Ala Ser Arg Asp Thr Tyr Lys Leu |
| 15 | Lys Tyr Gln Cys Pro His Cys Ala Thr Ile |
| 16 | Arg Tyr Lys His Thr His Glu Lys Pro Phe |

Table 5 shows the properties of the BORIS HLA-A*24: 02-binding peptides that were synthesized. A sequence of three or four amino acids from the N terminal of the synthesized peptide is shown as an abbreviation for the peptide name. From the left, the peptide name, the amino acid sequence, the position in the BORIS isoform B1 amino acid sequence, the number of amino acids, and the score, calculated using BIMAS (BioInformatics & Molecular Analysis Section, http://thr.cit.nih.gov/index.shtml) HLA Peptide Binding Predictions (http://thr.cit.nih.gov/molbio/hla_bind/), used for analysis are shown. This score is a numerical value that is used for predicting the affinity between HLA-A*24:02 and a peptide, meaning the higher the score, the higher the possibility of HLA and the peptide forming a stable complex.

TABLE 5

Table 5: BORIS B1-derived HLA-A*24: 02-binding candidate synthetic peptides

| Peptide name | Amino acid sequence | Position | Number of amino acids | Score |
|---|---|---|---|---|
| KYA | KYASVEASKL (SEQ ID No: 12) | 348-357 | 10 | 440 |
| LYS | LYSPQEMEVL (SEQ ID No: 13) | 142-151 | 10 | 240 |
| SYA | SYASRDTYKL (SEQ ID No: 14) | 376-385 | 10 | 220 |
| RYK | RYKHTHEKPF (SEQ ID No: 16) | 333-342 | 10 | 200 |
| KYQC | KYQCPHCATI (SEQ ID No: 15) | 427-436 | 10 | 150 |
| HFT | HFTSEAVEL (SEQ ID No: 8) | 86-94 | 9 | 22 |
| KYI | KYILTLQTV (SEQ ID No: 9) | 77-85 | 9 | 18 |
| RMM | RMMLVSAWL (SEQ ID No: 10) | 670-678 | 9 | 17 |
| KYQ | KYQCPHCAT (SEQ ID No: 11) | 427-435 | 9 | 15 |
| TFH | TFHCDVCMF (SEQ ID No: 7) | 256-264 | 9 | 10 |
| VFH | VFHERYALI (SEQ ID No: 6) | 466-474 | 9 | 6 |

(2) Folding Test of BORIS-Specific CTL Epitope Candidate Peptides

The first step of HLA-tetramer reagent production starts with folding in which HLA, β2-microglobulin, and peptide, which are the starting materials, are mixed in an appropriate solution within a test tube. These three types of starting materials undergo an association reaction in the folding solution to thus form a three component complex (HLA-monomer). In this process, if the binding force between the HLA and the peptide is high, this association reaction progresses smoothly, and analysis with a gel filtration column enables the complex of the three starting materials (HLA-monomer) to be detected. On the other hand, when there is no binding force between HLA and the peptide, hardly any HLA-monomer is detected. Therefore, analyzing the folding solution over time or carrying out a thermal treatment, etc. enables the binding and stability of HLA and the peptide to be examined. In the present specification this test is called a 'folding test'.

The folding test was carried out using the 11 types of peptides that were synthesized. In brief, HLA-A*24:02 (60 mg/L) and β2-microglobulin (20 mg/L) expressed and purified using an *Escherichia coli* expression system and the BORIS-specific CTL epitope candidate peptide (30 μM) were added to a folding solution (1 M Tris-HCl, 0.5 M EDTA, 2 M arginine, 5 mM GSH, 0.5 mM GSSG, and protease inhibitor) (all of the concentrations within the parentheses are final concentrations) and mixed, the folding solution was then sampled over time, and analysis was carried out using a gel filtration column. A positive control peptide formed from 9 amino acids (SEQ ID No: 40), a positive control peptide formed from 10 amino acids (SEQ ID No: 41), and respective negative controls (SEQ ID Nos: 42 and 43) were used as comparative subjects.

The results are shown in FIG. 11. From the results of gel filtration column analysis, the HLA molecule and β2-microglobulin when expressed and purified using the *Escherichia coli* expression system were solubilized with 8 M urea, but insoluble HLA molecules that could not form the HLA-monomer were detected as an aggregate at 7 to 8 minutes, a peak attributable to the HLA-monomer was then detected at around 10 minutes, and the β2-microglobulin was detected at around 14 minutes. From 15 minutes onward, components of the folding solution and the peptide were detected. Therefore, the results are shown as a bar graph of values obtained by converting the peak area at around 10 minutes showing formation of the HLA-monomer into the estimated amount of HLA-monomer formed (mg).

(3) Production of BORIS-Specific HLA-Tetramer Reagent

Based on the results of the folding test in (2) above, a PE-labeled HLA-tetramer reagent was produced using HLA-A*24:02 and the 10 types of BORIS-specific CTL epitope candidate peptides other than SEQ ID No: 11. In the present specification, the HLA-tetramer reagent thus produced is denoted by an abbreviation such as for example KYA-Tet, and this shows that it was produced using a three component complex of HLA-A*24:02, KYA (KYAS-VEASKL) peptide, and β2-microglobulin. In brief, in the same way as in (2) above, HLA-A*24:02, β2-microglobulin, and the BORIS-specific CTL epitope candidate peptide were added to the folding solution and mixed, thus forming an HLA-monomer. Here, an expression protein was designed so that a biotin binding site would be added to the C terminal of a recombinant HLA-A*24:02 molecule, and after the HLA-monomer was formed, biotin was added to said site. Dye-labeled streptavidin and the biotinylated HLA-monomer were mixed at a molar ratio of 1:4, thus giving an HLA-tetramer reagent.

(4) Induction of BORIS-Specific CTLs

Peripheral blood was harvested from seven healthy adults who were known to possess HLA-A*24:02 and subjected to centrifugation at 3,000 rpm for 5 to 10 minutes, and a plasma portion in the supernatant was collected. PBMCs were separated from a portion other than the plasma portion by density gradient centrifugation. 10 mL of a medium containing 2-mercaptoethanol (final concentration 55 μM), L-glutamine (final concentration 2 mM), as antibiotics streptomycin (final concentration 100 μg/mL) and penicillin G (final concentration 100 U/mL), and 5% plasma component in a Hepes modified RPMI1640 medium (Sigma) and about $3 \times 10^3$ cells/well of the PBMCs separated above were placed in each well of a 96 well round-bottom cell culture micro test plate (BECTON DIKINSON), suspended, and cultured. The BORIS specific CTL epitope candidate peptide other than SEQ ID No: 11 was added thereto at a concentration of 10 μg/mL. After culturing for 2 days, IL-2 was added at a final concentration of 50 U/mL, and culturing was carried out for a further 2 weeks.

10 μL of PE-labeled HLA-tetramer reagent and 20 μL of CD8-FITC antibody were added to an appropriate amount of the cultured cells, gently mixed, and allowed to stand at 4° C. for 30 minutes. 1.5 mL of PBS was added thereto and mixed, the mixture was then centrifuged at 3,000 rpm for 5 minutes, the supernatant was aspirated and discarded, and the cells were suspended in 400 μL of PBS and analyzed using a flow cytometer within 24 hours.

Analysis was carried out in two stages. In the first stage, cells in 8 wells in one column of the 96 well round-bottom cell culture micro test plate were collected as one sample, and the presence or absence of induction of BORIS-specific CTLs in the sample was ascertained. A sample for which CTL induction was confirmed in this stage was subjected to second stage analysis. In the second stage, cells were collected individually from the 8 wells as single samples, and the presence or absence of induction of BORIS-specific CTLs was ascertained.

FIG. 12-1 shows the results of first stage analysis of a sample harvested from a culture obtained by culturing the PBMCs of sample number A24-38 with BORIS-specific CTL epitope candidate peptide SEQ ID No: 10 for 13 days. The diagrams are expressed as dot plot development diagrams in which the X axis is CD8 and the Y axis is fluorescence intensity with the HLA-tetramer reagent shown on a log scale, and numerals in the dot plot development diagram show the percentage of UR in (UR+LR) where divisions into four regions are expressed as UL (upper left), UR (upper right), LL (lower left), and LR (lower right), that is, the proportion of HLA-tetramer reagent-positive cells among CD8-positive cells. When induction of SEQ ID No: 10-specific CTLs was ascertained with RMM-Tet, CD8-positive RMM-Tet-positive cell populations were clearly detected in the UR of lane 2, lane 4, lane 8, and lane 9 for sample number A24-38. This shows that the peptide of SEQ ID No: 10 is a BORIS-specific CTL epitope peptide and BORIS-specific CTLs were present within the living body of sample number A24-38.

FIG. 12-2 shows the second stage results, which are the results of further analysis of lane 2, lane 4, lane 8, and lane 9, for which CTL induction was confirmed in the first stage. CTLs specific to the RMM peptide (SEQ ID No: 10) were detected in wells H of lane 2, G and H of lane 4, F of lane 8, and A of lane 9. This proves that the RMM peptide is an HLA-A*24:02-restricted BORIS-specific CTL epitope peptide. Since CTLs specific to the RMM peptide were detected in 5 wells among 96 wells, the proportion of RMM peptide-specific CTLs present in the peripheral blood PBMCs can be calculated by the equation below.

Frequency of RMM peptide-specific CTLs=(Number of HLA-tetramer reagent positive wells)/(Number of PBMCs used in experiment×CD8-positive rate prior to induction)= $5/(3 \times 10^7 \times 0.18) = 9.26 \times 10^{-7}$ (5) Preparation of Antigen-Presenting Cells In accordance with a method described in Kuzushima et al., Clin Exp Immunol. 1996; 103: 192-198, an EBV-infected B cell line (hereinafter, called an EBV infected LCL) was established. In brief, a culture supernatant (containing live EBV virus) of B95-8 cells (acquired from JCRB Cell Bank), which is an EBV-producing cell line, and PBMCs were mixed and cultured, thus giving an EBV-infected LCL.

(6) Functional Analysis of RMM Peptide-Specific CTL

Half of the amount of PBMCs induced in (4) was transferred to a 96 well round-bottom cell culture micro test plate, and the RMM peptide was added at a final concentration of 100 ng/mL. Furthermore, Brefeldin A (BFA) was added at a final concentration of 1 µg/mL, and culturing was carried out in a 5% $CO_2$ incubator at 37° C. for 5 to 16 hours. After culturing, the cells were washed, a PE (phycoerythrin)-labeled HLA-tetramer reagent and a PC5 (phycoerythrin-Cy5)-labeled CD8 antibody (Beckman Coulter) were added, and the mixture was allowed to stand at room temperature for 15 to 30 minutes. After washing, immobilization was carried out with 4% formaldehyde at 4° C. for 15 minutes, and washing with an excess amount of washing liquid was carried out. After carrying out a membrane permeation treatment with 0.1% saponin, an FITC-labeled anti-IFNγ antibody (MBL) was added, and a reaction was carried out at room temperature for 15 to 30 minutes. After washing, the IFNγ-positive cell rate among T cells or the IFNγ-positive cell rate among HLA-tetramer reagent-positive cells was quantified using a flow cytometer.

The results are shown in FIG. 13. IFNγ-positive HLA-tetramer reagent-positive cells appeared in the UR only when stimulated with the RMM peptide, and when no RMM peptide was added hardly any appearance was observed. It can be understood from this that when stimulated with the RMM peptide CTLs specifically reacting with RMM-Tet were induced. This result makes it clear that RMM peptide-specific CTLs having cytotoxicity and producing IFNγ upon restimulation were induced in PBMCs cultured with RMM peptide added, and these cells were CTLs specific to the RMM peptide (SEQ ID No: 10), which is an HLA-A*24:02-restricted BORIS-derived peptide, since it is stained with the HLA-tetramer reagent.

(7) Induction of BORIS sf5-Specific CTLs

Using the same procedure as in Example 3 (6) except that the peptide (RMM peptide) of SEQ ID No: 10 was used when preparing PHA-blast cells, BORIS sf5-specific CTLs were induced from a healthy adult who was known to possess HLA-A*24:02 or HLA-A*02:01.

The CTLs thus induced were stained by the same method as in Example 3 (5), and the presence or absence of BORIS sf5-specific CTLs in the sample was ascertained.

FIG. 29 shows the results of analysis of a cell population obtained by culturing PBMCs of sample number A24-S4, which possessed HLA-A*24:02, or sample number A2-S5, which possessed HLA-A*02:01, with RMM peptide (SEQ ID No: 10)-presenting cells for 28 days. Ascertaining the presence or absence of induction of RMM peptide-specific CTLs in sample numbers A24-S4 and A2-S5 was carried out by analysis using the RMM peptide and an HLA tetramer reagent that had been produced so as to correspond to the type of HLA possessed by the respective sample. From the results, a CD8-positive RMM-Tet-positive cell population was clearly detected for sample numbers A24-S4 and A2-S5. This shows that the peptide of SEQ ID No: 10 is a BORIS sf5-specific CTL epitope peptide, and BORIS-specific CTLs were present in the living body of sample numbers A24-S4 and A2-S5. Furthermore, it has been established that the peptide of SEQ ID No: 10 has the property of binding to both HLA-A*24:02 and HLA-A*02:01 HLA types.

Functional analysis of BORIS-specific CTLs was carried out by the same procedure as in Example 3 (7) using an ELISPOT Set (BD) kit, and IFNγ secreted by the RMM peptide-specific CTLs was made into spots and counted.

FIG. 30 shows the results, in which the numbers of spots are expressed as a bar graph. Compared with a case in which an HIV-derived peptide (RYL peptide for sample A24-S4 and SLY peptide for sample A2-S5), which was a negative control, was added or when no peptide was added (PBS), when stimulation with the RMM peptide was carried out, the number of spots detected was clearly large.

(8) Analysis of RMM Peptide

The RMM peptide has the $670^{th}$ to $678^{th}$ amino acids of the BORIS B1 isoform. Here, since BORIS B1 is an isoform formed from 700 amino acids belonging to BORIS subfamily 5, and BORIS sf5 is known to have a subfamily specific sequence in the 132 amino acids of the C terminal, in particular the 38 amino acids of the C terminal (SEQ ID No: 2), the RMM peptide is a sequence specific to BORIS sf5 and is an epitope peptide that can induce CTLs that can target ovarian cancer-derived cancer stem cells, which have been found by the present invention to specifically express BORIS sf5.

Example 5

Examination of BORIS C1 Isoform (1) Abstraction of BORIS-Specific HLA-Binding Epitope Candidates BORIS-specific HLA-binding epitope candidates were abstracted in the same way as in Example 3 (3) except that a BORIS C1 isoform (subfamily 1, SEQ ID No: 76) was used as the BORIS analysis subject and HLA-A*02:01 was used as the HLA type. The peptides synthesized are shown below.

TABLE 6

Table 6 HLA-A*02: 01-binding BORIS-specific CTL epitope candidate peptides synthesized

| SEQ ID No: | Sequence |
|---|---|
| 47 | Val Leu Glu Glu Glu Val Glu Leu Val |
| 48 | Lys Leu Ala Val Ser Leu Ala Glu Thr |
| 49 | Ser Val Leu Glu Glu Glu Val Glu Leu |
| 50 | Ser Leu Ala Glu Thr Ala Gly Leu Ile |
| 51 | Val Leu Ser Glu Gln Phe Thr Lys Ile |
| 52 | Ile Leu Gln Lys His Gly Glu Asn Val |
| 53 | Ala Leu Glu Glu Asn Val Met Val Ala |

TABLE 6-continued

Table 6 HLA-A*02: 01-binding BORIS-specific CTL epitope candidate peptides synthesized

| SEQ ID No: | Sequence |
|---|---|
| 54 | Tyr Ala Ser Arg Asp Thr Tyr Lys Leu |
| 55 | Met Ala Ala Thr Glu Ile Ser Val Leu |
| 56 | His Ala Leu Glu Glu Asn Val Met Val |
| 57 | Val Leu Thr Val Ser Asn Ser Asn Val |

Table 7 shows the properties of the HLA-A*02:01-binding BORIS peptides synthesized. A sequence of three or four amino acids from the N terminal of the synthesized peptide is shown as an abbreviation for the peptide name. From the left, the peptide name, the amino acid sequence, the position in the BORIS C1 isoform amino acid sequence, the number of amino acids, and the score, calculated using SYFPEITHI (http://www.syfpeithi.de/0-Home.htm) EPITOPE PREDICTION (http://www.syfpeithi.de/bin/MHCServer.dll/EpitopePrediction.htm), used for analysis are shown. This score is a numerical value that is used for predicting the affinity between HLA and peptide for the structural motif of the HLA-A*02:01 molecule and the peptide, meaning the higher the score, the higher the possibility of HLA and the peptide forming a stable complex.

TABLE 7

Table 7 BORIS-derived HLA-A*02: 01-binding candidate synthetic peptides

| Peptide name | Amino acid sequence | Position | Number of amino acids | Score |
|---|---|---|---|---|
| VLE | VLEEEVELV (SEQ ID No: 47) | 60-68 | 9 | 26 |
| KLA | KLAVSLAET (SEQ ID No: 48) | 168-176 | 9 | 25 |
| SVLE | SVLEEEVEL (SEQ ID No: 49) | 59-67 | 9 | 24 |
| SLAE | SLAETAGLI (SEQ ID No: 50) | 172-180 | 9 | 24 |
| VLS | VLSEQETKI (SEQ ID No: 51) | 8-16 | 9 | 23 |
| ILQ | ILQKHGENV (SEQ ID No: 52) | 417-425 | 9 | 22 |
| ALE | ALEENVMVA (SEQ ID No: 53) | 155-163 | 9 | 21 |
| YAS | YASRDTYKL (SEQ ID No: 54) | 377-385 | 9 | 21 |
| MAA | MAATEISVL (SEQ ID No: 55) | 1-9 | 9 | 20 |
| HAL | HALEENVMV (SEQ ID No: 56) | 154-162 | 9 | 20 |
| VLT | VLTVSNSNV (SEQ ID No: 57) | 216-224 | 9 | 20 |

(2) Folding Test of BORIS-Specific CTL Epitope Candidate Peptides

A folding test was carried out using the 11 types of synthesized peptides shown in Table 7. The folding test was carried out by the same method as in Example 4 (2) except that HLA-A*02:01 was used as the HLA, those peptides described in Table 7 were used as the epitope candidate peptides, and as comparative subjects the peptide of SEQ ID No: 58 was used as a positive control peptide and the peptide of SEQ ID No: 59 was used as a negative control.

The results are shown in FIG. 33. The results show numerical values based on the estimated amount of HLA-monomer formed (mg) in the same way as in Example 4 (2). From the results, in the 10 types of BORIS-specific CTL epitope candidate peptides from SEQ ID No: 47 to SEQ ID No: 57 apart from SEQ ID No: 55, sufficient formation of HLA-monomer was observed compared with the negative control. That is, it has been shown that the BORIS-specific CTL epitope candidate peptides described in Table 7 other than the MAA peptide bind to HLA-A*02:01.

(3) Production of BORIS-Specific HLA-Tetramer Reagent

Based on the results of the folding test in (2), a PE-labeled HLA-tetramer reagent was produced by the same procedure as in Example 4 (3) except that the 10 types of BORIS-specific CTL epitope candidate peptides from SEQ ID No: 47 to SEQ ID No: 57, apart from SEQ ID No: 55, and HLA-A*02:01 were used.

(4) Induction of BORIS-Specific CTLs

CTLs were induced by the same method as in Example 3 (5) except that four healthy adults who were known to possess HLA-A*02:01 were the subjects and the BORIS-specific CTL epitope candidate peptides from SEQ ID No: 47 to SEQ ID No: 57, apart from SEQ ID No: 55, were used.

The presence or absence of CTL induction was ascertained by the same method as in Example 3 (5) for a cell population for which CTLs had been induced. Staining of CTLs was carried out using an HLA-tetramer reagent that corresponded to the BORIS-specific CTL epitope candidate peptide used for induction. Representative results when CTL induction was confirmed are shown below.

FIG. 34 shows the results of first stage analysis of a sample harvested from a culture obtained by culturing PBMCs harvested from sample number A2-29 with the BORIS-specific CTL epitope candidate peptide SEQ ID No: 47 for 13 days, FIG. 36 shows sample number A2-27, and FIG. 38 shows sample number A2-34. When the SEQ ID No: 47-specific CTL induction was ascertained with VLE-Tet, a CD8-positive VLE-Tet-positive cell population was clearly detected in the UR of lane 10 for sample number A2-29, lane 3 for sample number A2-27, and lane 4 for sample number A2-34. This shows that the peptide of SEQ ID No: 47 is a BORIS-specific CTL epitope peptide, and BORIS-specific CTLs were present within the living body of sample number A2-29, sample number A2-27, and sample number A2-34.

FIG. 35, FIG. 37, and FIG. 39 show the second stage results of lanes for which CTL induction was confirmed in the first stage. VLE peptide (SEQ ID No: 47)-specific CTLs were detected in well H of lane 10 in FIG. 35, well E of lane 3 in FIG. 37, and well C of lane 4 in FIG. 39. This proves that the VLE peptide is an HLA-A*02:01-restricted BORIS-specific CTL epitope peptide. Since in all of the samples VLE peptide-specific CTLs were detected in one well among the 96 wells, the proportion of VLE peptide-specific CTLs present in the peripheral blood PBMCs can be calculated by the equation below.

Frequency of VLE peptide-specific CTLs=(Number of HLA-tetramer reagent positive wells)/(Number of PBMCs used in experiment×CD8-positive rate prior to induction)= $1/(3 \times 10^7 \times 0.18)=1.85 \times 10^{-7}$ FIG. 40 shows the results of first stage analysis of a sample harvested from a culture obtained by culturing PBMCs harvested from sample number A2-29 with the BORIS-specific CTL epitope candidate peptide SEQ ID No: 48 for 13 days. When the induction of CTLs specific to SEQ ID No: 48 was ascertained with KLA-Tet, a CD8-positive KLA-Tet-positive cell population was clearly detected in the UR of lane 2, lane 5, and lane 11 for sample number A2-29. This shows that the peptide of SEQ ID No: 48 is a BORIS-specific CTL epitope peptide, and BORIS-specific CTLs were present in the living body of sample number A2-29.

FIG. 41 shows the second stage result of lanes for which CTL induction was confirmed in the first stage. In FIG. 41, KLA peptide (SEQ ID No: 48)-specific CTLs were detected in well H of lane 2, well D of lane 5, and well F of lane 11. This proves that the KLA peptide is an HLA-A*02:01-restricted BORIS-specific CTL epitope peptide. Since CTLs specific to the KLA peptide were detected in 3 wells among 96 wells, the proportion of KLA peptide-specific CTLs present in the peripheral blood PBMCs can be calculated by the equation below.

Frequency of KLA peptide-specific CTLs=(Number of HLA-tetramer reagent positive wells)/(Number of PBMCs used in experiment×CD8-positive rate prior to induction)=$3/(3 \times 10^7 \times 0.19)$ $=5.26 \times 10^{-7}$ FIG. 42 shows the results of first stage analysis of a sample harvested from a culture obtained by culturing PBMCs harvested from sample number A2-29 with the BORIS-specific CTL epitope candidate peptide SEQ ID No: 57 for 13 days. When the induction of CTLs specific to SEQ ID No: 57 was ascertained with VLT-Tet, a CD8-positive VLT-Tet-positive cell population was clearly detected in the UR of lane 7 and lane 9 for sample number A2-29. This shows that the peptide of SEQ ID No: 57 is a BORIS-specific CTL epitope peptide, and BORIS-specific CTLs were present within the living body of sample number A2-29.

FIG. 43 shows the second stage result for lanes in which CTL induction was confirmed in the first stage. In FIG. 43, VLT peptide (SEQ ID No: 57)-specific CTLs were detected in well A of lane 7 and well G of lane 9. This proves that the VLT peptide is an HLA-A*02:01-restricted BORIS-specific CTL epitope peptide. Since CTLs specific to the VLT peptide were detected in 2 wells among 96 wells, the proportion of VLT peptide-specific CTLs present in the peripheral blood PBMCs can be calculated by the equation below.

Frequency of VLT peptide-specific CTLs=(Number of HLA-tetramer reagent positive wells)/(Number of PBMCs used in experiment×CD8-positive rate prior to induction)= $2/(3 \times 10^7 \times 0.19)=3.51 \times 10^{-7}$ (5) Functional Analysis of Peptide-Specific CTLs PBMCs containing KLA peptide-specific CTLs induced from sample A2-29 or PBMCs containing VLT peptide-specific CTLs induced from sample A2-29 were each transferred to 2 wells of a 96 well round-bottom cell culture micro test plate at about $3 \times 10^6$ cells. Among the 2 wells, the KLA peptide was added to one well of PBMCs containing KLA peptide-specific CTLs and the VLT peptide was added to one well of PBMCs containing VLT peptide-specific CTLs at a final concentration of 100 ng/mL, and the remaining 1 well was prepared as an untreated well. Furthermore, an anti-CD107a-FITC labeled antibody and monensin were added to both the well to which the peptide had been added and the untreated well, and culturing was carried out in a $CO_2$ incubator at 37° C. for 4 hours. After the culturing, the cells were washed, a PE-labeled HLA-tetramer reagent corresponding to each peptide and a PC5 (phycoerythrin-Cy5)-labeled anti-CD8 antibody (Beckman Coulter) were added, and the mixture was allowed to stand at room temperature for 15 to 30 minutes. The mixture was washed with an excess amount of washing liquid, CD107a, which is a CTL degranulation marker, was detected using a flow cytometer, and the positive cell rate was calculated. CTLs are known to express CD107a, which is present on the inner membrane of intracellular granules, on the cell membrane when releasing a cytotoxic factor such as perforin or granzyme, and detecting the CD107a molecule enables the release of a cytotoxic factor to be examined indirectly.

The results are shown in FIG. 44 and FIG. 45. In FIG. 44, CD107a positive HLA-tetramer reagent-positive cells appeared in the UR only when stimulated with KLA peptide, and when no KLA peptide was added hardly any appearance was observed. It can be understood from this that when stimulated with the KLA peptide, CTLs with which KLA-Tet specifically reacts are induced. Furthermore, in FIG. 45, CD107a-positive HLA-tetramer reagent-positive cells appeared in the UR only when stimulated with the VLT peptide, and when no VLT peptide was added hardly any appearance was observed. It can be understood from this that when stimulated with the VLT peptide, CTLs with which VLT-Tet specifically reacts are induced. It can be understood from this result that in PBMCs cultured by adding the KLA peptide or PBMCs cultured by adding the VLT peptide, CTLs having cytotoxicity that produces granzyme or perforin by restimulation are induced. Furthermore, it has been proved that since these CTLs are stained with an HLA-tetramer reagent, they are CTLs specific to the KLA peptide (SEQ ID No: 48) or the VLT peptide (SEQ ID No: 57), which are HLA-A*02:01-binding BORIS C1-derived peptides.

The results of examining the induction of HLA-A*02:01-restricted BORIS-specific CTLs are summarized in Table 8.

TABLE 8

Table 8 Results of induction of BORIS-specific CTLs

| Peptide sequence | Sample number | | | |
|---|---|---|---|---|
| | A2-29 | A2-34 | A2-27 | A2-25 |
| SEQ ID No: 47 VLEEEVELV | O | O | O | X |
| SEQ ID No: 48 KLAVSLAET | O | X | X | X |
| SEQ ID No: 49 SVLEEEVEL | X | X | X | X |
| SEQ ID No: 50 SLAETAGLI | X | X | X | X |
| SEQ ID No: 51 VLSEQFTKI | X | X | X | X |
| SEQ ID No: 52 ILQKHGENV | X | X | X | X |
| SEQ ID No: 53 ALEENVMVA | X | X | X | X |

TABLE 8-continued

Table 8 Results of induction of BORIS-specific CTLs

| | Peptide sequence | Sample number | | | |
|---|---|---|---|---|---|
| | | A2-29 | A2-34 | A2-27 | A2-25 |
| SEQ ID No: 54 | YASRDTYKL | X | X | X | X |
| SEQ ID No: 56 | HALEENVMV | X | X | X | X |
| SEQ ID No: 57 | VLTVSNSNV | O | X | X | X |

O: tetramer(+), CD8(+) cells induction confirmed
X: tetramer(+), CD8(+) cells not induced (6) Abstraction of BORIS-Specific HLA-A*11:01-Binding Epitope Candidates BORIS-specific HLA-binding epitope candidates were abstracted in the same way as in Example 3 (3) above. However, these were different in terms of abstraction of epitope candidates that had the property of binding to HLA-A*11:01, which is a third frequency in south east Asia, including Japanese people. The peptide sequences of the abstracted epitope candidates were synthesized; the sequences are shown in Table 9-1, and control peptides are shown in Table 9-2.

TABLE 9-1

Table 9-1 BORIS-specific peptides having possibility of binding to HLA-A*11:01

| Peptide name | Amino acid sequence | Position | Number of amino acids | Score |
|---|---|---|---|---|
| Conserved peptides in sf5 (BORIS B1) and sf6 (BORIS C7/C9) | | | | |
| SVL | SVLSEQFTK (SEQ ID No: 60) | 7-15 | 9 | 0.751 |
| SLA | SLAETTGLIK (SEQ ID No: 61) | 172-181 | 10 | 0.651 |
| RMS | RMSSFNRHMK (SEQ ID No: 62) | 268-277 | 10 | 0.697 |
| NTH | NTHTGTRPYK (SEQ ID No: 63) | 305-314 | 10 | 0.632 |
| CSY | CSYASRDTYK (SEQ ID No: 64) | 375-384 | 10 | 0.717 |
| Unique peptides of sf5 (BORIS B1) | | | | |
| GTM | GTMKIHILQK (SEQ ID No: 65) | 411-420 | 10 | 0.728 |
| KQL | KQLLNAHFRK (SEQ ID No: 66) | 526-535 | 10 | 0.643 |
| TVY | TVYKCSKCGK (SEQ ID No: 67) | 544-553 | 10 | 0.644 |
| ASG | ASGKGRRTRK (SEQ ID No: 68) | 577-586 | 10 | 0.453 |
| AAA | AAAEEASTTK (SEQ ID No: 69) | 615-624 | 10 | 0.539 |

TABLE 9-1-continued

Table 9-1 BORIS-specific peptides having possibility of binding to HLA-A*11:01

| Peptide name | Amino acid sequence | Position | Number of amino acids | Score |
|---|---|---|---|---|
| Unique peptides of sf6 (BORIS C7/C9) | | | | |
| GLI | GLIPTVLTLK (SEQ ID No: 70) | 401-410 | 10 | 0.685 |
| TVL | TVLTLKASFK (SEQ ID No: 71) | 405-414 | 10 | 0.717 |
| KLLF | KLLFIGTIK (SEQ ID No: 72) | 415-423 | 9 | 0.602 |

TABLE 9-2

Table 9-2 Control peptides

| Peptide name | Amino acid sequence | Position | Number of amino acids | Score |
|---|---|---|---|---|
| ATV | ATVQGQNLK (SEQ ID No: 73) | 501-509 | 9 | 0.643 |
| AYA | AYACNTSTL (SEQ ID No: 40) | 80-88 | 9 | 0.072 |

Table 9-1 shows the properties of the BORIS-specific HLA-A*11:01-binding epitope candidates synthesized. Peptides that bind to HLA-A11 are known to often have any one of Ile, Met, Ser, Thr, and Val at the $2^{nd}$ position from the N terminal and either Lys or Arg at the $9^{th}$ or $10^{th}$ position. Furthermore, those having a peptide length of 9 to 10 amino acids are well known (ref. Rapin N et al., Curr Protoc Immunol. 2010; Chapter 18: Unit 18.17). A sequence of three or four amino acids from the N terminal of the synthesized peptide is shown as an abbreviation for the peptide name. From the left, the peptide name, the amino acid sequence, the position in the BORIS B1 isoform sf5 and/or C7/C9 isoform sf6 amino acid sequence, the number of amino acids, and the score, calculated using NetMHC 3.4 HLA Peptide Binding Predictions (http://www.cbs.dtu.dk/services/NetMHC/), used for analysis are shown (ref. Nielsen et al., Protein Sci. 2003; 12: 1007-1017, Lundegaard et al., Nucleic Acids Res. 2008; 36 (Web Server issue): W509-512, Lundegaard et al., Bioinformatics. 2008; 24: 1397-1398). This score is a numerical value that is used for predicting the affinity between HLA-A*11:01 and a peptide, meaning the higher the score, the higher the possibility of HLA and the peptide forming a stable complex. The NetMHC 3.4 scores shown in Tables 9-1 and 9-2 are representative examples obtained using 11 types of analytical software for the analysis.

(7) Folding Test of BORIS-Specific HLA-A*11:01-Restricted CTL Epitope Candidate Peptides A folding test was carried out using the 13 types of synthesized peptides shown in Table 9-1. The folding test was carried out using the same method as in Example 4 (2) except that HLA-A*11:01 was used as the HLA, those peptides described in Table 9-1 were used as epitope peptides and, as comparative subjects, the peptide of SEQ ID No: 73 was used as a positive control and the peptide of SEQ ID No: 40 was used as a negative control.

The results of analysis 1, 3, and 7 days after the folding test carried out for the 15 types of peptides are shown in FIG.

46. As comparative subjects, an HLA-A*11:01-restricted CMV pp65 protein-derived peptide (ATV peptide, SEQ ID No: 73) was used as a positive control peptide, and an HLA-A*24:02-restricted survivin-2B-derived peptide (AYA peptide, SEQ ID No: 40) was used as a negative control. The peak areas reflecting HLA-monomer formation are shown by the bar graph. From the results, it was observed that the BORIS-specific CTL epitope candidate peptides (from SEQ ID No: 60 to SEQ ID No: 72) formed sufficient HLA-monomer compared with the negative control. That is, it was shown that the BORIS-specific CTL epitope candidate peptides described in Table 9-1 bind to HLA-A*11:01.

(8) Production of BORIS-Specific HLA-A*11:01-Restricted HLA-Tetramer Reagent

Based on the results of the folding test of (7), a PE-labeled HLA-tetramer reagent was produced by the same procedure as in Example 4 (3). However, the 13 types of BORIS-specific CTL epitope candidate peptides from SEQ ID No: 60 to SEQ ID No: 72 were used as epitope peptides, and HLA-A*11:01 was used as the HLA. From the results, an HLA-tetramer reagent was not produced for SEQ ID No: 68. Therefore, 12 types of HLA-tetramer reagents containing CTL epitope candidate peptides from SEQ ID No: 60 to SEQ ID No: 72, apart from SEQ ID No: 68, and HLA-A*11:01 were produced.

(9) Induction of BORIS-Specific CTLs

CTL induction was carried out by the same procedure as in Example 3 (5) using two healthy adults who were known to possess HLA-A*11:01 as subjects. However, as epitope peptides, mixture 1 of four types of peptide (SEQ ID No: 60, SEQ ID No: 63, SEQ ID No: 66 and SEQ ID No: 70), mixture 2 of four types of peptide (SEQ ID No: 61, SEQ ID No: 64, SEQ ID No: 67 and SEQ ID No: 71), or mixture 3 of four types of peptide (SEQ ID No: 62, SEQ ID No: 65, SEQ ID No: 69 and SEQ ID No: 72), in which four types of HLA-A*11:01-restricted CTL epitope candidates were mixed, were used.

Analysis of a cell population for which CTL induction was attempted was carried out in three stages. In the first stage, the cells of 8 wells in a column of a 96 well round-bottom cell culture micro test plate were collected as one sample. This sample was stained by the same procedure as in Example 3 (5) with HLA-tetramer mixed reagent 1 (SVL-Tet, NTH-Tet, KQL-Tet and GLI-Tet), HLA-tetramer mixed reagent 2 (SLA-Tet, CSY-Tet, TVY-Tet and TVL-Tet), or HLA-tetramer mixed reagent 3 (RMS-Tet, GTM-Tet, AAA-Tet and KLLF-Tet), which corresponded to the mixtures of four types of peptide used in induction, and the presence or absence of induction of BORIS-specific CTLs was ascertained. A sample for which CTL induction was confirmed in this stage was subjected to second stage analysis. In the second stage, cells were individually collected as a single sample from the 8 wells, this sample was stained with HLA-tetramer mixed reagent 1, 2, or 3, and the presence or absence of induction of BORIS-specific CTLs was ascertained. In the third stage, in order to find out which HLA-tetramer reagent among the HLA-tetramer mixed reagent the cells of a well for which CTL induction had been confirmed in the second stage would react with, detection of CTLs was carried out using the HLA-tetramer reagents individually. This method was used for ascertaining in which well of the 96 well round-bottom cell culture micro test plate CTLs having specificity for a peptide were induced.

FIG. 47 shows the results of first stage analysis. It shows the results of first stage analysis of a sample harvested from a culture obtained by culturing PBMCs of sample number *11-13 with mixture 1 of four types of peptide for 14 days. When staining with HLA-tetramer mixed reagent 1 was carried out by the same procedure as in Example 3 (5), a CD8-positive HLA-tetramer mixed reagent 1-positive cell population was clearly detected in the UR of lane 1. This result shows that at least one type of CTL epitope was present in the BORIS-specific CTL epitope candidates used for examination, and BORIS-specific CTLs were present within the living body of sample number A*11-13.

FIG. 48 shows the results of second stage analysis of lane 1, for which CTL induction had been confirmed in the first stage analysis. Induction of CTLs specific to an HLA-A*11:01-binding BORIS-specific CTL epitope was confirmed in well B of lane 1 (1-B).

FIG. 49 shows the results of third stage analysis of well B of lane 1, for which CTL induction had been confirmed in the second stage analysis. The results confirmed CTLs only when staining was carried out with KQL-Tet. This proves that the KQL peptide (SEQ ID No: 66) is an HLA-A*11:01-restricted BORIS-specific CTL epitope peptide.

FIG. 50 is the result of first stage analysis. It shows the results of first stage analysis of a sample harvested from a culture obtained by culturing PBMCs of sample number *11-13 with mixture 2 of four types of peptide for 14 days. When staining with HLA-tetramer mixed reagent 2 was carried out by the same procedure as in Example 3 (5), a CD8-positive HLA-tetramer mixed reagent 2-positive cell population was clearly detected in the UR of lane 12. This result shows that at least one type of CTL epitope was present in the BORIS-specific CTL epitope candidates used for examination, and BORIS-specific CTLs were present within the living body of sample number A*11-13.

FIG. 51 shows the results of second stage analysis of lane 12, for which CTL induction had been confirmed in the first stage analysis. Induction of CTLs specific to an HLA-A*11:01-binding BORIS-specific CTL epitope was confirmed in well E of lane 12 (12-E).

FIG. 52 shows the results of third stage analysis of well E of lane 12, for which CTL induction had been confirmed in the second stage analysis. The results confirmed CTLs only when staining was carried out with TVY-Tet. This proves that the TVY peptide (SEQ ID No: 67) is an HLA-A*11:01-restricted BORIS-specific CTL epitope peptide.

FIG. 53 is the result of a first stage analysis. It shows the results of first stage analysis of a sample harvested from a culture obtained by culturing PBMCs of sample number *11-16 with mixture 3 of four types of peptide for 14 days. When staining with HLA-tetramer mixed reagent 3 was carried out by the same procedure as in Example 3 (5), CD8-positive HLA-tetramer mixed reagent 3-positive cell populations were clearly detected in the UR of lane 7 and lane 11. This result shows that at least one type of CTL epitope was present in the BORIS-specific CTL epitope candidates used for examination, and BORIS-specific CTLs were present within the living body of sample number A*11-16.

FIG. 54 shows the results of second stage analysis of lane 7 and lane 11, for which CTL induction had been confirmed in the first stage analysis. Induction of CTLs specific to an HLA-A*11:01-restricted BORIS-specific CTL epitope was confirmed for well E of lane 7 (7-E) and well H of lane 11 (11-H).

FIG. 55 shows the results of third stage analysis of well E of lane 7 and well H of lane 11, for which CTL induction had been confirmed in the second stage analysis. CTLs were confirmed only when staining with GTM-Tet for well E of lane 7 and only when staining with KLLF-Tet for well H of lane 11. This proves that the GTM peptide (SEQ ID No: 65) and the KLLF peptide (SEQ ID No: 72) are HLA-A*11:01-restricted BORIS-specific CTL epitope peptides.

Example 6

Preparation of BORIS sf5- and sf6-Specific Antibodies

In order to obtain BORIS sf5- and BORIS sf6-specific antibodies, peptide sequences formed from 8 to 20 amino acids were synthesized from SEQ ID No: 1 and SEQ ID No: 2, a cysteine residue was added to the C terminal or N terminal of the peptide, and they were bonded to KHL (Keyhole limpet hemocyanin) and used as immunogens in accordance with a standard method. Rabbits and guinea pigs were immunized 4 to 6 times every other week or every week. After completion of immunization, blood was collected from the individuals, and a specific antibody was purified using an affinity column prepared with the peptide used as the immunogen.

A specificity test was carried out using a cell extract of cultured 293T cells in which BORIS sf5 and BORIS sf6 were transiently expressed and a cell extract of untreated 293T cells. A Myc Tag sequence was added to the BORIS sf5 and BORIS sf6 genes, which had been transiently expressed, and a Myc Tag antibody specific thereto was used as a positive control.

As shown in FIG. 56, as a result of testing by western blotting, for both the BORIS sf5- and BORIS sf6-specific antibodies thus obtained, a band was detected at a position showing the same molecular size as a band detected for the positive control when the respective extract from the BORIS-expressing 293T cells was used, whereas for neither thereof was a band detected for the extract from the untreated 293T cells. It is considered from this that antibodies specifically binding to BORIS sf5 and BORIS sf6 could be obtained. When a cancer-affected tissue section resected from a lung cancer patient was stained with the BORIS sf5-specific antibody, it was established that it was sometimes determined as being negative and was sometimes determined as being positive (ref. FIG. 57). It is possible by the use of the specific antibody thus obtained to ascertain the presence or absence of expression of the respective BORIS sf5 and BORIS sf6, and it can be a useful tool for determining the feasibility of a peptide vaccine therapy, etc. using a CTL epitope peptide identified in the present invention.

Example 7

Preparation of siRNA for BORIS sf6

(1) Design of siRNA

MS751 and CaSki were each transfected with siRNAs for BORIS that had been designed to have the sequences shown in the table below in accordance with the protocol described in the Instructions by the manufacturer for the Lipofectamine RNAiMAX used. Cells were analyzed 48 hours after transfection. Trilencer-27 Universal Scrambled Negative Control siRNA (SR30004, Origene) was used as a negative control.

TABLE 10

Table 10: Sequence of siRNAs 1 to 3

| | Sequence | SEQ ID No: |
|---|---|---|
| siRNA1 (siBORIS1) | rGrCrArArUrUrCrArCrCrArArGrArUr CrArArArGrArArCTC (*Silencing of BORIS transcripts sf 1, 2, 3(A5A6C6), 4(C3C4C5C8), 5, 6(C7C9).) | 44 |
| siRNA2 (siBORIS2) | rGrGrArArArUrArCrCrArCrGrArUrGr CrArArArUrUrUrCAT (*Silencing of BORIS transcripts sf 1, 3, 4(B2B3C3C4), 5.) | 45 |
| siRNA3 (siBORIS3) | rArGrCrUrGrGrArUrArUrUrCrArAr ArGrArArCrArUTG (*Silencing of BORIS transcript sf1.) | 46 |

The results of knockdown are shown in FIGS. 14 and 15. FIG. 14-1(a) shows that the level of expression of BORIS (B0) was markedly suppressed by the three types of siRNA (quantitative RT-PCR). Furthermore, it was observed from FIG. 14-1(b) and FIG. 14-2 that cell proliferation was slightly suppressed with siRNA1 and siRNA2. It is thought probable that the higher the number of BORIS subfamilies suppressed, the higher the proliferation suppression effect. However, in siRNA1 and siRNA2 stemness gene suppression did not occur at all (FIG. 15).

Furthermore, as shown in FIGS. 16-1 and 16-2, the sphere formation capability of each of CaSki and MS751 was markedly suppressed by siRNA2 (did not necessarily coincide with the result of cell proliferation suppression).

Moreover, knockdown by siRNA1 to 3 did not affect the radiation tolerance (FIG. 17).

It can be seen from FIG. 18 that when BORIS expression is high the survival rate is lowered greatly. Because of this, BORIS can be recognized as being a significant factor in a poor prognosis.

INDUSTRIAL APPLICABILITY

In accordance with the present invention, a treatment agent that is effective for various types of cancer can be provided. In particular, the epitope peptide of the present invention can induce the CTLs that specifically attack various types of cancer cells, in particular cancer stem cells that are thought to be the cause of a malignant tumor, and they are very useful as an anticancer agent having few side effects and high effectiveness.

The invention claimed is:

1. A method for inducing a cytotoxic T cell (CTL) that specifically recognizes a cell expressing a BORIS gene belonging to isoform A or C or a BORIS gene belonging to subfamily 5 or 6, the method comprising contacting in vitro:
   (a) a polypeptide comprising the amino acids of SEQ ID NO: 3, SEQ ID NO: 10, SEQ ID NO: 65, SEQ ID NO: 66, SEQ ID NO: 67 or SEQ ID NO: 72, and having HLA-A11 antigen-binding capacity or HLA-A24 antigen-binding capacity, with a peripheral blood lymphocyte (PBL) expressing on the cell surface HLA-A11 antigen or HLA-A24 antigen,
   (b) a polypeptide comprising the amino acids of SEQ ID NO: 4, SEQ ID NO: 5, SEQ ID NO: 10, SEQ ID NO: 47, or SEQ ID NO: 57, and having HLA-A2 antigen binding capacity, with a PBL expressing on the cell surface HLA-A2 antigen, or
   (c) an expression vector encoding at least one of the polypeptides of (a) with the PBL expressing on the cell surface the HLA-A11 antigen or the HLA-A24 antigen or the polypeptide of (b) above with the PBL expressing on the cell surface the HLA-A2 antigen, wherein the sequence encoding the polypeptide of (a) or the polypeptide of (b) is operably linked to an expression control sequence:

wherein the polypeptide induces the CTL.

2. The method according to claim 1, the polypeptide of (a) having the HLA-A11 antigen-binding capacity.

3. The method according to claim 1, the polypeptide of (a) having the HLA-A24 antigen-binding capacity.

4. The method according to claim 1, the step of contacting in vitro further comprising pulsing the PBL with the polypeptide.

5. The method according to claim 1, the method further comprising intravenous, subcutaneous or intradermal administration of a pharmaceutical composition containing as an active ingredient the CTL to a patient having a cancer that is positive for the BORIS gene belonging to the isoform A or C or the BORIS gene belonging to the subfamily 5 or 6, wherein the PBL is obtained from the patient.

6. A method of treating a lung cancer or a female reproductive organ cancer comprising intravenously or subcutaneously administering to a subject with the lung cancer or the female reproductive organ cancer:
  (a) a polypeptide comprising the amino acids of SEQ ID NO: 3, SEQ ID NO: 10, SEQ ID NO: 65, SEQ ID NO: 66, SEQ ID NO: 67 or SEQ ID NO: 72 and having HLA-A11 antigen-binding capacity or HLA-A24 antigen-binding capacity, or
  (b) a polypeptide comprising the amino acids of SEQ ID NO: 4, SEQ ID NO: 5, SEQ ID NO: 10, SEQ ID NO: 47, or SEQ ID NO: 57, and having HLA-A2 antigen binding capacity, wherein the administered polypeptide induces CTL upon contact with PBLs in the subject expressing on the cell surface the HLA-A11 antigen or the HLA-A24 antigen or the polypeptide of (b) with the PBLs expressing on the cell surface the HLA-A2 antigen, wherein the lung cancer or the cancer in a female specific reproductive organ cancer expresses a BORIS gene belonging to isoform A or C or a BORIS gene belonging to subfamily 5 or 6, wherein the subject administered the polypeptide of (a) is the HLA-A11 antigen positive or the HLA-A24 antigen positive, or the subject administered the polypeptide of (b) is the HLA-A2 antigen positive, and wherein the CTL induction treats the lung cancer or the female reproductive organ cancer.

7. The method according to claim 6, wherein the lung cancer or the female reproductive organ cancer comprises a cancer stem cell.

* * * * *

SEQUENCE LISTING

<160> NUMBER OF SEQ ID NOS: 76

<210> SEQ ID NO 1
<211> LENGTH: 32
<212> TYPE: PRT
<213> ORGANISM: Homo sapiens

```
<400> SEQUENCE: 1

Lys Gly Ser Gly Ala Glu Gly Leu Ile Pro Thr Val Leu Thr Leu Lys
1               5                   10                  15

Ala Ser Phe Lys Lys Leu Leu Phe Ile Gly Thr Ile Lys Val Gln Arg
                20                  25                  30

<210> SEQ ID NO 2
<211> LENGTH: 38
<212> TYPE: PRT
<213> ORGANISM: Homo sapiens

<400> SEQUENCE: 2

Asn Ser Ala Gly Cys Thr Gly Arg Met Met Leu Val Ser Ala Trp Leu
1               5                   10                  15

Leu Gly Arg Pro Gln Glu Thr Tyr Asn Gln Gly Arg Arg Arg Arg Gly
                20                  25                  30

Ser Arg Arg Val Thr Trp
            35

<210> SEQ ID NO 3
<211> LENGTH: 11
<212> TYPE: PRT
<213> ORGANISM: Artificial Sequence
<220> FEATURE:
<223> OTHER INFORMATION: HLA-A02 binding peptide

<400> SEQUENCE: 3

Ser Phe Lys Lys Leu Leu Phe Ile Gly Thr Ile
1               5                   10

<210> SEQ ID NO 4
<211> LENGTH: 10
<212> TYPE: PRT
<213> ORGANISM: Artificial Sequence
<220> FEATURE:
<223> OTHER INFORMATION: tumor antigen peptide

<400> SEQUENCE: 4

Lys Leu Leu Phe Ile Gly Thr Ile Lys Val
1               5                   10

<210> SEQ ID NO 5
<211> LENGTH: 9
<212> TYPE: PRT
<213> ORGANISM: Artificial Sequence
<220> FEATURE:
<223> OTHER INFORMATION: HLA-A24 binding peptide

<400> SEQUENCE: 5

Leu Leu Phe Ile Gly Thr Ile Lys Val
1               5

<210> SEQ ID NO 6
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 6

Val Phe His Glu Arg Tyr Ala Leu Ile
1               5

<210> SEQ ID NO 7
```

```
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 7

Thr Phe His Cys Asp Val Cys Met Phe
1               5

<210> SEQ ID NO 8
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 8

His Phe Thr Ser Glu Ala Val Glu Leu
1               5

<210> SEQ ID NO 9
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 9

Lys Tyr Ile Leu Thr Leu Gln Thr Val
1               5

<210> SEQ ID NO 10
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 10

Arg Met Met Leu Val Ser Ala Trp Leu
1               5

<210> SEQ ID NO 11
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 11

Lys Tyr Gln Cys Pro His Cys Ala Thr
1               5

<210> SEQ ID NO 12
<211> LENGTH: 10
<212> TYPE: PRT
<213> ORGANISM: Artificial Sequence
<220> FEATURE:
<223> OTHER INFORMATION: candidate of CTL epitope peptide

<400> SEQUENCE: 12

Lys Tyr Ala Ser Val Glu Ala Ser Lys Leu
1               5                   10

<210> SEQ ID NO 13
<211> LENGTH: 10
```

```
<212> TYPE: PRT
<213> ORGANISM: Artificial Sequence
<220> FEATURE:
<223> OTHER INFORMATION: candidate of CTL epitope peptide

<400> SEQUENCE: 13

Leu Tyr Ser Pro Gln Glu Met Glu Val Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: candidate of CTL epitope peptide

<400> SEQUENCE: 14

Ser Tyr Ala Ser Arg Asp Thr Tyr Lys Leu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: candidate of CTL epitope peptide

<400> SEQUENCE: 15

Lys Tyr Gln Cys Pro His Cys Ala Thr Ile
1               5                   10

<210> SEQ ID NO 16
<211> LENGTH: 10
<212> TYPE: PRT
<213> ORGANISM: Artificial Sequence
<220> FEATURE:
<223> OTHER INFORMATION: candidate of CTL epitope peptide

<400> SEQUENCE: 16

Arg Tyr Lys His Thr His Glu Lys Pro Phe
1               5                   10

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ctgcgaaggg atggaaggaa                                                    20

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
gaacacgcaa cccgaatcc                                                     19

<210> SEQ ID NO 19
<211> LENGTH: 20
<212> TYPE: DNA
<213> ORGANISM: Artificial Sequence
<220> FEATURE:
```

```
<223> OTHER INFORMATION: primer

<400> SEQUENCE: 19
ggataattcc gcaggctgta                                              20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tggtcgttca gaggagtgtg                                              20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
taacacccac acaggaacca                                              20

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
gcctctacta agatgccatg aa                                           22

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
cttttcccgc tggattctct                                              20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
gtcaggagga cactcaagca                                              20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ccattcacct gcctttcttg                                              20
```

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
ggttttaagc cactccattt tg                                    22

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ccacaaaggg tcagaaggaa                                       20

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
ggtcaggagt gagagacatg g                                     21

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
tgtgatgtct gcatgttcac c                                     21

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
gcagatcact tgaggtcagg a                                     21

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
tgcacagaca ttcggagaag                                       20

<210> SEQ ID NO 32
<211> LENGTH: 20
<212> TYPE: DNA
<213> ORGANISM: Artificial Sequence
<220> FEATURE:
<223> OTHER INFORMATION: primer

```
<400> SEQUENCE: 32
agatcacacc gtctccgttc                                              20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
ctcaggtaag ggctctggtg                                              20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tactccacac agtggggttg                                              20

<210> SEQ ID NO 35
<211> LENGTH: 20
<212> TYPE: DNA
<213> ORGANISM: Artificial Sequence
<220> FEATURE:
<223> OTHER INFORMATION: forward primer for BORIS

<400> SEQUENCE: 35
gatgctgaaa aggccaaatc                                              20

<210> SEQ ID NO 36
<211> LENGTH: 20
<212> TYPE: DNA
<213> ORGANISM: Artificial Sequence
<220> FEATURE:
<223> OTHER INFORMATION: reverse primer for BORIS

<400> SEQUENCE: 36
acttgtaggg cctggttcct                                              20

<210> SEQ ID NO 37
<211> LENGTH: 9
<212> TYPE: PRT
<213> ORGANISM: Artificial Sequence
<220> FEATURE:
<223> OTHER INFORMATION: synthetic peptide

<400> SEQUENCE: 37

Asn Leu Val Pro Met Val Ala Thr Val
1               5

<210> SEQ ID NO 38
<211> LENGTH: 9
<212> TYPE: PRT
<213> ORGANISM: Artificial Sequence
<220> FEATURE:
<223> OTHER INFORMATION: synthetic peptide

<400> SEQUENCE: 38

Gly Ile Leu Gly Phe Val Phe Thr Leu
1               5
```

<210> SEQ ID NO 39
<211> LENGTH: 12
<212> TYPE: PRT
<213> ORGANISM: Artificial Sequence
<220> FEATURE:
<223> OTHER INFORMATION: synthetic peptide

<400> SEQUENCE: 39

Gly Tyr Ile Ser Pro Tyr Phe Ile Asn Thr Ser Lys
1 5 10

<210> SEQ ID NO 40
<211> LENGTH: 9
<212> TYPE: PRT
<213> ORGANISM: Artificial Sequence
<220> FEATURE:
<223> OTHER INFORMATION: synthetic peptide

<400> SEQUENCE: 40

Ala Tyr Ala Cys Asn Thr Ser Thr Leu
1 5

<210> SEQ ID NO 41
<211> LENGTH: 10
<212> TYPE: PRT
<213> ORGANISM: Artificial Sequence
<220> FEATURE:
<223> OTHER INFORMATION: synthetic peptide

<400> SEQUENCE: 41

Glu Trp Trp Arg Ser Gly Gly Phe Ser Phe
1 5 10

<210> SEQ ID NO 42
<211> LENGTH: 9
<212> TYPE: PRT
<213> ORGANISM: Artificial Sequence
<220> FEATURE:
<223> OTHER INFORMATION: synthetic peptide

<400> SEQUENCE: 42

Ser Ser Tyr Arg Arg Pro Val Gly Ile
1 5

<210> SEQ ID NO 43
<211> LENGTH: 10
<212> TYPE: PRT
<213> ORGANISM: Artificial Sequence
<220> FEATURE:
<223> OTHER INFORMATION: synthetic peptide

<400> SEQUENCE: 43

Ser Ser Leu Glu Asn Phe Arg Ala Tyr Val
1 5 10

<210> SEQ ID NO 44
<211> LENGTH: 48
<212> TYPE: DNA
<213> ORGANISM: Artificial Sequence
<220> FEATURE:
<223> OTHER INFORMATION: siRNA

<400> SEQUENCE: 44
rgrcmararu rurcrarcrc rarargraru rcrarararg rararctc 48

<210> SEQ ID NO 45
<211> LENGTH: 48

<212> TYPE: DNA
<213> ORGANISM: Artificial Sequence
<220> FEATURE:
<223> OTHER INFORMATION: siRNA

<400> SEQUENCE: 45
rgrgrarara rurarcrcra rcrgrarurg rcrarararu rururcat 48

<210> SEQ ID NO 46
<211> LENGTH: 48
<212> TYPE: DNA
<213> ORGANISM: Artificial Sequence
<220> FEATURE:
<223> OTHER INFORMATION: siRNA

<400> SEQUENCE: 46
rargrcrurg rgraruraru rururcrara rargrarara rcrarutg 48

<210> SEQ ID NO 47
<211> LENGTH: 9
<212> TYPE: PRT
<213> ORGANISM: Artificial Sequence
<220> FEATURE:
<223> OTHER INFORMATION: tumor antigen peptide

<400> SEQUENCE: 47

Val Leu Glu Glu Glu Val Glu Leu Val
1 5

<210> SEQ ID NO 48
<211> LENGTH: 9
<212> TYPE: PRT
<213> ORGANISM: Artificial Sequence
<220> FEATURE:
<223> OTHER INFORMATION: tumor antigen peptide

<400> SEQUENCE: 48

Lys Leu Ala Val Ser Leu Ala Glu Thr
1 5

<210> SEQ ID NO 49
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 49

Ser Val Leu Glu Glu Glu Val Glu Leu
1 5

<210> SEQ ID NO 50
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 50

Ser Leu Ala Glu Thr Ala Gly Leu Ile
1 5

<210> SEQ ID NO 51
<211> LENGTH: 9
<212> TYPE: PRT
<213> ORGANISM: Artificial Sequence
<220> FEATURE:

```
<223> OTHER INFORMATION: candidate of CTL epitope peptide

<400> SEQUENCE: 51

Val Leu Ser Glu Gln Phe Thr Lys Ile
1               5

<210> SEQ ID NO 52
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 52

Ile Leu Gln Lys His Gly Glu Asn Val
1               5

<210> SEQ ID NO 53
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 53

Ala Leu Glu Glu Asn Val Met Val Ala
1               5

<210> SEQ ID NO 54
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 54

Tyr Ala Ser Arg Asp Thr Tyr Lys Leu
1               5

<210> SEQ ID NO 55
<211> LENGTH: 9
<212> TYPE: PRT
<213> ORGANISM: Artificial Sequence
<220> FEATURE:
<223> OTHER INFORMATION: candidate of HLA-A02:01 binding peptide

<400> SEQUENCE: 55

Met Ala Ala Thr Glu Ile Ser Val Leu
1               5

<210> SEQ ID NO 56
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 56

His Ala Leu Glu Glu Asn Val Met Val
1               5

<210> SEQ ID NO 57
<211> LENGTH: 9
<212> TYPE: PRT
<213> ORGANISM: Artificial Sequence
<220> FEATURE:
<223> OTHER INFORMATION: tumor antigen peptide
```

```
<400> SEQUENCE: 57

Val Leu Thr Val Ser Asn Ser Asn Val
1               5

<210> SEQ ID NO 58
<211> LENGTH: 9
<212> TYPE: PRT
<213> ORGANISM: Artificial Sequence
<220> FEATURE:
<223> OTHER INFORMATION: synthetic peptide

<400> SEQUENCE: 58

Arg Met Phe Pro Asn Ala Pro Tyr Leu
1               5

<210> SEQ ID NO 59
<211> LENGTH: 9
<212> TYPE: PRT
<213> ORGANISM: Artificial Sequence
<220> FEATURE:
<223> OTHER INFORMATION: synthetic peptide

<400> SEQUENCE: 59

Lys Ala Val Tyr Asn Phe Ala Thr Met
1               5

<210> SEQ ID NO 60
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 60

Ser Val Leu Ser Glu Gln Phe Thr Lys
1               5

<210> SEQ ID NO 61
<211> LENGTH: 10
<212> TYPE: PRT
<213> ORGANISM: Artificial Sequence
<220> FEATURE:
<223> OTHER INFORMATION: candidate of CTL epitope peptide

<400> SEQUENCE: 61

Ser Leu Ala Glu Thr Thr Gly Leu Ile Lys
1               5                   10

<210> SEQ ID NO 62
<211> LENGTH: 10
<212> TYPE: PRT
<213> ORGANISM: Artificial Sequence
<220> FEATURE:
<223> OTHER INFORMATION: candidate of CTL epitope peptide

<400> SEQUENCE: 62

Arg Met Ser Ser Phe Asn Arg His Met Lys
1               5                   10

<210> SEQ ID NO 63
<211> LENGTH: 10
<212> TYPE: PRT
<213> ORGANISM: Artificial Sequence
<220> FEATURE:
<223> OTHER INFORMATION: candidate of CTL epitope peptide
```

```
<400> SEQUENCE: 63

Asn Thr His Thr Gly Thr Arg Pro Tyr Lys
1               5                   10

<210> SEQ ID NO 64
<211> LENGTH: 10
<212> TYPE: PRT
<213> ORGANISM: Artificial Sequence
<220> FEATURE:
<223> OTHER INFORMATION: candidate of CTL epitope peptide

<400> SEQUENCE: 64

Cys Ser Tyr Ala Ser Arg Asp Thr Tyr Lys
1               5                   10

<210> SEQ ID NO 65
<211> LENGTH: 10
<212> TYPE: PRT
<213> ORGANISM: Artificial Sequence
<220> FEATURE:
<223> OTHER INFORMATION: tumor antigen peptide

<400> SEQUENCE: 65

Gly Thr Met Lys Ile His Ile Leu Gln Lys
1               5                   10

<210> SEQ ID NO 66
<211> LENGTH: 10
<212> TYPE: PRT
<213> ORGANISM: Artificial Sequence
<220> FEATURE:
<223> OTHER INFORMATION: tumor antigen peptide

<400> SEQUENCE: 66

Lys Gln Leu Leu Asn Ala His Phe Arg Lys
1               5                   10

<210> SEQ ID NO 67
<211> LENGTH: 10
<212> TYPE: PRT
<213> ORGANISM: Artificial Sequence
<220> FEATURE:
<223> OTHER INFORMATION: tumor antigen peptide

<400> SEQUENCE: 67

Thr Val Tyr Lys Cys Ser Lys Cys Gly Lys
1               5                   10

<210> SEQ ID NO 68
<211> LENGTH: 10
<212> TYPE: PRT
<213> ORGANISM: Artificial Sequence
<220> FEATURE:
<223> OTHER INFORMATION: HLA-A11:01 binding peptide

<400> SEQUENCE: 68

Ala Ser Gly Lys Gly Arg Arg Thr Arg Lys
1               5                   10

<210> SEQ ID NO 69
<211> LENGTH: 10
<212> TYPE: PRT
<213> ORGANISM: Artificial Sequence
<220> FEATURE:
<223> OTHER INFORMATION: candidate of CTL epitope peptide

<400> SEQUENCE: 69
```

```
Ala Ala Ala Glu Glu Ala Ser Thr Thr Lys
1               5                   10

<210> SEQ ID NO 70
<211> LENGTH: 10
<212> TYPE: PRT
<213> ORGANISM: Artificial Sequence
<220> FEATURE:
<223> OTHER INFORMATION: candidate of CTL epitope peptide

<400> SEQUENCE: 70

Gly Leu Ile Pro Thr Val Leu Thr Leu Lys
1               5                   10

<210> SEQ ID NO 71
<211> LENGTH: 10
<212> TYPE: PRT
<213> ORGANISM: Artificial Sequence
<220> FEATURE:
<223> OTHER INFORMATION: candidate of CTL epitope peptide

<400> SEQUENCE: 71

Thr Val Leu Thr Leu Lys Ala Ser Phe Lys
1               5                   10

<210> SEQ ID NO 72
<211> LENGTH: 9
<212> TYPE: PRT
<213> ORGANISM: Artificial Sequence
<220> FEATURE:
<223> OTHER INFORMATION: tumor antigen peptide

<400> SEQUENCE: 72

Lys Leu Leu Phe Ile Gly Thr Ile Lys
1               5

<210> SEQ ID NO 73
<211> LENGTH: 9
<212> TYPE: PRT
<213> ORGANISM: Artificial Sequence
<220> FEATURE:
<223> OTHER INFORMATION: candidate of CTL epitope peptide

<400> SEQUENCE: 73

Ala Thr Val Gln Gly Gln Asn Leu Lys
1               5

<210> SEQ ID NO 74
<211> LENGTH: 9
<212> TYPE: PRT
<213> ORGANISM: Artificial Sequence
<220> FEATURE:
<223> OTHER INFORMATION: synthetic peptide

<400> SEQUENCE: 74

Ser Leu Tyr Asn Thr Val Ala Thr Leu
1               5

<210> SEQ ID NO 75
<211> LENGTH: 10
<212> TYPE: PRT
<213> ORGANISM: Artificial Sequence
<220> FEATURE:
<223> OTHER INFORMATION: synthetic peptide

<400> SEQUENCE: 75
```

Arg Tyr Leu Arg Gln Gln Leu Leu Gly Ile
1               5                   10

<210> SEQ ID NO 76
<211> LENGTH: 663
<212> TYPE: PRT
<213> ORGANISM: Homo sapiens

<400> SEQUENCE: 76

Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
            20                  25                  30

Asp Gly Val Cys Arg Glu Lys Asp His Arg Ser Pro Ser Glu Leu Glu
        35                  40                  45

Ala Glu Arg Thr Ser Gly Ala Phe Gln Asp Ser Val Leu Glu Glu Glu
    50                  55                  60

Val Glu Leu Val Leu Ala Pro Ser Glu Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Glu Gly Val Gln Val Val
            100                 105                 110

Gln Gln Pro Gly Pro Gly Leu Leu Trp Leu Glu Glu Gly Pro Arg Gln
            115                 120                 125

Ser Leu Gln Gln Cys Val Ala Ile Ser Ile Gln Gln Glu Leu Tyr Ser
        130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Ala Gly Leu Ile Lys Leu Glu Glu Gln Glu Lys Asn Gln Leu Leu
            180                 185                 190

Ala Glu Arg Thr Lys Glu Gln Leu Phe Phe Val Glu Thr Met Ser Gly
        195                 200                 205

Asp Glu Arg Ser Asp Glu Ile Val Leu Thr Val Ser Asn Ser Asn Val
    210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Gly Thr
                245                 250                 255

Phe His Cys Asp Val Cys Met Phe Thr Ser Ser Arg Met Ser Ser Phe
            260                 265                 270

Asn Arg His Met Lys Thr His Thr Ser Glu Lys Pro His Leu Cys His
        275                 280                 285

Leu Cys Leu Lys Thr Phe Arg Thr Val Thr Leu Leu Arg Asn His Val
    290                 295                 300

Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Arg Tyr Lys His
                325                 330                 335

Thr His Glu Lys Pro Phe Lys Cys Ser Met Cys Lys Tyr Ala Ser Val
            340                 345                 350

Glu Ala Ser Lys Leu Lys Arg His Val Arg Ser His Thr Gly Glu Arg
        355                 360                 365

-continued

```
Pro Phe Gln Cys Cys Gln Cys Ser Tyr Ala Ser Arg Asp Thr Tyr Lys
    370             375                 380

Leu Lys Arg His Met Arg Thr His Ser Gly Glu Lys Pro Tyr Glu Cys
385                 390                 395                 400

His Ile Cys His Thr Arg Phe Thr Gln Ser Gly Thr Met Lys Ile His
            405                 410                 415

Ile Leu Gln Lys His Gly Glu Asn Val Pro Lys Tyr Gln Cys Pro His
            420                 425                 430

Cys Ala Thr Ile Ile Ala Arg Lys Ser Asp Leu Arg Val His Met Arg
            435                 440                 445

Asn Leu His Ala Tyr Ser Ala Ala Glu Leu Lys Cys Arg Tyr Cys Ser
    450                 455                 460

Ala Val Phe His Glu Arg Tyr Ala Leu Ile Gln His Gln Lys Thr His
465                 470                 475                 480

Lys Asn Glu Lys Arg Phe Lys Cys Lys His Cys Ser Tyr Ala Cys Lys
                485                 490                 495

Gln Glu Arg His Met Thr Ala His Ile Arg Thr His Thr Gly Glu Lys
            500                 505                 510

Pro Phe Thr Cys Leu Ser Cys Asn Lys Cys Phe Arg Gln Lys Gln Leu
            515                 520                 525

Leu Asn Ala His Phe Arg Lys Tyr His Asp Ala Asn Phe Ile Pro Thr
    530                 535                 540

Val Tyr Lys Cys Ser Lys Cys Gly Lys Gly Phe Ser Arg Trp Ile Asn
545                 550                 555                 560

Leu His Arg His Ser Glu Lys Cys Gly Ser Gly Glu Ala Lys Ser Ala
                565                 570                 575

Ala Ser Gly Lys Gly Arg Arg Thr Arg Lys Arg Lys Gln Thr Ile Leu
            580                 585                 590

Lys Glu Ala Thr Lys Gly Gln Lys Glu Ala Ala Lys Gly Trp Lys Glu
            595                 600                 605

Ala Ala Asn Gly Asp Glu Ala Ala Glu Glu Ala Ser Thr Thr Lys
            610                 615                 620

Gly Glu Gln Phe Pro Gly Glu Met Phe Pro Val Ala Cys Arg Glu Thr
625                 630                 635                 640

Thr Ala Arg Val Lys Glu Glu Val Asp Glu Gly Val Thr Cys Glu Met
                645                 650                 655

Leu Leu Asn Thr Met Asp Lys
                660
```